United States Patent [19]
Ozaki et al.

[11] Patent Number: 5,252,707
[45] Date of Patent: Oct. 12, 1993

[54] INOSITOL DERIVATIVE AND METHOD FOR PREPARING SAME

[75] Inventors: Shoichiro Ozaki; Yutaka Watanabe, both of Matsuyama; Masato Hirata, Fukuoka; Akira Awaya, Yokohama, all of Japan

[73] Assignee: Mitsui Toatsu Chemicals Incorporated, Tokyo, Japan

[21] Appl. No.: 700,152

[22] PCT Filed: Sep. 25, 1990

[86] PCT No.: PCT/JP90/01228

§ 371 Date: May 15, 1991

§ 102(e) Date: May 15, 1991

[87] PCT Pub. No.: WO91/04258

PCT Pub. Date: Apr. 4, 1991

[30] Foreign Application Priority Data

Sep. 22, 1989 [JP] Japan .................. 1-245161
Aug. 10, 1990 [JP] Japan .................. 2-210263

[51] Int. Cl.[5] .............. A61K 37/02; C07F 9/117; C07K 17/02; C12N 9/00
[52] U.S. Cl. .............. 530/345; 530/409; 530/410; 560/53; 560/116; 560/118; 560/155; 560/169; 560/170
[58] Field of Search .............. 514/7, 103; 530/345, 530/402, 409, 410; 534/653; 558/302; 560/53, 116, 118, 155, 169, 170

[56] References Cited

U.S. PATENT DOCUMENTS 4,801,597 1/1989 Stackpole et al. .................. 514/332
4,873,355 10/1989 Hobbs et al. ...................... 558/161

FOREIGN PATENT DOCUMENTS 0262227 4/1988 European Pat. Off. .
168299 7/1989 Japan .

OTHER PUBLICATIONS

Chemical Abstract 107:237,170w (1987).
Hirata et al, "Synthetic Inositol Triphosphate Analogs . . . ", *J. Biol. Chem.* 264(34), Dec. 5, 1989. pp. 20303–20308.
Hirata et al, "Stereospecific Recognition of Inositol 1,4,5-Trisphosphate Analogs . . . ", *J. Biol. Chem.* 265(15), May 25, 1990, pp. 8404–8407.
Hirata et al, "Irreversible inhibition of $Ca^{2+}$ release . . . ", *Nature* vol. 317, Oct. 2, 1985, pp. 723–725.
Ishimatsu et al, "Possible Binding Sites For Inositol 1,4,5-Trisphosphate . . . ", *Biochem. Biophys. Res. Comm.* 155(3), Sep. 30, 1988, pp. 1173–1180.
Schultz et al, "cis,cis-Cyclohexane 1,3,5-Triol Polyphosphates . . .", *Biochem. Biophys. Res. Comm.* 166(3) Feb. 14, 1990, pp. 1319–1327.

Primary Examiner—Jeffrey E. Russel
Attorney, Agent, or Firm—Nixon & Vanderhye

[57] ABSTRACT

There are disclosed a novel inositol-1,4,5-triphosphoric acid derivative, inositol-1,3,4-triphosphoric acid derivative, inositol-1,3,4,5-tetraphosphoric acid derivative, and a bonded substance of the same and a protein. They control the metabolic process of an organism concerned with calcium ions to thereby exert a medicinal virtue.

7 Claims, 26 Drawing Sheets $IP_4$ (DL-)

$IP_3$ (D-)

KG194 (DL-)

209 (DL-)

KG210 (DL-)

206 (DL-)

(RX, a and b are referred in Fig. 10)

INOSITOL DERIVATIVE AND METHOD FOR PREPARING SAME

DESCRIPTION

1. Technical Field

The present invention relates to a novel inositol derivative, particularly an inositol-1,4,5-triphosphoric acid (hereinafter referred to as "IP$_3$") derivative, an inositol-1,3,4-triphosphoric acid (hereinafter referred to as "1,3,4-IP$_3$") derivative, an inositol-1,3,4,5-tetraphosphoric acid (hereinafter referred to as "IP$_4$") derivative, their pharmaceutically acceptable salts, and a novel therapeutic medicine for various diseases of animals containing any of the above-mentioned compounds as an effective component, the aforesaid therapeutic medicine being capable of controlling the metabolic process of an organism concerned with calcium ions or controlling proteins to be bonded to or for recognizing IP$_3$, 1,3,4-IP$_3$, IP$_4$ or the like so as to thereby exert a medicinal virtue. Furthermore, the present invention relates to a method for preparing the above-mentioned novel inositol derivatives, particularly the P$_3$ derivative, the 1,3,4-IP$_3$ derivative, the IP$_4$ derivative or their pharmaceutically acceptable salts, a solid phase carrier which is bonded to the above-mentioned inositol derivative, particularly the IP$_3$ derivative, the 1,3,4-IP$_3$ derivative or the IP$_4$ derivative having affinity for proteins to be bonded to or for recognizing IP$_3$, 1,3,4-IP$_3$, IP$_4$ or the like, and a process for preparing the solid phase carrier.

SUMMARY OF THE INVENTION

Disclosed are novel inositol derivatives represented by the formula (I)

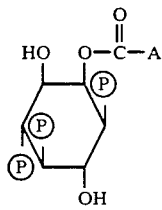

(I)

where A is (CH$_2$)$_n$CH(R')NH$_2$,

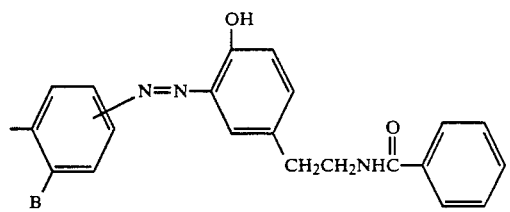

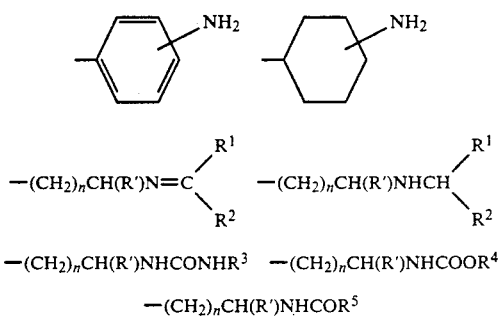

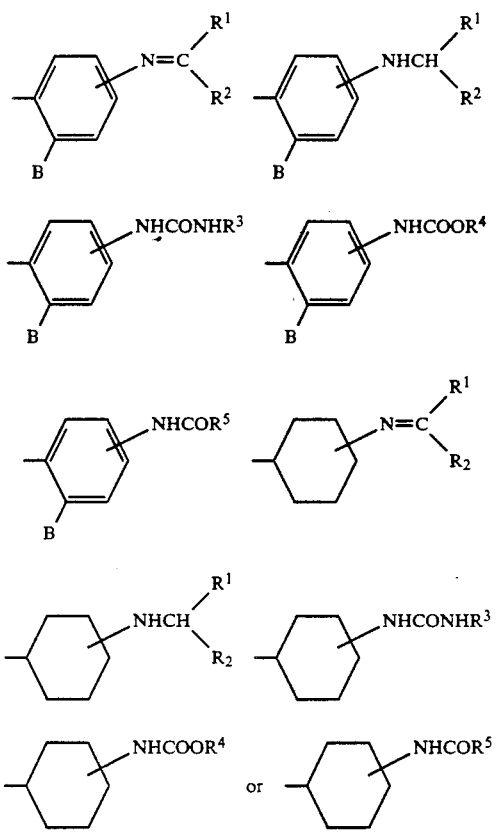

R' is a hydrogen atom, a lower alkyl group having 1 to 5 carbon atoms, a lower hydroxyalkyl group, a lower aminoalkyl group, a phenyl group, a p-hydroxyphenyl group, a benzyl group, a p-hydroxybenzyl group, a 3-methylindole group, or a 5-methylimidazole group; n is from 0 to 5; each of R$^1$ to R$^5$ is a hydrogen atom, an alkyl group, an alkenyl group, an alkynyl group, a phenyl group, a phenyl group mono- or tetra-substituted by an alkyl group having 1 to 4 carbon atoms or a halogen atom, a cyclohexyl group or a cyclohexyl group mono- or tetra-substituted by an alkyl group having 1 to 4 carbon atoms or a halogen atom; B is a hydrogen atom, NH$_2$ or NHCOCF$_3$; and (P) is a phosphoric acid group which is free or protected by a protective group or a pharmaceutically acceptable salt of the inositol derivative. These inositol derivatives may be bonded to a solid phase carrier or conjugated to a protein or polypeptide.

Also described are procedures for preparing salts represented by formula (I) of claim 9 which comprises the steps of previously protecting the hydroxyl group at the 1 position of an inositol-4,5-diphosphoric acid derivative with a silanizing agent, reacting said derivative with a carboxylic acid, preferably on having an amino group or a nitro group, removing the silyl group, phosphorylating the 1 position to produce an inositol-1,4,5-triphosphoric acid derivative in which the 2 position is substituted by a carboxylic ester, reacting this derivative with a reducing agent to produce a salt of an inositol-1,4,5-triphosphoric acid in which the 2 position is substituted by a carboxylic acid substituted by an amino group, and then reducing by reaction of a nitrite and an azido compound, reaction of a nitrite, p-aminoethylphenol and an acid, reaction with an aldehyde, reaction with a ketone, reaction with an isocyanate, reaction with chlorocarbonic ester or reaction with a carboxylic acid.

A preferred aspect of the invention includes novel inositol derivatives represented by formula (II) or (III)

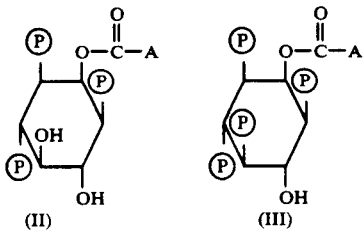

where A is $(CH_2)_nCH(R')NH_2$

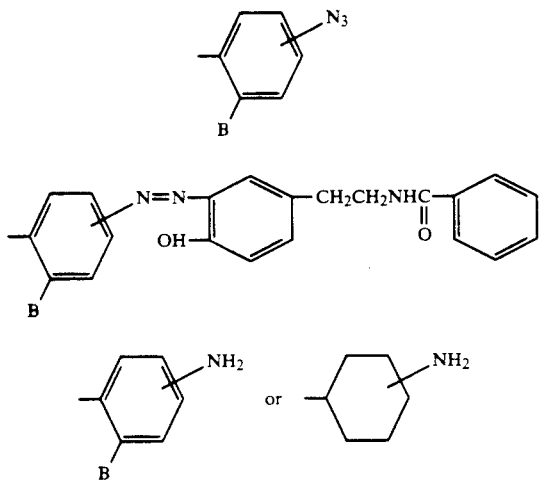

R' is a hydrogen atom, a lower alkyl group having 1 to 5 carbon atoms, a lower hydroxyalkyl group, a lower aminoalkyl group, a phenyl group, a p-hydroxyphenyl group, a benzyl group, a p-hydroxybenzyl group, a 3-methylindole group, or a 5-methylimidazole group; n is from 0 to 5; each of $R^1$ to $R^5$ is a hydrogen atom, an alkyl group, an alkenyl group, an alkynyl group or a phenyl group, a phenyl group mono- or tetra-substituted by an alkyl group having 1 to 4 carbon atoms or a halogen atom, a cyclohexyl group or a cyclohexyl group mono- or tetra-substituted by an alkyl group having 1 to 4 carbon atoms or a halogen atom; B is a hydrogen atom, $NH_2$ or $NHCOCF_3$; (P) is a phosphoric acid group which is free or protected by a protective group or a pharmaceutically acceptable salt of the inositol derivative. These also may be bonded to a solid phase carrier or conjugated to a polypeptide or a protein.

TECHNICAL PROBLEMS AND MEANS FOR SOLVING THEM

According to the present invention, an inositol derivative, particularly an $IP_3$ derivative of the present invention can be synthesized as shown in FIGS. 1 and 2. That is, reaction is carried out on unreacted hydroxyl groups at the 1 and 2 positions of an inositol-4,5-diphosphoric acid derivative in which the hydroxyl groups in the saccharic hydroxyl group and the phosphoric acid residue of an inositol are protected with suitable protective groups, whereby an inositol-1,4,5-triphosphoric acid ($IP_3$) derivative having a kind of substituent at the 2 position. In the concrete, the unreacted hydroxyl group at the 1 position is previously protected with a silanizing agent or the like, and the $IP_2$ derivative having the unreacted hydroxy group at the 2 position is then reacted with a desirable reaction group. In the present invention, a carboxylic ester of the hydroxyl group at the 2 position is exclusively produced. Examples of the carboxylic acid include organic acids such as formic acid, acetic acid, propionic acid, citric acid, fumaric acid and maleic acid, aromatic carboxylic acids such as benzoic acid, naphthalic acid, phthalic acid and quinolinecarboxylic acid, heterocyclic carboxylic acids, organic acids having an amino group such as amino acids, and aromatic carboxylic acids and heterocyclic carboxylic acids having a nitro group. Above all, the various amino acids and p-nitrobenzoic acid can be particularly preferably used. As a reaction medium, there can be used a basic solvent such as pyridine, collidine or picoline. Reaction temperature is from $-20°$ C. to $60°$ C., preferably from $0°$ C. to room temperature. As a reaction accelerator, there can be used a tertiary amine such as 4-dimethylaminopyridine or triethylamine, or cesium fluoride Next, such a protective group as the silyl group at the 1 position of the $IP_2$ derivative is removed therefrom in a suitable solvent, and the 1 position is phosphorylated with a phosphorylating agent in a suitable solvent to produce an $IP_3$ derivative. The reaction begins with $-78°$ C., and the reaction temperature is gradually elevated up to room temperature or so. Afterward, in FIG. 1, a p-nitrobenzoic ester group at the 2 position of a compound 5D is reduced with a suitable reducing agent to become a p-aminobenzoic ester group, and simultaneously, the protective groups which have protected the saccharic hydroxyl group and the phosphoric acid residue are eliminated, thereby obtaining a compound 6D. In case that 4-nitro-2-trifluoroacetylaminobenzoic ester is formed, a compound 6aD' is obtained. In FIG. 2, a similar reducing reaction permits obtaining a compound 12D. These reactions are carried out at $0°-45°$ C., preferably in the vicinity of room temperature, and when the reactions are done for 12 hours in a hydrogen gas flow, the desired compound can be obtained quantitatively. Here, the respective reaction compounds in FIGS. 1 and 2 are represented by a D form, and thus "D" is attached to each compound name. An L form and a DL form can also be subjected to the reactions under the same reaction conditions as in the D form.

A typical compound which can be obtained at this point is 2-O-(4-aminobenzoyl)-1,4,5-tri-O-phosphonomyoinositoltriammonium salt which is a compound 6DL. When the compound 6D is further reacted under various conditions, compounds 7D, 8D, 9D and the like are produced, as shown in FIG. 3. The compounds 6D and 7D are further reacted with activated Sepharose, agarose and Sephadex to produce $IP_3$ derivative-combined solid phase carriers such as compounds 10D and 11D, as shown in FIG. 4. Moreover, the compounds 6D, 7D and 12D can be reacted with various ketones, an aldehyde, an isocyanate, a chlorocarboxylic ester and carboxylic acids to produce compounds 13D, 14D, 15D, 16D and 17D. Reaction conditions in each case are also briefly shown in FIG. 5. In the purification of the compound 6D in FIG. 1 and in the purification of the compound 12D in FIG. 2, a cellulose column chromatography using a water-ammonia-propanol (1:4:5) eluting solvent is utilized to isolate the compounds 6D and 12D, and therefore ammonium salts are produced. Afterward, the thus produced ammonium salts can be dissolved in water, and the resultant solutions can be passed through a cation exchange resin, thereby obtaining sodium salts 6D' and 12D'.

In addition, a reagent can be prepared which can label the bond of $IP_3$ to an enzyme or an acceptor in an organism by the use of a labeled compound For example, a bonded substance of $IP_3$ and biotin or a fluorescent material with the interposition of a suitable spacer can be produced.

According to the present invention, the inositol derivative, particularly the 1,3,4-$IP_3$ derivative or the $IP_4$ derivative of the present invention can be synthesized as follows: As shown in FIGS. 10 and 15, benzyloxymethyl chloride is reacted with 2,4,10-trioxatricyclo-[3,3,1,1$^{3,7}$]decane-6,8,9-triol (102) to synthesize a compound (103), and p-nitrobenzoyl chloride is then acted on this compound (103) to obtain 8-O-benzyloxymethyl-9-O-(4-nitrobenzoyl)-2,4,10-trioxatricyclo[3,3,1,1$^{3,7}$]-decane-6-ol (109). Afterward, this product is reacted with benzyl bromide and then treated with an acidic methanol solution, thereby obtaining 2-O-(4-nitrobenzoyl)-6-O-benzylmyoinositol (111).

The thus obtained compound (111) is reacted with o-xylylenediethyl phosphamidite and m-chloroperbenzoic acid (mCPBA) followed by catalytic hydrogenolysis to obtain myoinositol(1,3,4,5)tetraphosphoric acid (113) having a p-aminobenzoyl group at the 2 position thereof. Reduction is further performed, thereby obtaining myoinositol(1,3,4,5)tetraphosphoric acid (115) having a p-aminocyclohexane group at the 2 position thereof.

With regard to the preparation of a myoinositol(1,3,4,5)tetraphosphoric acid derivative, dibutyltin oxide and methoxymethyl chloride (MOM) are acted on 3,4-p-methoxybenzyl-5,6-dibenzylmyoinositol to protect the 1 position thereof with the MOM group, and the compound is then reacted with a carboxylic acid having a nitro group. Next, the methoxybenzyl group and the MOM group are then eliminated, and the 1, 3, and 4 positions are phosphorylated, followed by reduction, to obtain various carboxylic esters in which the 2 position is esterified, or to obtain a carboxylic ester having a cyclohexane ring (115). Furthermore, as shown in FIGS. 12, 13 and 15, reactions with activated Sepharose, agarose and Sephadex lead to the production of $IP_4$ derivative-bonded solid phase carriers such as substances 114 and 116 as well as a 1,3,4-$IP_3$ derivative-combined solid phase carrier such as a substance 132.

Additionally, according to the present invention, an inositol derivative which is a combined substance of a polypeptide and a protein can be prepared as follows: In case that any of $IP_3$, 1,3,4-$IP_3$ and $IP_4$ is used as a raw material, an aminobenzoyl ester compound (in particular, an amino group is preferably present at the p position) in which the 2 position is esterified is reacted with sodium sulfite at a low temperature, i.e., at 4° C. or less, preferably 0° C. under acidic conditions in an aqueous medium, followed by stirring for a period of from 5 to 30 minutes, preferably from 10 to 20 minutes. In order to get the acidic conditions, concentrated sulfuric acid is preferably used. Next, the resultant reaction solution is neutralized with a 0.1M $NaHCO_3$ solution, and an aqueous solution of a polypeptide and a protein is added thereto and reaction is then carried out at a low temperature, preferably 0° C., for a period of from 10 to 120 hours, preferably from 15 to 96 hours. This reaction solution is transferred to a dialysis membrane vessel, and dialysis is carried out for 3 to 5 days in an aqueous medium in an icebox to purify a reaction product, followed by freeze-drying to obtain a protein-bonded $IP_3$ composite, a protein-bonded 1,3,4-$IP_3$ composite and a protein-bonded $IP_4$ composite. Examples of the various polypeptides and proteins include a bovine serum albumin (hereinafter referred to simply as "BSA"), a human serum albumin (hereinafter referred to simply as "HSA"), a mouse serum albumin (hereinafter referred to simply as "MSA"), an albumen albumin (ovalbumin), collagen and keyhole limpet hemocyanin (KLH). The protein-bonded inositolphosphoric acid compounds which can be manufactured by the above-mentioned procedures allow $IP_3$, 1,3,4-$IP_3$ and $IP_4$ to continuously maintain activity in an organism, and each of these compounds can be administered to the organism orally, by injection or by another means. Furthermore, the protein-bonded inositolphosphoric acid compounds of the present invention can function as hapten-protein composites comprising the carrier protein and $IP_3$, 1,3,4-$IP_3$ and $IP_4$ as the haptens, and it can be considered that they are applied as immunogenicity conjugates.

According to the conventional concept, the protein side is activated in a phosphoric acid buffer solution or the like with 1-ethyl-3-(3-dimethylaminopropyl)carbodiimide.hydrochloride or the like which is a water-soluble carbodiimide series condensation agent, and then reacted with an inositol phosphoric acid compound to bond both the segments mutually, whereby a composite is prepared. However, in using this process, a nucleophilic group present in the protein reacts with a protein-activated site prior to the reaction with the inositol phosphoric acid compound, particularly a 2 position-converted inositol phosphoric acid compound, so that it is difficult to prepare the desired protein-bonded inositolphosphoric acid compounds. On the contrary, the feature of the present invention resides in that the side of the inositolphosphoric acid compound is activated, and in particular, an ester compound of the hydroxyl group at the 2 position of the inositol and a p-aminobenzoylcarboxylic acid is securely reacted with and bonded to the protein in a manner such as diazo coupling or the like to prepare an inositolphosphoric acid-protein composite having an apparent chemical structure. In this case, when the inositolphosphoric acid compound is reacted with the protein, the ratio of these components can be optionally changed, whereby the number of the inositolphosphoric acid compound to be bonded to the protein can be conveniently controlled.

The compounds of formulae (I), (II) and (III) can usually be purified by, for example, a physical process such as crystallization, distillation or chromatography, or for example, a chemical process of forming an alkaline addition salt and then crystallizing this salt, which will be described in detain in the undermentioned reference example and examples.

The compounds of the formulae (I), (II) and (III) as well as their pharmaceutically acceptable salts can exert various pharmacological effects by allowing $Ca^{2+}$ ions to be liberated from vesicles in cells, or preventing the liberation of the $Ca^{2+}$ ions, and they can also exert a therapeutic effect by controlling the cells, the organism or the physiological condition (e.g., the condition of a disease) inherent in the solid. Of the compounds of the formulae (I), (II) and (III), solid phase carrier-bonded compounds are extremely useful to separate and purify proteins which are bonded to or recognize the above-mentioned inositolphosphoric acid compounds, i.e., $IP_3$-5-phosphatase, $IP_3$-3-kinase, 1,3,4-$IP_3$-phosphatase, 1,3,4-$IP_3$-5-kinase, $IP_4$-3-phosphatase, $IP_4$-5-phosphatase, an $IP_3$ acceptor, a 1,3,4-$IP_3$ acceptor and an $IP_4$ acceptor and the like.

The compounds of the formulae (I), (II) and (III) have less toxicity, and most of these compounds have an acute toxicity of 500 mg/kg or more.

In experimental examples, there are exemplified the reactivities of the compounds having the formulae (I), (II) and (III) with the $IP_3$-5-phosphatase, the $IP_3$-3-kinase, the 1,3,4-$IP_3$-phosphatase, the 1,3,4-$IP_3$-5-kinase, the $IP_4$-3-phosphatase, the $IP_4$-5-phosphatase and the like, their liberation abilities of $Ca^{2+}$ ions from vesicles, their reactivities with the $IP_3$-bonded protein (acceptor), the 1,3,4-$IP_3$-bonded protein (acceptor), the $IP_4$-bonded protein (acceptor) and the like.

The inositol derivative compounds of the formulae (I), (II) and (III) as well as their pharmaceutically acceptable salts can be mixed or combined with suitable carriers for medicines such as distilled water, glucose, lactose, starch, cellulose, magnesium stearate, talc, gum arabi, lecithin and ribosome to prepare medicinal compositions, and these compositions can be fed and applied to patients and animals.

Each of these medicinal compositions contains 0.1 mg to 200 mg of an effective component per unit agent. Furthermore, each medicinal composition can be administered to patients and animals once to 6 times per day orally or through the rectum or parenterally in the form of tables, capsules, suppositories, injections, drinks, transnasal agents, eyewashes or the like.

Now, the present invention will be described in detail in reference to a reference example, examples and experimental examples, but the present invention should not be limited thereto.

REFERENCE EXAMPLE 1

A method for preparing a compound 1D will be quoted and described briefly

In the above-mentioned Japanese Patent Laid-open No. 63-198642, a compound 3 produced in Example 1 (1,2-cyclohexylidene-3,5-di-O-benzyl-myoinositol)

↓ a compound 14 produced in Example 17 [3,6-dibenzyl-4,5-bis(dibenzylphospho)-1,2-cyclohexylidene-myoinositol].

↓ a compound 15 produced in Example 18 [3,6-dibenzyl-4,5-bis(dibenzylphospho)-myoinositol] which corresponds to 1DL.

Of the compounds of the formula (I), the typical compounds are compounds 6D and 6D' of a synthetic route 1, compounds 12D and 12D' of a synthetic route 2, compounds 7D and 7D', compounds 8D and 8D', and compounds 9D and 9D' of a synthetic route 3, compounds 10D' and 11D' of a synthetic route 4, and compounds 13D', 14D', 15D' and 16D' of a synthetic route 5. The typical compounds having a D form will be enumerated as follows. In this connection, compounds having an L form can be represented by replacing the first "D" with "L" of each of the following compounds, and racemic modifications can be represented by removing the first "D" of each compound therefrom.

| | |
|---|---|
| 1D: | 1D-3,6-di-O-benzyl-4,5-di-O-dibenzylphosphoryl-myoinositol |
| 2D: | 1D-3,6-di-O-benzyl-4,5-di-O-dibenzylphosphoryl-1-O-triethylsilyl-myoinositol |
| 3D: | 1D-3,6-di-O-benzyl-4,5-di-O-dibenzylphosphoryl-2-(4-nitrobenzoyl)-1-O-triethylsilylmyoinositol |
| 4D: | 1D-3,6-di-O-benzyl-4,5-di-O-dibenzylphosphoryl-2-O-(4-nitrobenzoyl)myoinositol |
| 5D: | 1D-3,6-di-O-benzyl-1,4,5-tri-O-dibenzylphosphoryl-2-O-(4-nitrobenzoyl)myoinositol |
| 6D: | 1D-2-O-(4-aminobenzoyl)-1,4,5-tri-O-phosphonomyoinositol triammonium salt |
| 6D': | 1D-2-O-(4-aminobenzoyl)-1,4,5-tri-O-phosphonomyoinositol trisodium salt |
| 7D: | 1D-2-O-(4-aminocyclohexanecarbonyl)-1,4,5-tri-O-phosphonomyoinositol triammonium salt |
| 8D: | 1D-2-O-(4-azidobenzoyl)-1,4,5-tri-O-phosphonomyoinositol triammonium salt |
| 9D: | 1D-2-O-[4-(5-acylaminoethyl-2-hydroxyphenylazo)-benzoyl]-1,4,5-tri-O-phosphonomyoinositol triammonium salt |
| 10D: | 1D-2-O-[4-(5-aminoethyl-2-hydroxyphenylazo)benzoyl]-1,4,5-tri-O-phosphonomyoinositol triammonium salt (Sepharose 4B) |
| 11D: | 1D-2-O-(4-aminocyclohexanecarbonyl)-1,4,5-tri-O-phosphonomyoinositol triammonium salt (Sepharose 4B) |

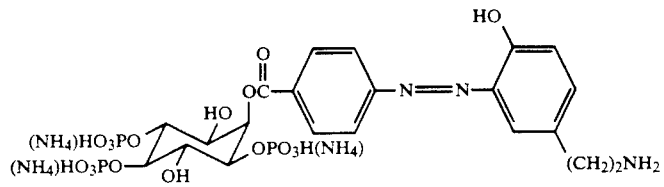

The compound 10D can be expressed as the combination of the amino group of the above-mentioned compound and Sepharose.

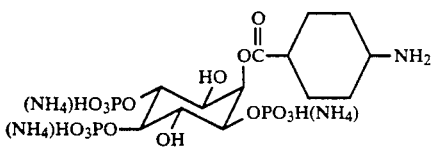

The compound 11D can also be considered to be the combination with the above-mentioned amino group.

BRIEF DESCRIPTION OF THE DRAWINGS

In FIG. 3, compounds in which $NH_4$ of each of the compounds 6D, 7D, 8D and 9D is replaced with Na can be represented with compounds 6D', 7D', 8D' and 9D', and in FIG. 5, the compounds 6D', 7D' and 12D' are abbreviated to $RNH_2$, and the portion corresponding to $NH_2$ of each compound is indicated by a wave line and the other portion is represented by R.

EXAMPLES

Example 1

Figure 1:
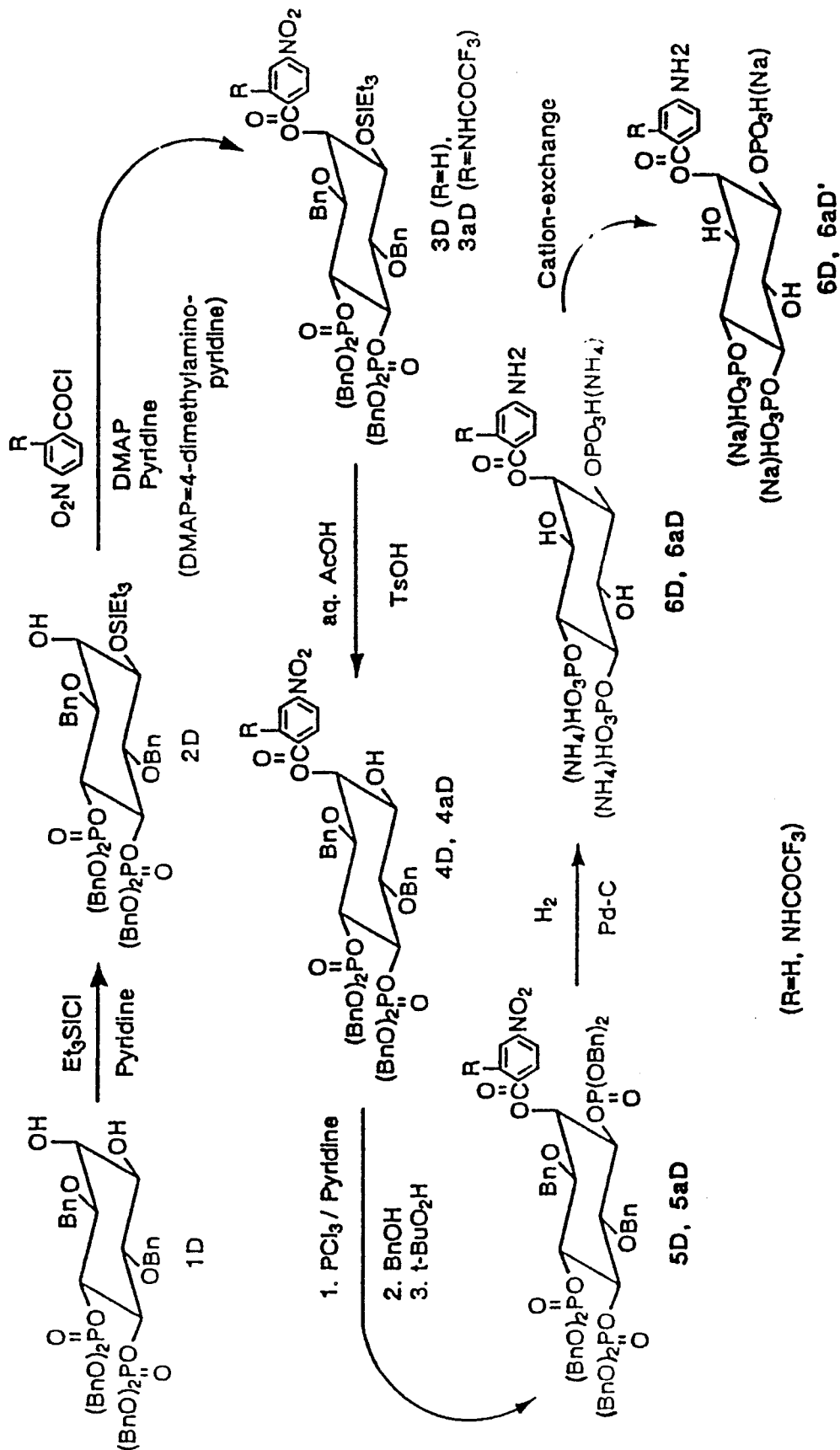
FIG. 1 shows a synthetic route 1.
Figure 2:
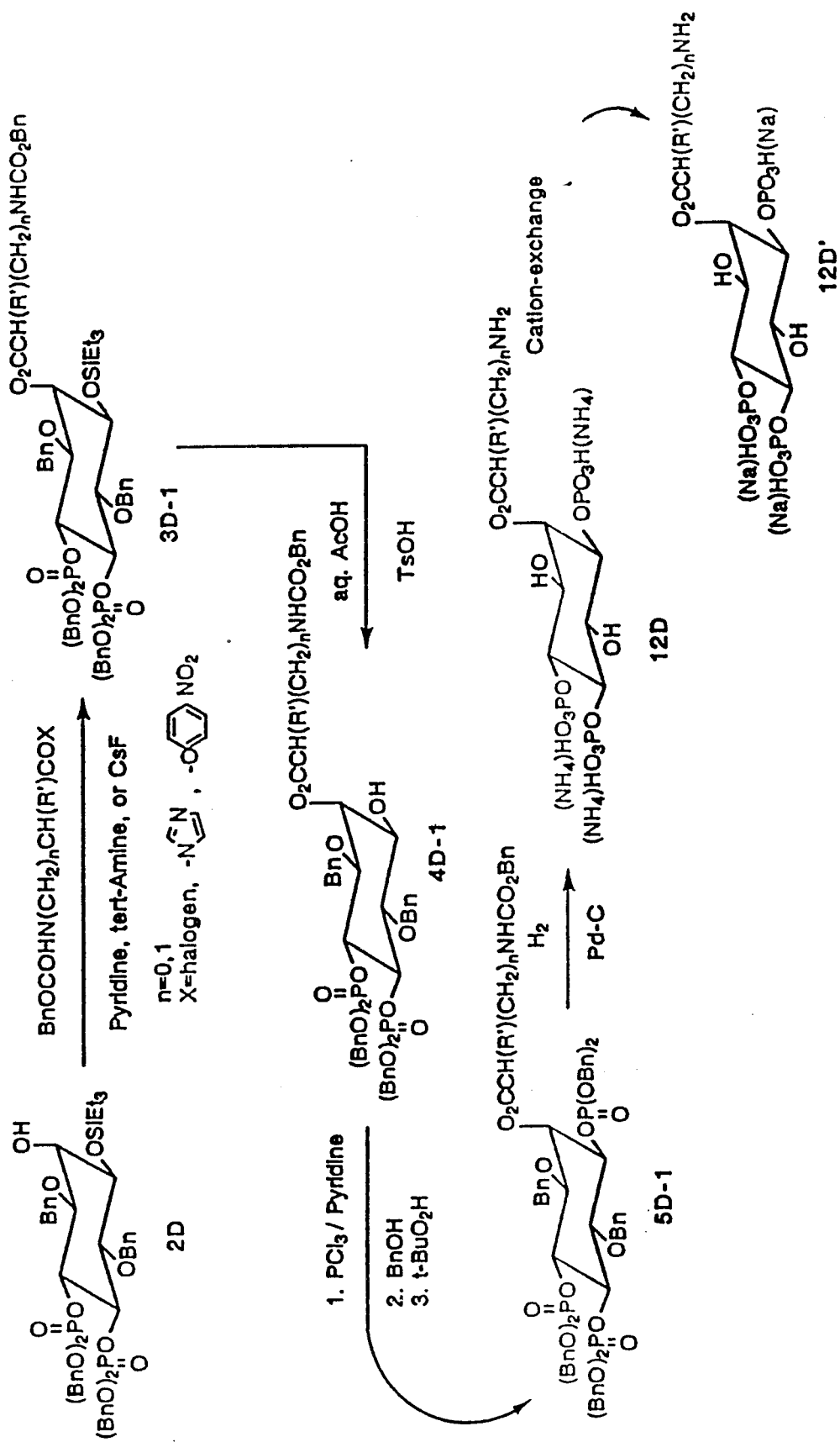
FIG. 2 shows a synthetic route 2.
Figure 3:
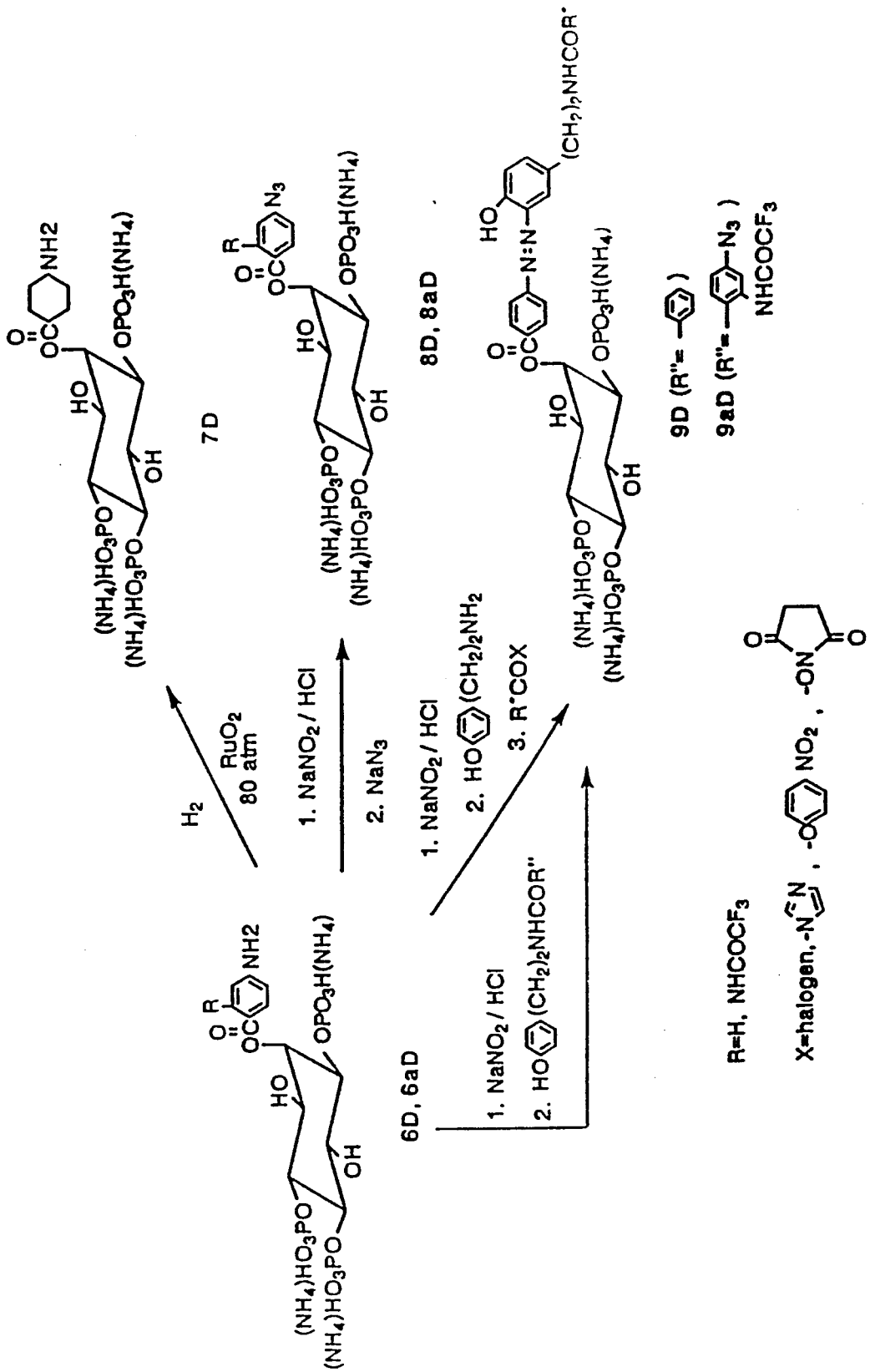
FIG. 3 shows a synthetic route 3.
Figure 4:
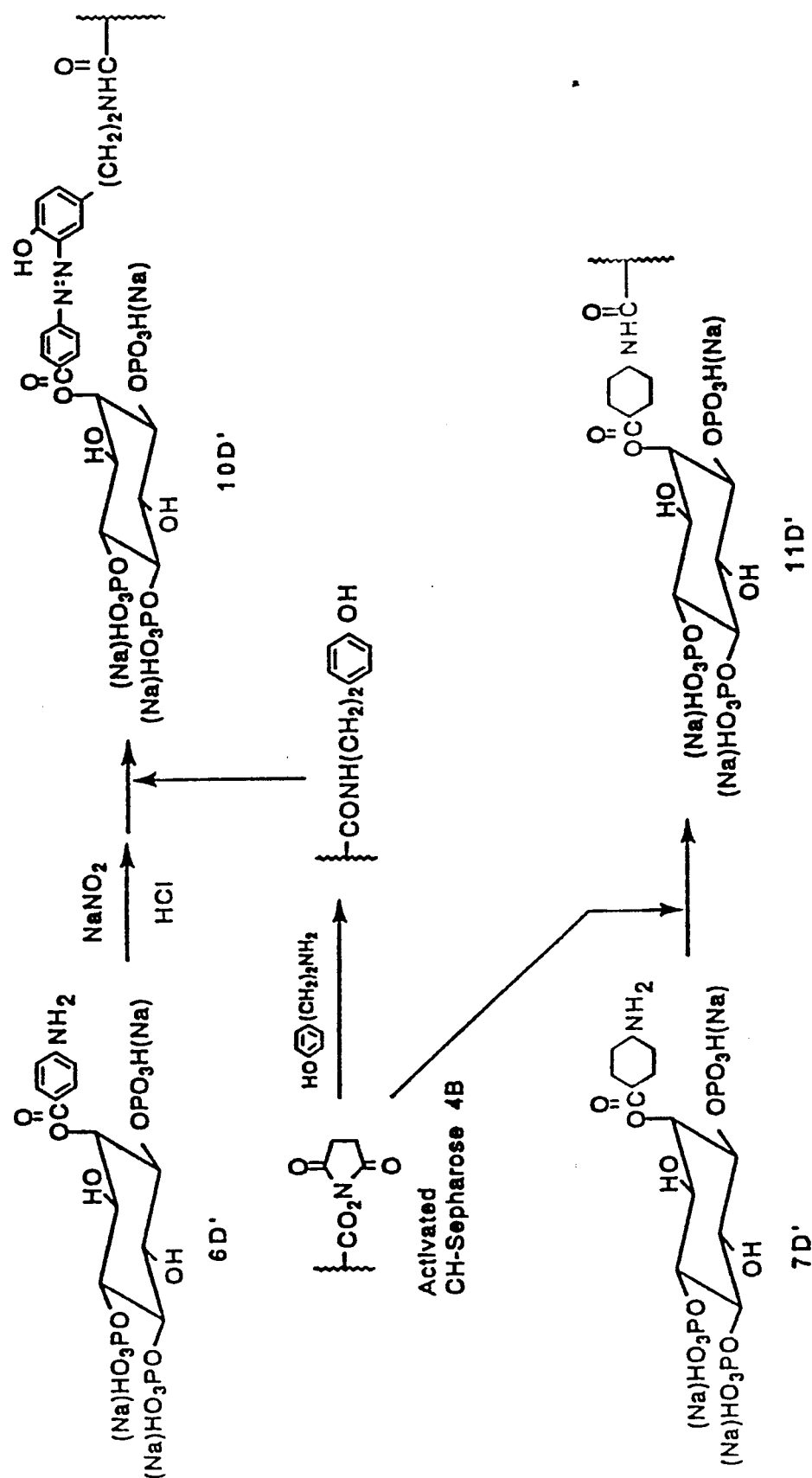
FIG. 4 shows a synthetic route 4.
Figure 5:
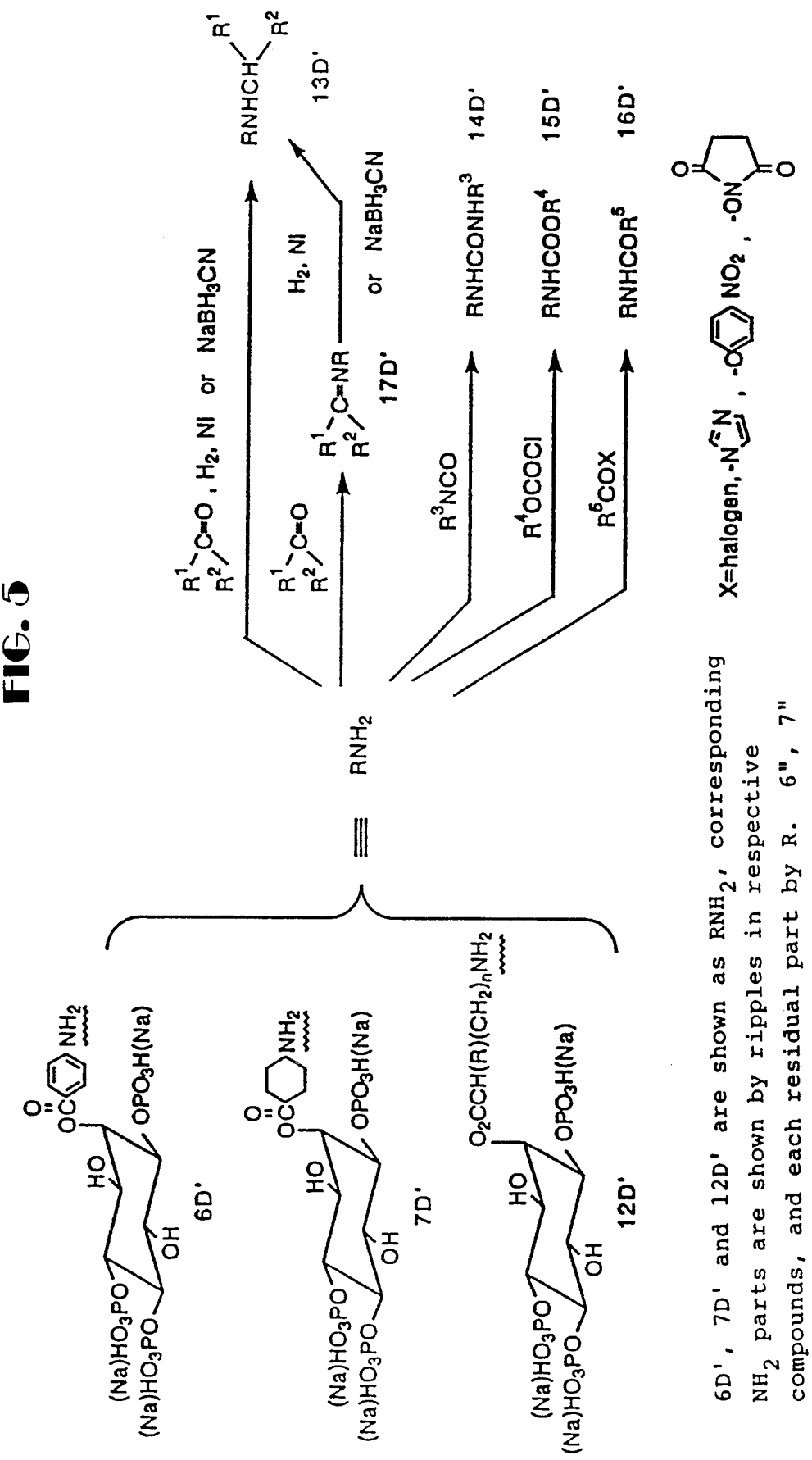
FIG. 5 shows a synthetic route 5.

Optical resolution of DL-3,6-di-O-benzyl-4,5-di-O-dibenzylphosphorylmyoinositol with Chiral Cell OD

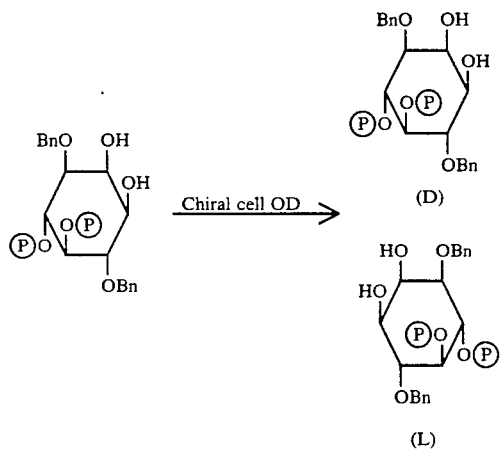

200 mg of DL-3,6-di-O-benzyl-4,5-di-O-dibenzylphosphorylmyoinositol was subjected to optical resolution by the use of Chiral Cell OD (for separation).

Eluting solvent: n-Hexane 5: i-PrOH 1
Flow rate: 10 ml/min
Pressure: 18 atm
Charge weight: 20–30 mg $[\alpha]_D^{23} = -21.0°$ 10–15 mg was obtained (C=1.10, $CHCl_3$).

$[\alpha]_D^{23} = +21.0°$ 10–15 mg was obtained. (C=1.05, $CHCl_3$).

$^1$H-NMR ($CDCl_3$, 270 MHz) δ 2.4–2.5 (br 2H —OH), 3.47 (dd 1H $H_3$), 3.53 (dd 1H $H_1$), 3.88 (t 1H $H_6$), 4.08 (t 1H $H_2$), 4.52 (d 1H —CH—$OCH_2Ph$), 4.50 (ddd 1H $H_5$), 4.61 (d 1H —$COCH_2Ph$), 4.74 (d 1H $COCH_2Ph$), 4.85 (d 1H —CO—$CH_2Ph$), 4.71–5.08(m 9H $\overset{\overset{\displaystyle O}{\|}}{P}OCH_2Ph \times 8, H_4$)

7.03–7.35 (Ar 30H).

IR (nujol) 3450, 1236, 1120, 980, 880, 703, 667 $cm^{-1}$.

Example 2

Preparation of a compound 2

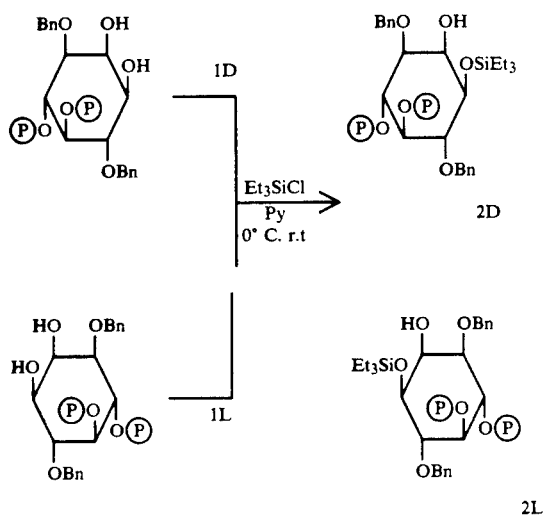

74 mg of D-1,2-diol and 70 mg of L-1,2-diol were separately placed in reaction vessels and then separately subjected to the following operation. An azetropic point was reached about 3 times with anhydrous pyridine. 3 ml of anhydrous pyridine was added to the resultant residue, and the solution was then cooled to 0° C. in an $N_2$ gas flow. 0.019 g (1.5 eq.) and 0.018 (1.5 eq.) of triethylsilyl chloride were separately added dropwise. After the addition, reaction was carried out at room temperature for 3 hours. After completion of the reaction, pyridine was distilled off under reduced pressure, and the resultant residue was extracted with ethyl acetate and then washed with water 3 times, a saturated $KHSO_4$ solution twice, water, a saturated $NaHCO_3$ solution once and water. Afterward, the solution was dried over sodium sulfate, and the solvent was then distilled off under reduced pressure. The residue was purified by a column chromatography, and compounds 2D and 2L were obtained in yields of 86% and 85%, respectively.

$^1$H-NMR ($CDCl_3$, 270 MHz), δ 0.46–0.57 (m 6H —$CH_2CH_3$x3), 0.83 (t 9H —$CH_2CH_3$x3), 2.35–2.45 (br 1H —OH), 3.42 (dd 1H $H_3$), 3.53 (dd 1H $H_1$), 3.70 (dd 1H $H_2$), 3.8 (t 1H $H_6$),

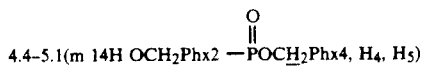

4.4–5.1(m 14H $OCH_2Phx2$ —$POCH_2Phx4$, $H_4$, $H_5$)

7.0×7.2 (m 30H Ar).
IR (nujol) 3400, 1568, 1229, 1082, 880, 640 cm$^{-1}$.

Example 3

Preparation of a compound 3

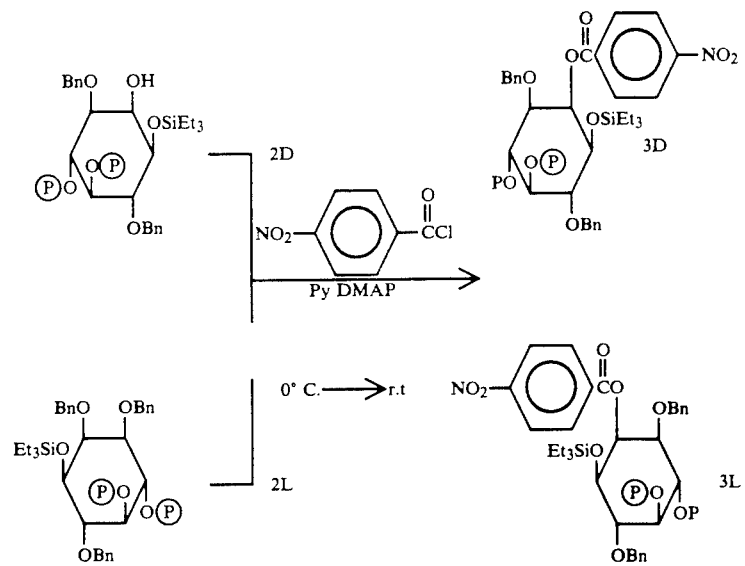

52.9 mg of D-2-monool and 49.4 mg of L-2-monool were separately sampled, and both the samples were separately subjected to the following operation, as in Example 2. An azetropic point was reached about 3 times with anhydrous pyridine. 3 mml of anhydrous pyridine was added to the resultant residue, and the solution was then cooled to 0° C. in an N₂ gas flow. 0.197 g (20 eq.) and 0.184 (20 eq.) of p-nitrophenylcarbonyl chloride were separately added. Successively, a Example 4

Preparation of a compound 4

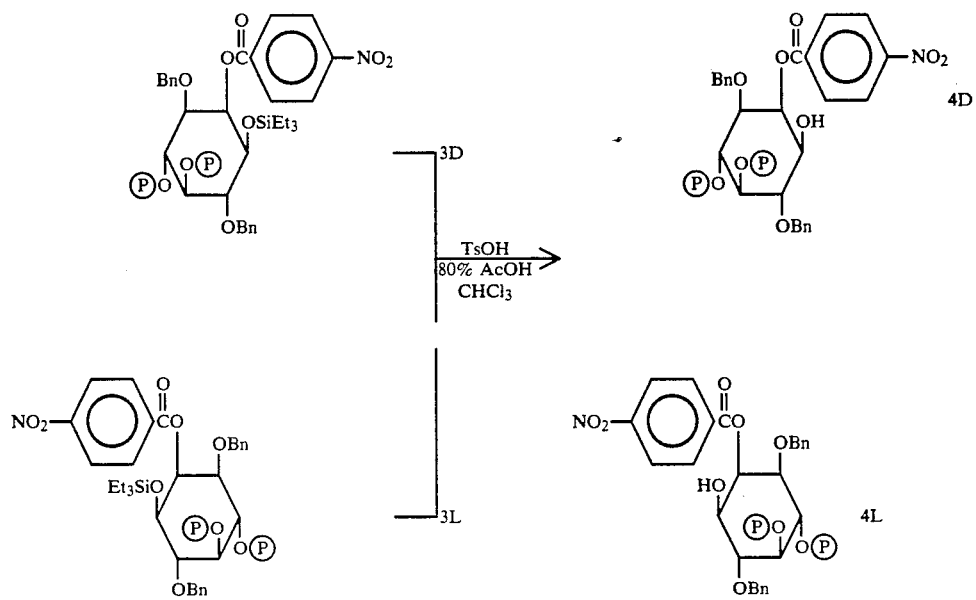

catalytic amount of dimethylaminopyridine was added, and reaction was then carried out overnight at a temperature of from 0° C. to room temperature. After completion of the reaction, pyridine was distilled off under reduced pressure, and the resultant residue was extracted with ethyl acetate and then washed with water, a saturated KHSO₄ solution, water, a saturated NaHCO₃ solution and water. Afterward, the solution was dried over sodium sulfate, and the solvent was then distilled off under reduced pressure. The residue was subjected to a column chromatography, so that compounds 3D and 3L were obtained in yields of 92% and 92%, respectively.

¹H-NMR (CDCl₃, 270 MHz), δ 0.26–0.57 (m 6H —CH₂CH₃x3), 0.83 (t 9H —CH₂CH₃x3), 3.67 (dd 1H H₃), 3.83 (dd 1H H₁), 3.93 (t 1H H₆), 4.5~5.1 (m 14H H₄, H₅, —OCH₂Ph×2.

55 mg of D-2-acyl substance and 52 mg of L-2-acyl substance were separately dissolved in 1 ml of chloroform, and 3 ml of 80% acetic acid, each of 23 mg (2.5 eq.) and 21 mg (2.5 eq.) of paratoluenesulfonic acid was added at room temperature. After reaction for 3 hours, extraction was carried out with ethyl acetate, followed by washing with water, a saturated NaHCO₃ solution and water. Next, drying over sodium sulfate and concentration were carried out, and the resultant residue was purified by a column chromatography. Compounds 4D and 4L were obtained in yields of 91% and 92%, respectively.

¹H-NMR (CDCl₃, 270 MHz), δ 3.7 (dd 1H H₃), 3.8 (dd 1H H₁), 3.9 (t 1H H₆), 4.5–5.1 (m 14H H₄, H₅, —OC$\underline{H}_2$Phx2, —$\overset{\text{O}}{\overset{\|}{\text{P}}}$OC$\underline{H}_2$Phx4)

5.75 (t 1H H₂), 7.03–7.38 (m Ar 30H),

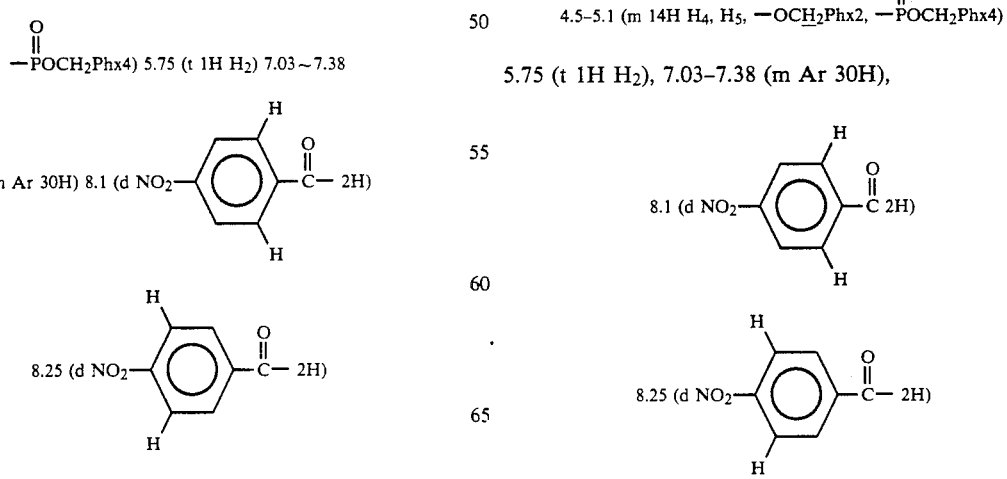

IR (nujol) 1700 cm⁻¹.

Example 5

Preparation of a compound 5

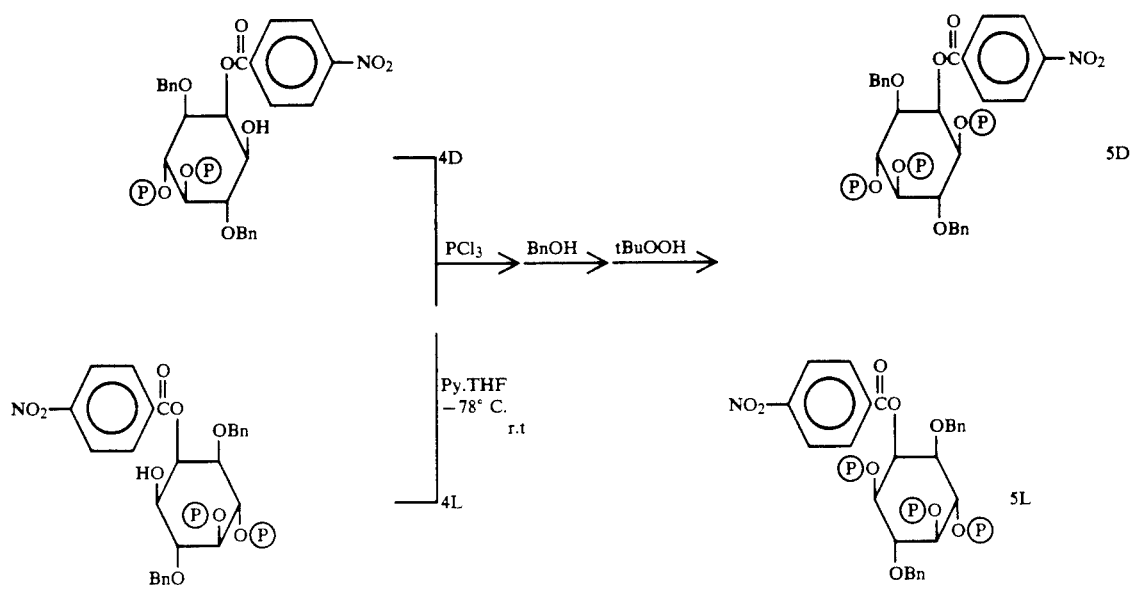

45.3 mg of D-1-monool and 42.3 mg of L-1-monool were separately sampled, and 3 ml of anhydrous THF and 0.5 ml of anhydrous pyridine were added. The solution was then cooled to −78° C. in an $N_2$ gas flow. Afterward, 12 mg (2 eq.) and 11 mg (2 eq.) of phosphorus trichloride were separately added. After reaction was carried out for 1 hour, 28 mg (6 eq.) and 27 mg (6 eq.) of benzyl alcohol were separately added at −78° C. After 1 hour's reaction, 16 mg (4 eq.) and 15 mg (4 eq.) of t-butyl hydroperoxide were added at −78° C., and then reaction temperature was gradually elevated to room temperature. After reaction for a period of 1 to 2 hours, extraction was carried out with ethyl acetate, followed by washing with water, a saturated $KHSO_4$ solution, water, and a saturated $NaHCO_3$ solution and water. Next, drying over sodium sulfate and concentration were carried out, and the resultant residue was purified by a column chromatography to obtain compounds 5D and 5L in yields of 80% and 81%, respectively.

$^1$H-NMR ($CDCl_3$, 270 MHz), δ 3.7 (dd 1H $H_3$), 4.1 (dd 1H $H_6$), 4.6~5.1 (m 19H, $H_1$, $H_4$, $H_5$, —$OCH_2Ph \times 2$.

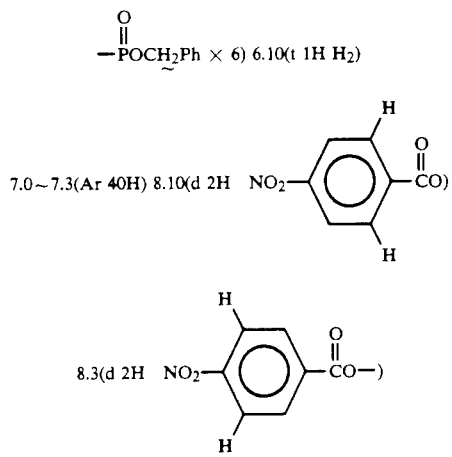

Example 6

Preparation of a compound 6

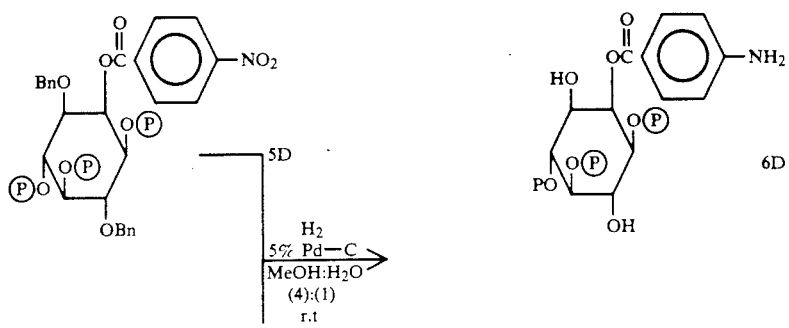

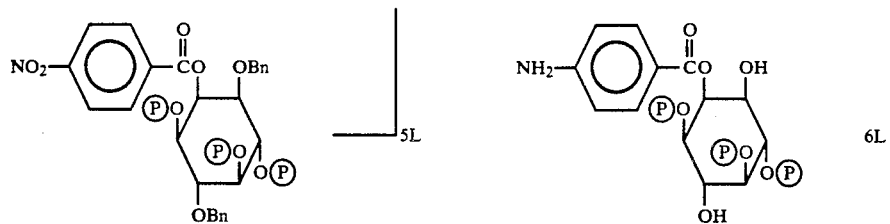

46.5 mg of a D form and 42.5 mg of an L form were separately dissolved in 5 ml of an MeOH (4):H₂O (1) solution. 50 mg of 5% Pd-C was added to each solution, and reaction was carried out under 1 atm for 12 hours in a hydrogen gas flow. After completion of the reaction, the catalyst was removed by filtration, and the solvent was then stilled off under reduced pressure. The resultant residue was purified by a cellulose column chromatography by the use of water-ammonia-n-propanol (1:4:5) as an eluting solvent to isolate compounds 6D and 6L quantitatively (ammonium salts).

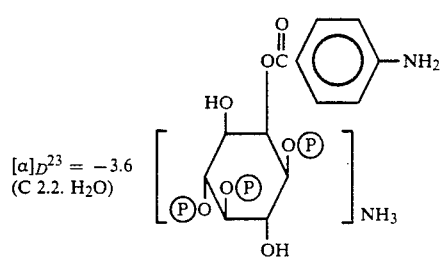

$[\alpha]_D^{23} = -3.6$
(C 2.2. H₂O)

$[\alpha]_D^{23} = +4.2$
(C 2.13 H₂O)

mp > 280°

Example 7

Conversion from a compound 6D (6L) to a compound 6D' (6L'):

Each of the thus obtained ammonium salts was converted into a sodium salt. A 10% pyridine solution was passed through cation exchange resin DOWEX 50W-X2 (H⁺ type) to convert into a pyridine form. Afterward, an ammonium salt of the inositol was passed through this resin to convert into a pyridinium salt of the inositol.

A 10% NaOH solution was passed through the cation exchange resin to convert into an Na⁺ form. A pyridinium salt of the inositol was passed through the resin to convert into a sodium salt of the inositol.

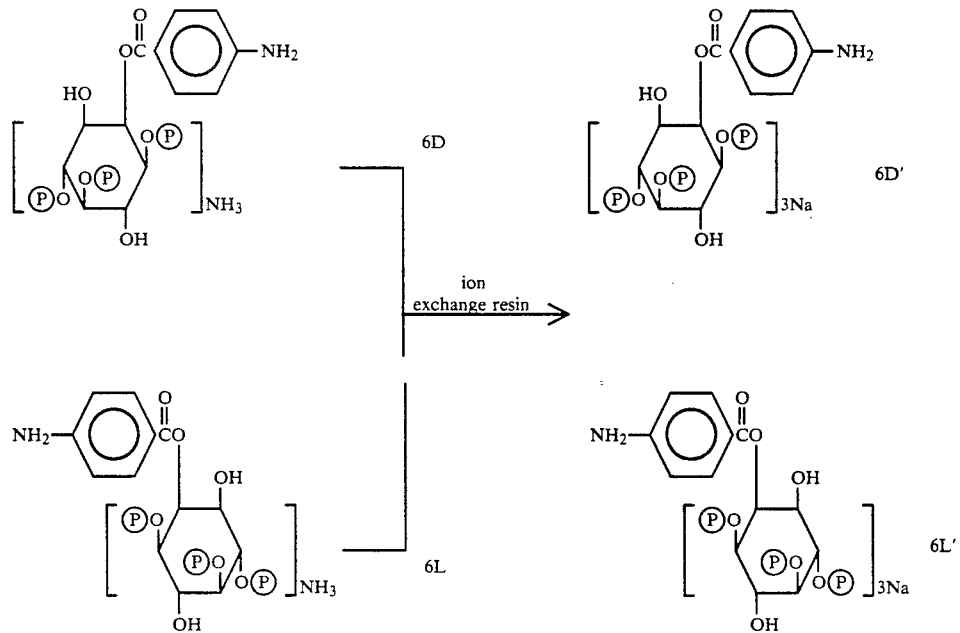

The above-mentioned compounds 6D', 6L' were obtained quantitatively.

$^1$H-NMR (D$_2$O 270 MHz), δ 3.8 (dd 1H H$_3$), 3.9 (br 2H H$_5$, H$_6$), 4.1 (br 1H H$_4$), 4.25 (br 1H H$_4$), 5.65 (t 1H H$_2$),

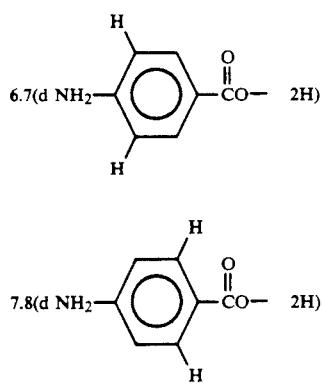

IR KBr method, 3350, 1680, 1600, 1280, 1040, 920 cm$^{-1}$.

m.p. 280° C. or more.

Example 8

Preparation of a sodium salt 6DL' of optically inactive 6DL 70 mg of a DL form (5DL) was dissolved in 5 ml of MeOH (4):H$_2$O (1), and 100 mg of 5% Pd-C and 70 mg of AcONH$_4$ were added. Afterward, reaction was carried out for 12 hours under atmospheric pressure. The 5% Pd-C was removed by filtration, and water was then distilled off under reduced pressure. The resultant residue was subjected to a cellulose column isolation treatment to obtain a compound 6DL quantitatively.

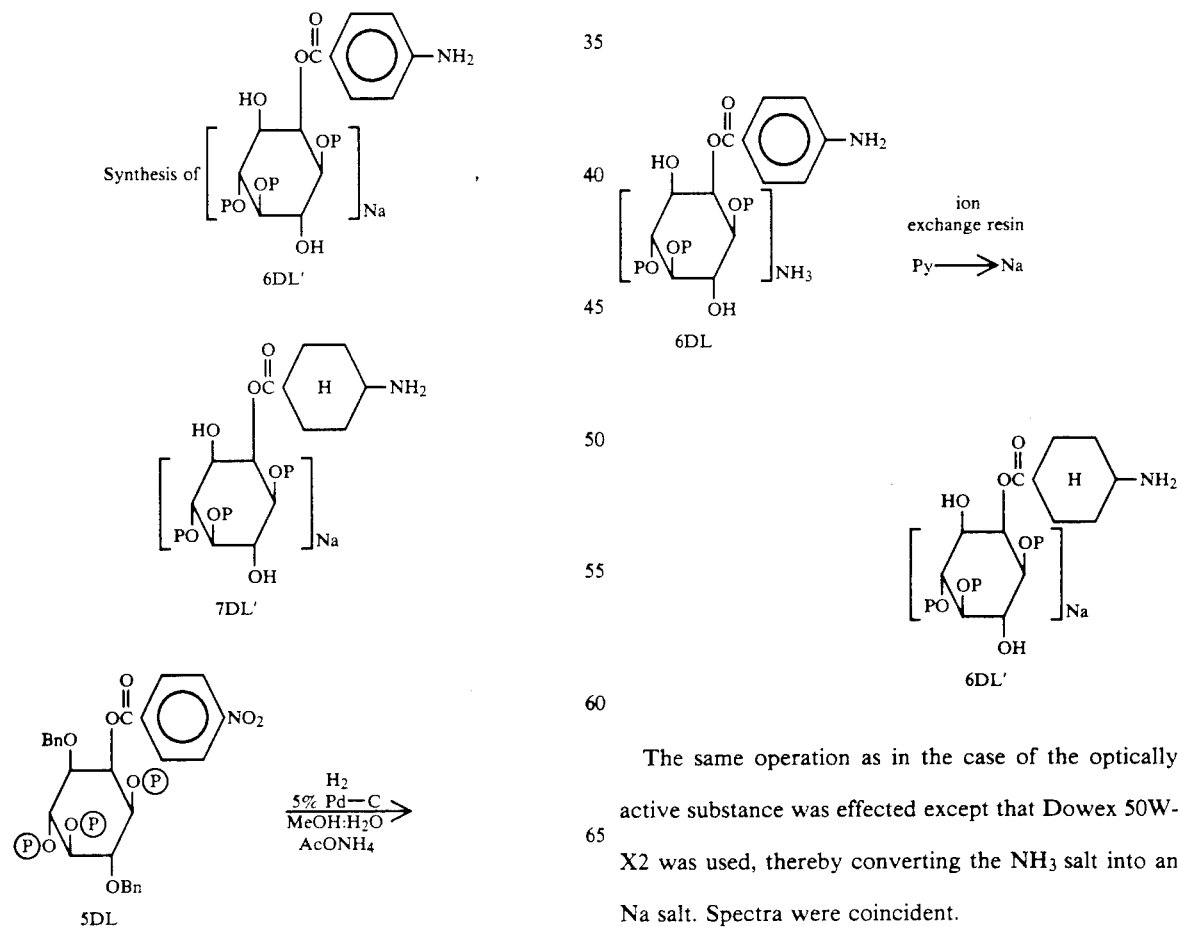

The same operation as in the case of the optically active substance was effected except that Dowex 50W-X2 was used, thereby converting the NH$_3$ salt into an Na salt. Spectra were coincident.

Example 9

Preparation of a compound 7

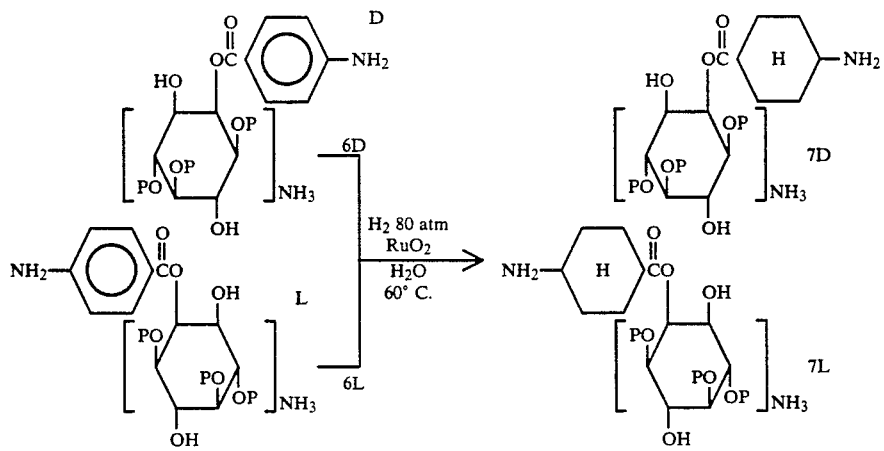

10 mg of 6D and 9 mg of 6L were separately dissolved in 5 ml of water, and 10 mg of ruthenium oxide was added to each solution and reaction was then carried out at 60° C. for a period of from 2 to 3 hours under 80 atm of hydrogen in an autoclave. The catalyst was removed by filtration, and water was then distilled off under reduced pressure. Afterward, the resultant residue was treated with DOWEX 50W-X2 (cation exchange resin) to convert the ammonium salt into a sodium salt. In consequence, a compound 7D and a compound 7L were obtained in yields of 90% and 95%, respectively.

$[\alpha]_D^{23} = -4.9$ (C 0.92 H$_2$O)    7D'

$[\alpha]_D^{23} = +5.6$ (C 0.53 H$_2$O)    7L'

Melting points of both the compounds were 280° C. or more.

$^1$H-NMR (D$_2$O 270 MHz)

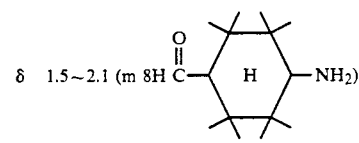

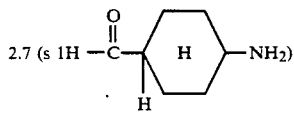

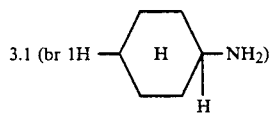

3.8 ~ 4.2 (m 5H H$_1$, H$_3$, H$_4$, H$_5$, H$_6$), 5.6 (t 1H H$_2$).

Example 10

Preparation of a sodium salt 7DL' of an optically inactive compound 7DL

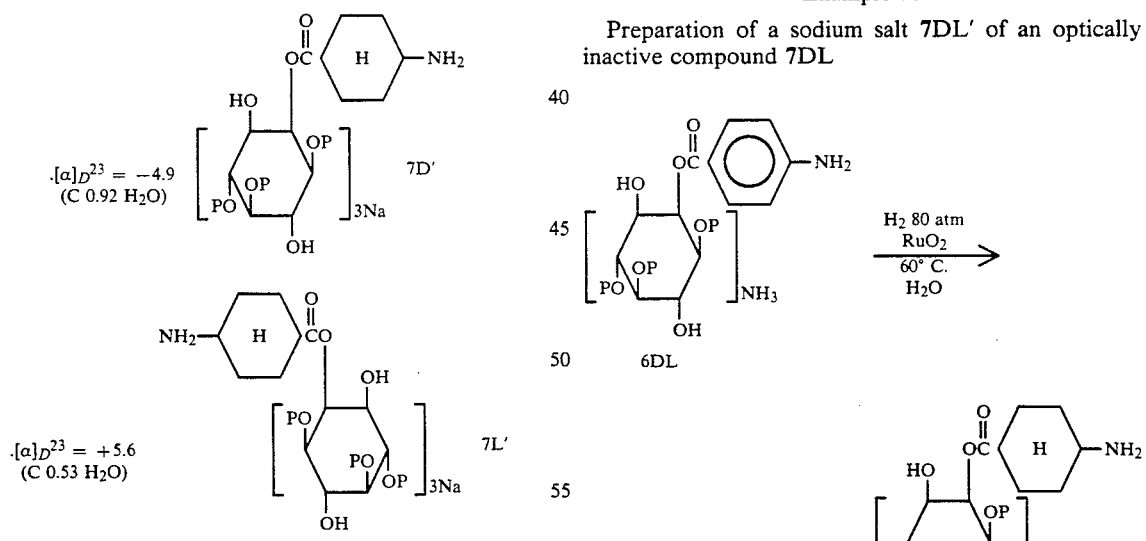

20 mg of a compound 6DL was dissolved in 5 ml of water. Next, ruthenium oxide was added, and a hydrogen pressure was raised up to 80 atm in an autoclave and reaction was then carried out at 60° C. for 2 hours. The catalyst was removed by filtration and water was then distilled off under reduced pressure, and the resultant residue was passed through an ion exchange resin to obtain a compound 7DL' quantitatively.

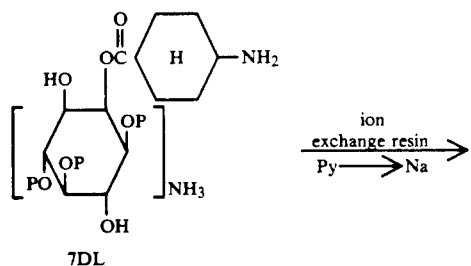

7DL

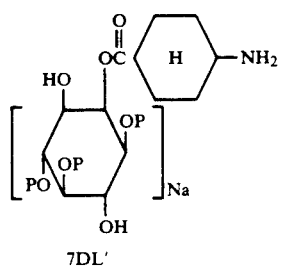

7DL'

DOWEX 50W-X2 was used to convert the ammonium salt into a sodium salt. Spectra were coincident.

Example 11

Preparation of compounds 8 and 8a

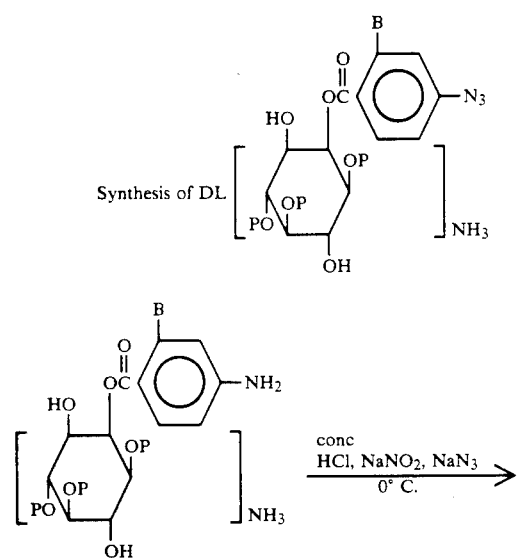

6DL (B = H), 6aDL (B = NHCOCF$_3$)

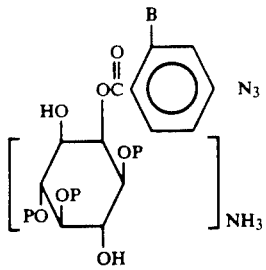

8DL (B = H), 8aDL (B = NHCOCF$_3$)

30 mg of a compound 6DL was dissolved in 3 ml of water, and 0.1 ml of concentrated hydrochloric acid was added. The solution was cooled to 0° C. While the solution was stirred, a solution of 10 mg of sodium nitrite and 0.5 ml of water was added dropwise. After stirring for 1 hour, blue violet was confirmed by a potassium iodide starch test paper, and 7 mg of sodium azide was then added. After reaction for 1 hour, the solvent was distilled off under reduced pressure, and a product was isolated through a cellulose column quantitatively.

$^1$H-NMR (D$_2$O 270 MHz) δ 3.7 (dd 1H H$_3$), 3.8 (br 2H H$_1$, H$_6$), 3.9 (br 1H H$_5$), 4.2 (br 1H H$_4$), 5.6 (s 1H H$_2$),

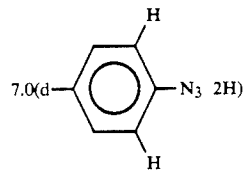

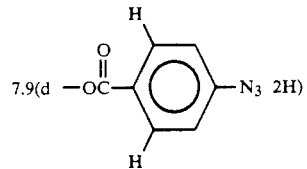

IR (KBr method) 3200, 2100, 1700, 1600, 1400, 1260, 1100 cm$^{-1}$.

A compound 8a was also synthesized by all the same procedure as above.

IR (Nujol) 3200, 2100, 1750, 1700 cm$^{-1}$.

Example 12

Preparation of compounds 9 and 9a

Synthesis of

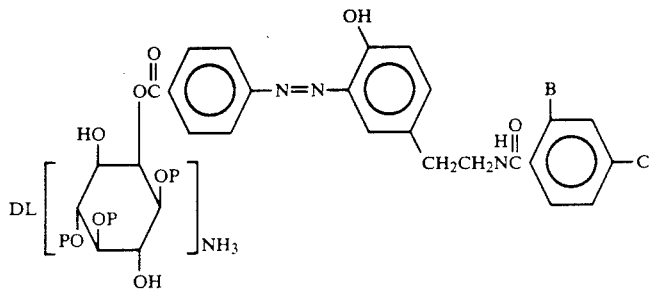

9DL (B = C = H) .9aDL (B = NHCOCF₃.C = N₃)

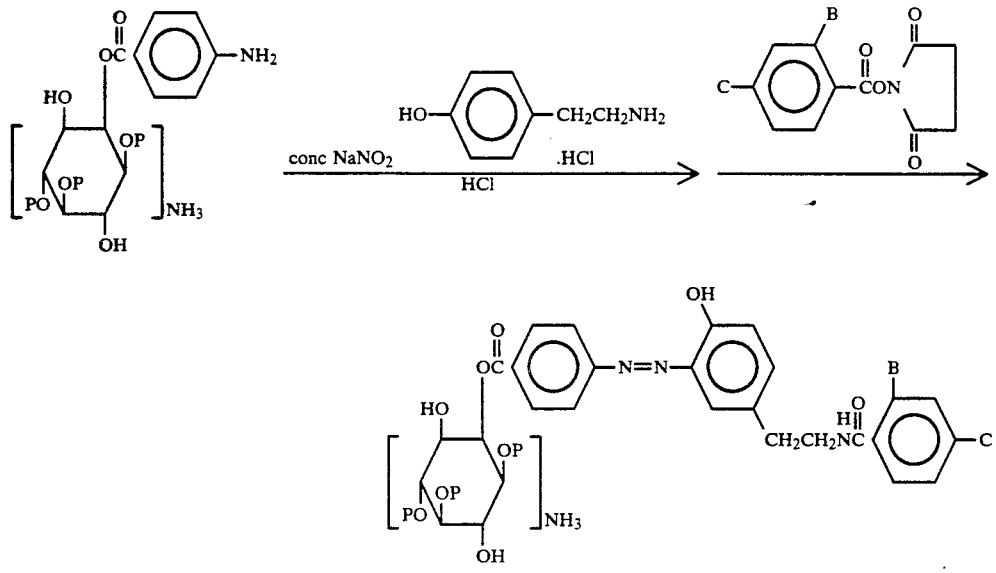

9DL(B = C = H).9aDL(B = NHCOCF₃.C = N₃)

30 mg of a raw material was dissolved in 3 ml of water, and 50 μl of concentrated hydrochloric acid was then added. The solution was cooled to 0° C., and while it was stirred, a solution of 10 mg of sodium nitrite and 0.5 ml of water was added dropwise. After stirring for 1 hour, blue violet was confirmed by a potassium iodide starch test paper, and 13.2 mg of tyramine.hydrochloride was then added. After reaction for 2 hours, excess tyramine was removed by separation, and an aqueous layer was distilled off under reduced pressure. A residue was isolated through a cellulose column, and the product was dissolved in 2 ml of a DMF/water solution and then reacted with N-hydroxylsuccinimide ester (benzoic ester). After reaction for 2 hours, the reaction solution was distilled off under reduced pressure, and the resultant residue was then subjected to a cellulose column isolation treatment to obtain a product in a yield of 20% in all.

¹H-NMR (D₂O 270 MHz)

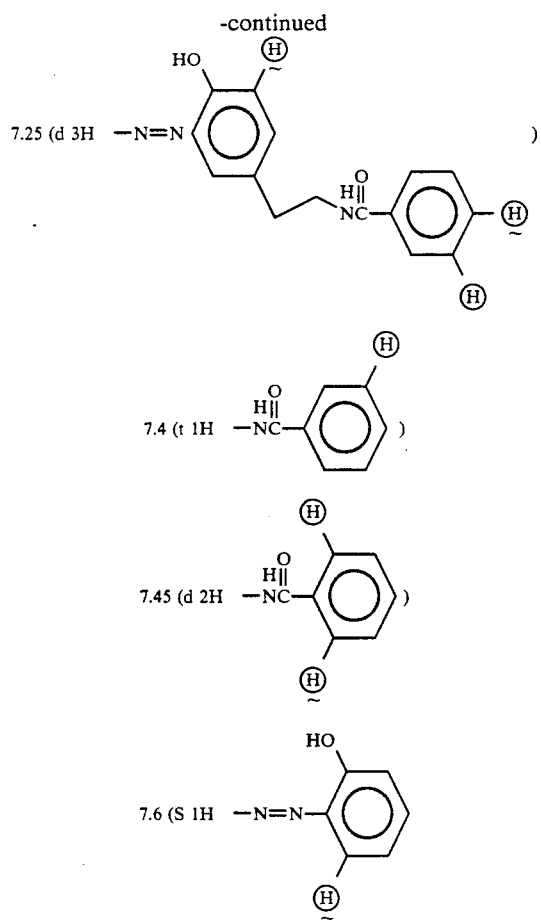

3.9 (d 1H H₃), 4.0 (br 2H H₅, H₆), 4.15 (br 1H H₁), 4.35 (br 1H H₄), 5.8 (s 1H H₂),

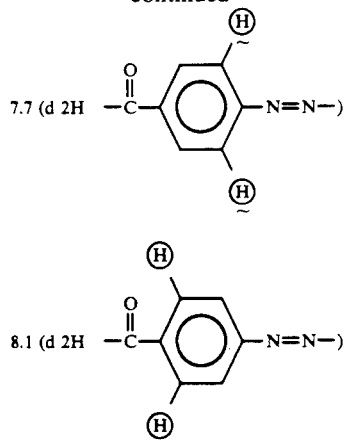

7.7 (d 2H) —C(=O)—[benzene ring with (H), (H)]—N=N—

8.1 (d 2H) —C(=O)—[benzene ring with (H), (H)]—N=N—

The compound 9aDL was also synthesized by all the same operation as above.

IR (Nujol) 3200, 2100, 1745, 1650 cm$^{-1}$.

Example 13

Preparation of a compound 10

On a glass filter (G3), 1 g of a gel was swelled and washed by the use of 200 ml of 1 mM HCl. 3 mg of a compound 7D

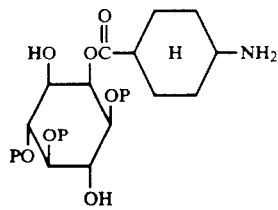

was dissolved in 6 ml of a coupling buffer (0.1M of $NaHCO_3$, pH 8.0). The gel was rapidly washed with this buffer. The gel suspension and a ligand solution were stirred at room temperature for 1 hour to mix them. The excess amount of the compound 7D was washed out alternately with a solution (0.05 mol of Tris, pH 8.0 and 0.5 mol of NaCl) and another solution (0.05 mol of formic acid, pH 4.0 and 0.5 mol of NaCl). The gel was collected (on the glass).

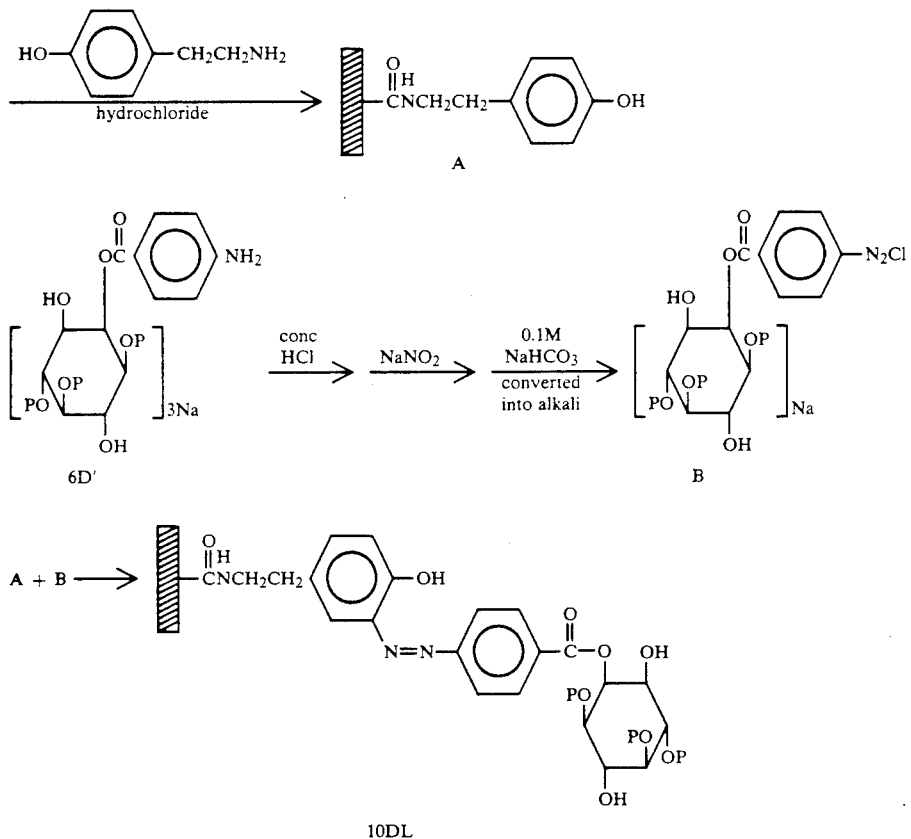

10DL

A compound 10DL was obtained by coupling a diazonium salt B formed from an amine with a compound A formed by coupling 1 g of a gel with 3 mg of tyramine in a usual manner.

Example 14

Preparation of a 7D-Sepharose 11D by the use of an activated CH-Sepharose 4B

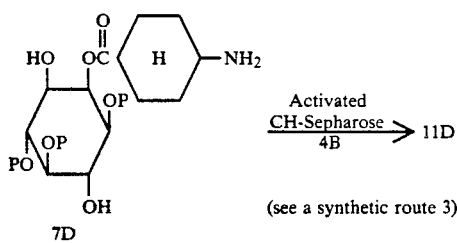

7D

Activated
CH-Sepharose
4B → 11D (see a synthetic route 3)

Example 15

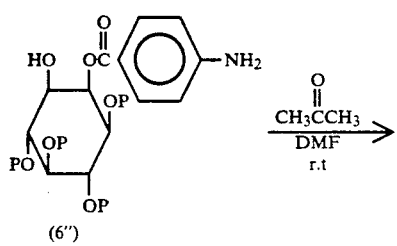

(6")

$$CH_3CCH_3 \atop DMF \quad r.t$$

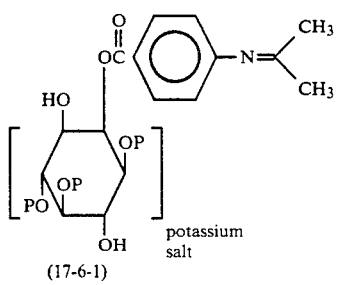

(17-6-1)

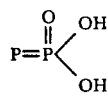

The symbol " means that phosphoric acid is in a free state, i.e., that it does not form a salt with any one.

0.030 g (0.056 mmol) of a free IP₃(1,4,5) 2 position

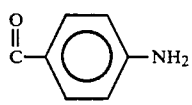

compound (6") was dissolved in 2 ml of DMF. 1 ml of acetone (excess) was added the solution, and reaction was carried out at room temperature for 1 day. After completion of the reaction, DMF and excess acetone were distilled off under reduced pressure by means of a vacuum pump. Afterward, a residue was isolated through a CC-31 cellulose column. The resultant ammonium salt was converted into a potassium salt by the use of Dowex 50W-x ion exchange resin. 0.012 g of a product was obtained and a yield was 31%.

IR Absorption was observed at 1650 cm⁻¹.

Example 16

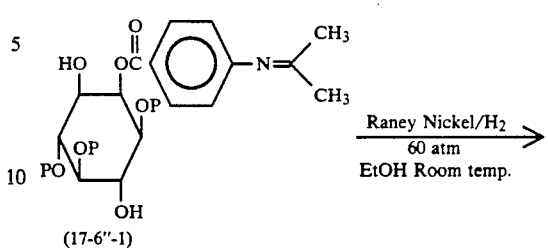

(17-6"-1)

Raney Nickel/H₂
60 atm
EtOH Room temp.

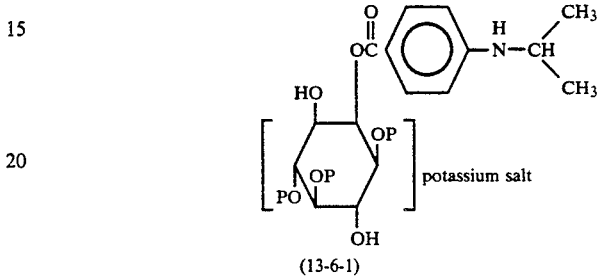

(13-6-1)

0.020 g (0.034 mmol) of a free imine (a compound 17-6"-1) was placed in an autoclave and then dissolved in 5 ml of ethanol. A catalytic amount of a Raney nickel was added thereto, and reaction was then carried out under a hydrogen pressure of 60 atm for 12 hours. After completion of the reaction, the catalyst was removed by filtration, and the resultant filtrate was then concentrated. A residue was isolated through a CC-31 cellulose column, and the ammonium salt was converted into a potassium salt by the use of Dowex 50W-x ion exchange resin. 0.020 g of a product was obtained in a yield of 84%.

¹H-NMR (D₂O, 270 MHz), δ 1.05 (d J=6.0 Hz 6H).

Example 17

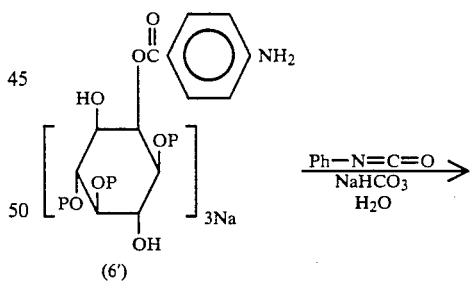

(6')

Ph—N=C=O
NaHCO₃
H₂O

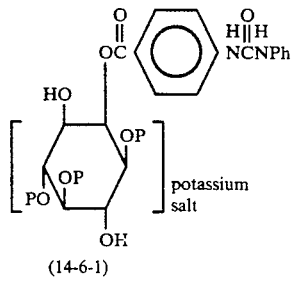

(14-6-1)

0.030 g (0.050 mmol) of the above-mentioned sodium salt (6') was dissolved in 2 ml of water. 0.012 g (0.14 mmol) of NaHCO₃ and 0.012 g (0.10 mmol) of phenyl isocyanate were added to the solution, and reaction was then carried out for 2 days. After completion of the reaction, water was distilled off, and the residue was passed through a cation exchange resin. After water was distilled off, isolation was made through a CC-31 cellulose column, and Dowex 50W-x ion exchange resin was used to convert the ammonium salt into a potassium salt. 0.023 g of a product was obtained and a yield was 60%.

IR 1660 cm$^{-1}$.

Example 18

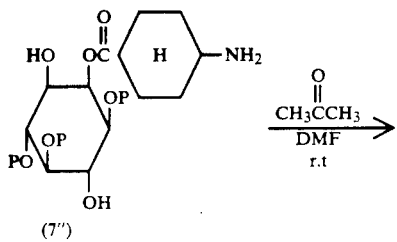

(7'')

0.030 g (0.055 mmol) of a compound (7'') was dissolved in 2 ml of DMF. 1 ml of acetone was added to the solution, and reaction was then carried out for 1 day. After completion of the reaction, DMF and acetone were distilled off under reduced pressure by means of a vacuum pump, and a residue was then isolated through a CC-31 cellulose column, and Dowex 50W-x ion exchange resin was used to convert the ammonium salt into a potassium salt. 0.015 g of a product was obtained in a yield of 39%.

IR 1655 cm$^{-1}$.

Example 19

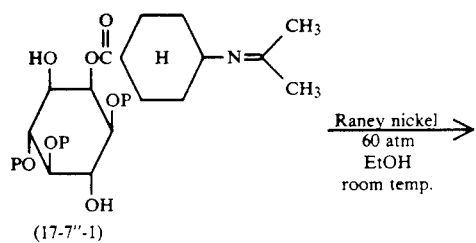

(17-7''-1)

-continued

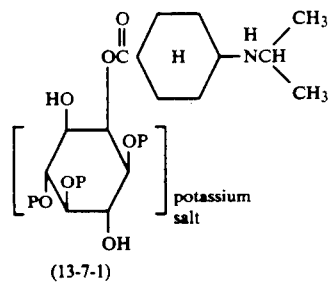

(13-7-1)

0.030 g (0.051 mmol) of a free imine (a compound 17-7''-1) was placed in an autoclave and then dissolved in 10 ml of EtOH. Afterward, a catalytic amount of a Raney nickel was added to the solution, and reaction was then carried out under a hydrogen pressure of 60 atm for 12 hours. After completion of the reaction, the catalyst was removed by filtration, and the resultant filtrate was then concentrated. A residue was isolated through a CC-31 cellulose column, and a Dowex 50W-x ion exchange resin was used to convert the ammonium salt into a potassium salt. 0.021 g of a product was obtained in a yield of 70%.

$^1$H-NMR (D$_2$O, 270 MHz), δ 1.0 (d J=6.0 Hz 6H).

Example 20

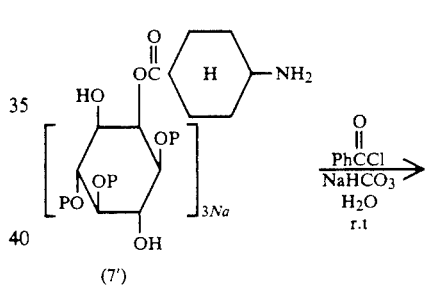

(7')

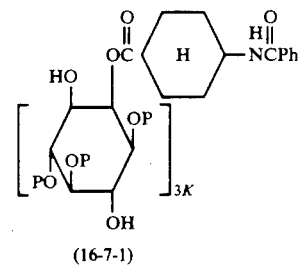

(16-7-1)

0.030 g (0.049 mmol) of the above-mentioned sodium salt (7') was dissolved in 2 ml of water. 0.042 g (0.50 mmol) of NaHCO$_3$ was then added to the solution. Successively, 0.020 g (0.15 mmol) of benzoyl chloride was added, and reaction was then carried out at room temperature for 6 hours. After completion of the reaction, water was distilled off, and the resultant residue was passed through a cation exchange resin and then isolated by a CC-31 cellulose column. Afterward, the ammonium salt was converted into a potassium salt by the use of Dowex 50W-x ion exchange resin. 0.027 g of a product was obtained and a yield was 71%.

IR 1655 cm$^{-1}$.

Example 21

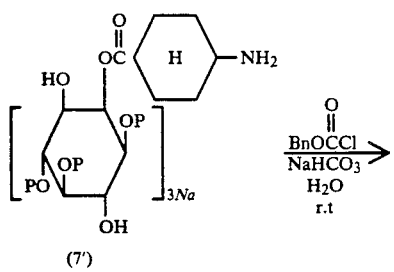

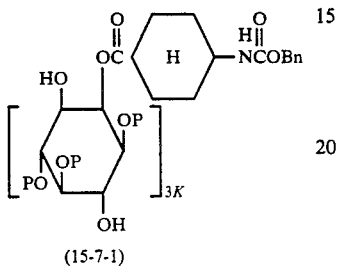

0.030 g (0.049 mmol) of the above-mentioned sodium salt (a compound 7') was dissolved in 2 ml of water. 0.042 g (0.50 mmol) of NaHCO₃ was then added to the solution. Successively, 0.025 g (0.147 mmol) of benzoyloxycarbonyl chloride was added, and reaction was then carried out at room temperature for 6 hours. After completion of the reaction, water was distilled off, and the resultant residue was then passed through a cation exchange resin. Isolation was made by a CC-31 cellulose column, and the ammonium salt was converted into a potassium salt by the use of Dowex 50W-x ion exchange resin. 0.021 g of a product was obtained and a yield of 55%.

IR 1725 cm⁻¹.

Example 22

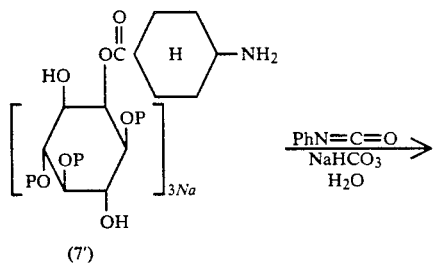

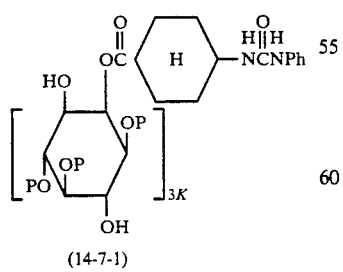

0.030 g (0.049 mmol) of the above-mentioned sodium salt (a compound 7') was dissolved in 2 ml of water. 0.012 g (0.14 mmol) of NaHCO₃ was then added to the solution. Successively, 0.012 g (0.10 mmol) of phenyl isocyanate was added, and reaction was then carried out for 2 days. After completion of the reaction, water was distilled off, and the resultant residue was then passed through a cation exchange resin. Isolation was made by a CC-31 cellulose column, and the ammonium salt was then converted into a potassium salt by the use of Dowex 50W-x ion exchange resin. 0.018 g of a product was obtained in a yield of 47%.

IR 1650 cm⁻¹.

Example 23

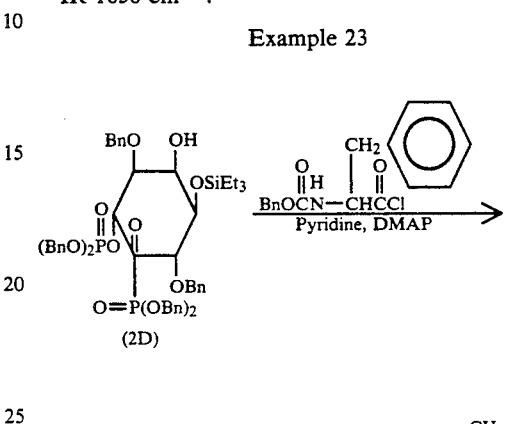

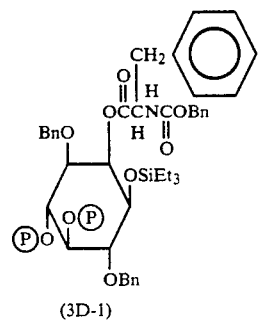

1.0 g (1.0 mmol) of a compound 2D was dissolved in 20 ml of anhydrous pyridine in a nitrogen gas. The solution was cooled with ice-water. Afterward, 0.84 g (3.0 mmol) of N-Z phenylalanine chloride was added thereto. Next, a catalytic amount of DMAP was added to the solution, and a solution temperature was raised to room temperature from the ice-water temperature and reaction was then carried out overnight. After completion of the reaction, water was added, followed by stirring for 30 minutes. Ether was added and extraction was made, and the solution was then washed with water, a 10% KHSO₄ solution, water, a saturated NaHCO₃ solution and water. The resultant organic layer was dried over MgSO₄ and then filtered, and the ether layer was evaporated. Afterward, a residue was isolated by a column chromatography. 1.053 g of a product was obtained in a yield of 85%.

IR 1730 cm⁻¹.

Example 24

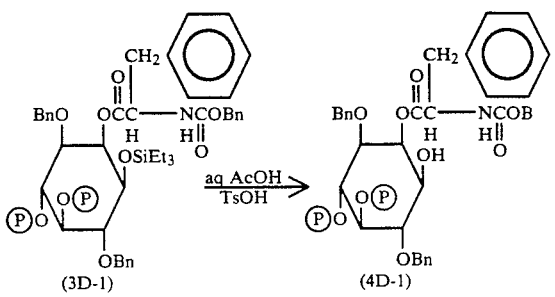

-continued

Example 24

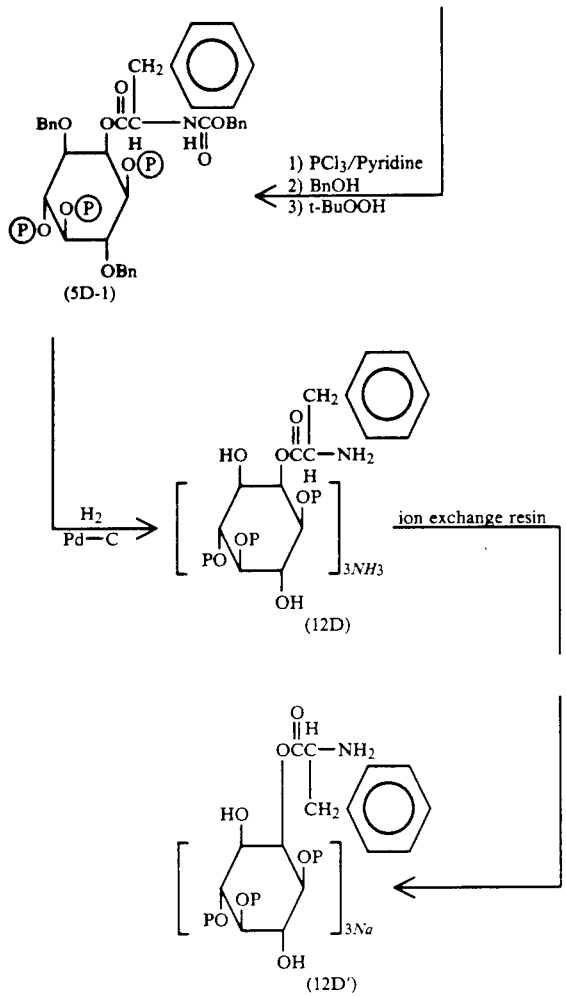

Compounds 3D-1 to 12D' were led by the same operation as in the case of the compounds 3D to 6D'.

A compound 12 D':

IR 1735 cm$^{-1}$.

Example 25

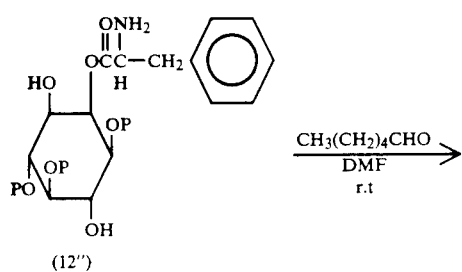

-continued

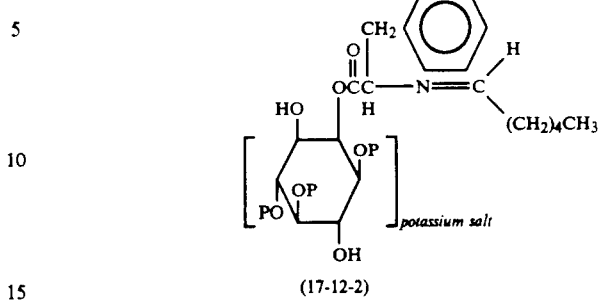

0.050 g (0.088 mmol) of a raw material 12'' was dissolved in dry DMF. 0.088 g (0.88 mmol) of hexanal was added to the solution. Reaction was then carried out at room temperature for 2 days. After completion of the reaction, DMF was distilled off under reduced pressure by means of a vacuum pump. A residue was then isolated through a CC-31 cellulose column, and Dowex 50W-x ion exchange resin was used to convert the ammonium salt into a potassium salt. 0.027 g of a product was obtained in a yield of 40%.

IR 1725, 1640 cm$^{-1}$.

Example 26

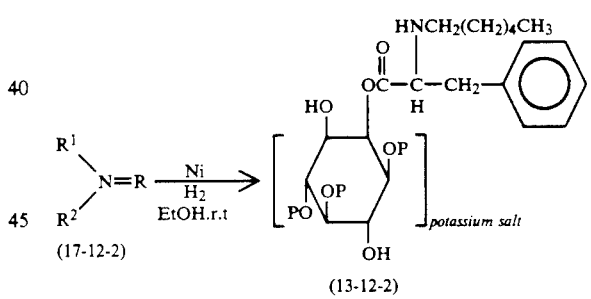

0.020 g (0.031 mmol) of a free imine (a compound 17-12-2) and 10 ml of ethanol which were raw materials were placed in an autoclave. Afterward, a catalytic amount of a Raney nickel was added to the solution, and reaction was then carried out under a hydrogen pressure of 60 atm for 24 hours. After completion of the reaction, the catalyst was removed by filtration, and the resultant filtrate was concentrated. Afterward, the resultant residue was purified through a CC-31 cellulose column, and conversion into a potassium salt was then effected by the use of Dowex 50W-x ion exchange resin. 0.013 g of a product was obtained in a yield of 55%.

IR 1735 cm$^{-1}$.

Example 27

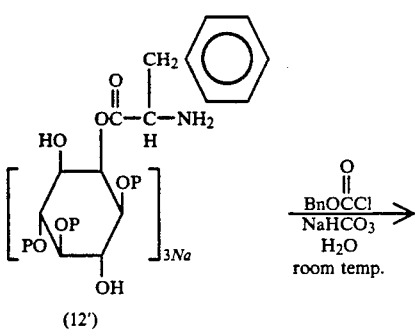

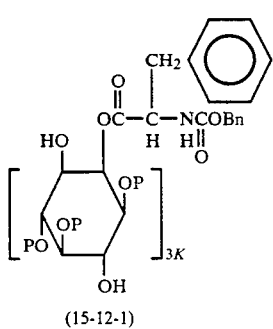

0.030 g (0.047 mmol) of a raw material (a compound 12') was dissolved in 2 ml of water. 0.040 g (0.47 mmol) of NaHCO₃ was then added to the solution. Successively, 0.024 g (0.141 mmol) of benzyloxycarbonyl chloride was added, and reaction was then carried out overnight. After completion of the reaction, water was distilled off, and the resultant residue was passed through a cation exchange resin. Isolation was made by a CC-31 cellulose column, and the ammonium salt was converted into a potassium salt by the use of Dowex 50W-x ion exchange resin. 0.029 g of a product was obtained in a yield of 75%.

IR 1720 cm⁻¹.

Example 28

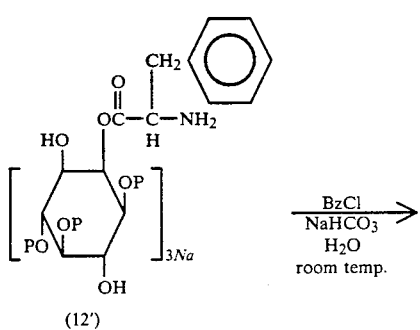

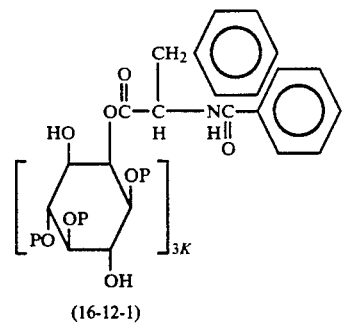

0.030 g (0.047 mmol) of a raw material (12') was dissolved in 2 ml of water. 0.040 g (0.47 mmol) of NaHCO₃ was then added to the solution. Successively, 0.033 g (0.24 mmol) of benzyl chloride was added, and reaction was then carried out overnight. After completion of the reaction, water was distilled off, and the resultant residue was then passed through a cation exchange resin. Afterward, isolation was made by a CC-31 cellulose column, and conversion into a potassium salt was effected by the use of Dowex 50W-x ion exchange resin. 0.025 g of a product was obtained in a yield of 80%.

IR 1650 cm⁻¹.

Example 29

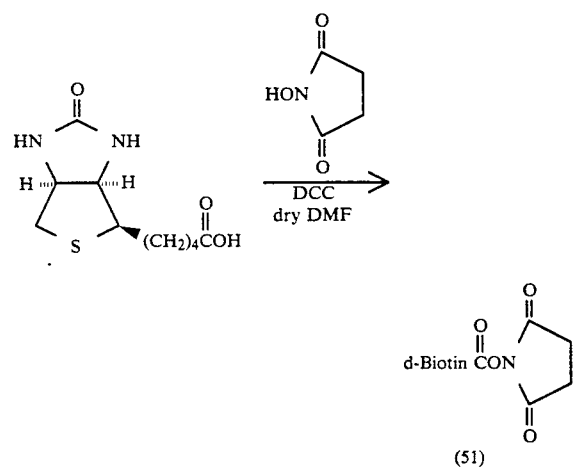

5.4 ml of anhydrous DMF was added to 0.300 g (1.22 mmol) of d-biotin. Successively, 0.155 g (1.35 mmol) of hydroxysuccinimide and 0.251 g (1.22 mmol) of dicyclohexylcarbodiimide were added. After reaction was carried out at room temperature for 10 hours, the reaction solution was allowed to stand for a period of from 1 to 2 hours in an icebox. The precipitated DCC urea was filtered and then washed with a small amount of DMF. The resultant filtrate was distilled off under reduced pressure by means of a vacuum pump, and the residue was then recrystallized from isopropanol. 0.3709 g of a product was obtained in a yield of 89%, and its melting point was from 200° to 202° C.

DMSO-CDCl₃ 270 MHz

¹H NMR 6.307(1H s -N(H)-) 6.274(1H s -N(H)-)

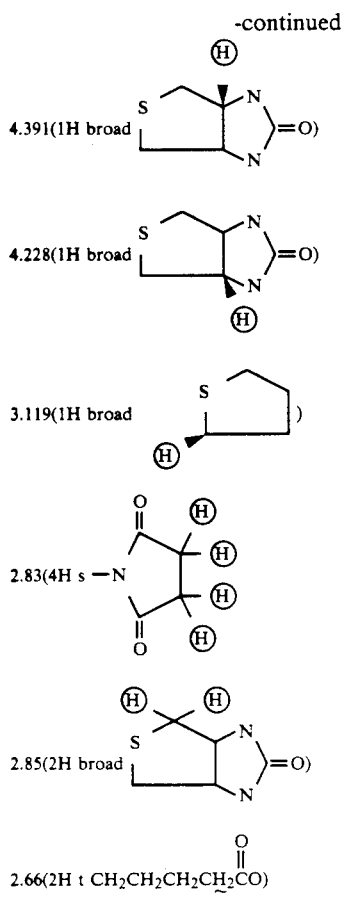

4.391(1H broad 4.228(1H broad 3.119(1H broad 2.83(4H s —N 2.85(2H broad 2.66(2H t CH$_2$CH$_2$CH$_2$CH$_2$C̱O)

1.6(6H m CH$_2$CH$_2$CH$_2$CH$_2$C̱O)

IR(nujol) 3200, 2900, 1820, 1780, 1740, 1720, 1700, 1070, 840 cm$^{-1}$.

Example 30

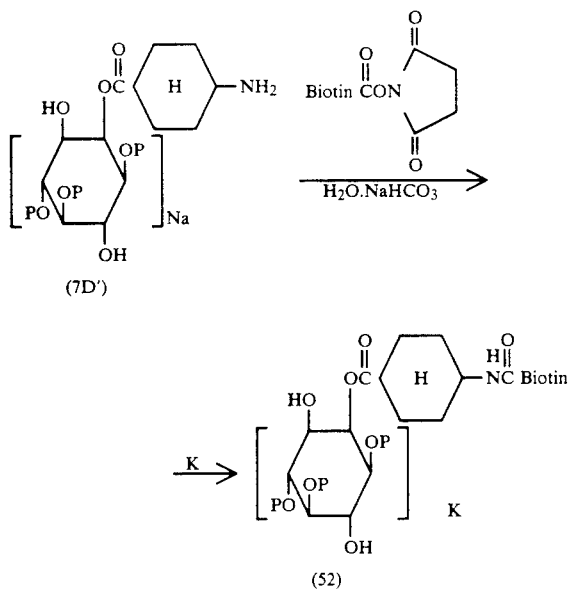

(7D')

(52)

0.030 g (0.049 mmol) of IP$_3$ (1,4,5) 2 position

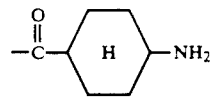

was dissolved in 2 ml of water. Successively, 0.012 g (0.14 mmol) of NaHCO$_3$ and 0.034 g (0.10 mmol) of biotin

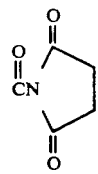

were added and reaction was then carried out at room temperature for 6 days. After completion of the reaction, water was distilled off, and the resultant residue was passed through a cation exchange resin. Next, water was distilled off, and a residue was then separated by a CC-31 cellulose column (eluting solvent; n-PrOH:-conc. NH$_4$OH:H$_2$O=6:3:1). Afterward, the solvent was distilled off, and the ammonium salt was then converted into a potassium salt by passing through Dowex 50W-x ion exchange resin. 11.5 g of a product was obtained and a yield was 25%.

$^1$H-NMR (D$_2$O, 270 MHz), 5.500, 5.415 (1H 2 position), 4.45(1H broad 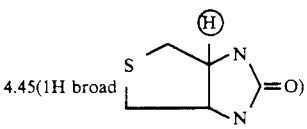

4.27(1H broad 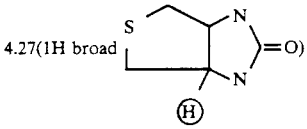

3.40~4.20(7H m H$_1$.H$_3$.H$_4$.H$_5$.H$_6$. 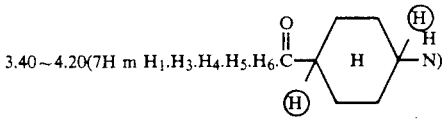

3.19(1H broad 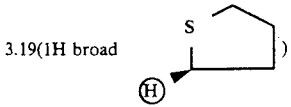

2.81(1H dd 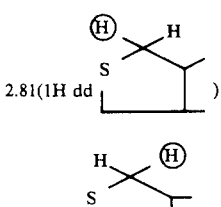

2.60(1H s 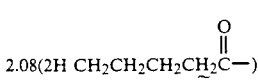

2.08(2H CH$_2$CH$_2$CH$_2$CH$_2$C̱—)

1.6(6H m CH₂CH₂CH₂CH₂C—)

Example 31

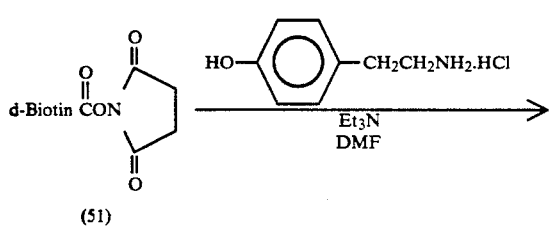

(51)

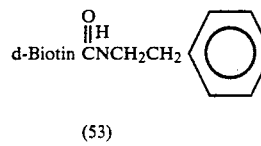

(53)

0.1766 g (0.52 mmol) of d-biotin

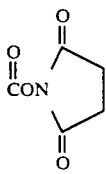

was dissolved in 2 ml of dry DMF. Successively, 0.090 g (0.52 mmol) of tyramine.hydrochloride and 0.157 g (1.56 mmol) of triethylamine were added to the solution and reaction was then carried out at room temperature for 48 hours. After completion of the reaction, DMF was distilled off under reduced pressure by means of a vacuum pump. The residue was then subjected to a silica gel column chromatography to achieve isolation (eluting solvent; CH₂Cl₂:MeOH=10:1). Afterward, the solvent was distilled off, and the resultant residue was passed through a cation exchange resin for the purpose of purification. 0.138 g of a product was obtained and a yield was 70%.

¹H-NMR (CD₃OD/CDCl₃, 270 MHz),

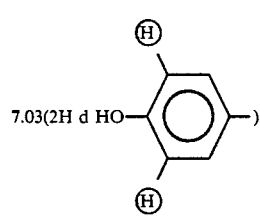
7.03(2H d HO—⟨ ⟩—)

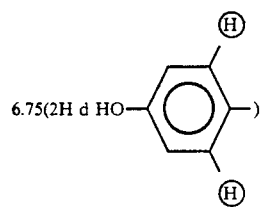
6.75(2H d HO—⟨ ⟩—)

4.52(1H broad 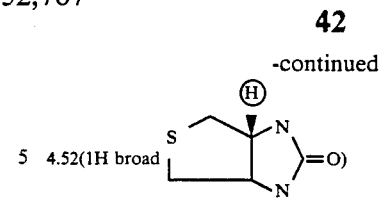)

4.30(1H broad 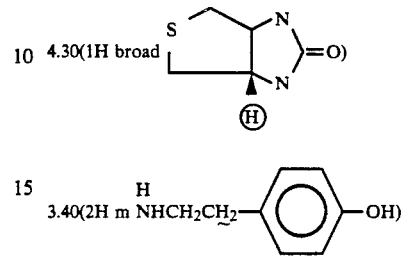)

3.40(2H m NHCH₂CH₂—⟨ ⟩—OH)

3.15(1H broad 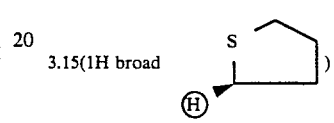)

2.93(1H dd 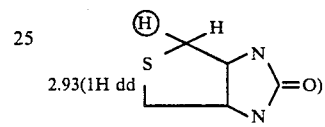)

2.72(3H m NCH₂CH₂—⟨ ⟩—OH 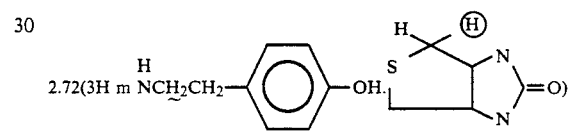)

2.13(2H t CH₂CH₂CN—)

1.60(4H m CH₂CH₂CH₂CH₂CN—)

1.38(2H broad CH₂CH₂CH₂CHCN—)

IR (nujol) 3300, 2900, 1670, 1630, 1530, 1500, 1220, 1160, 820, 710 cm⁻¹.

Example 32

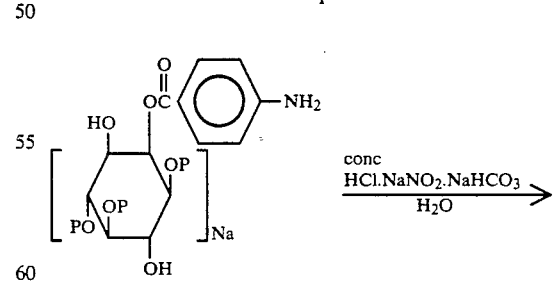

6D'

HO—⟨ ⟩—CH₂CH₂NC Biotin
                    ‖
                    O
                    H
⟶ K ⟶

-continued

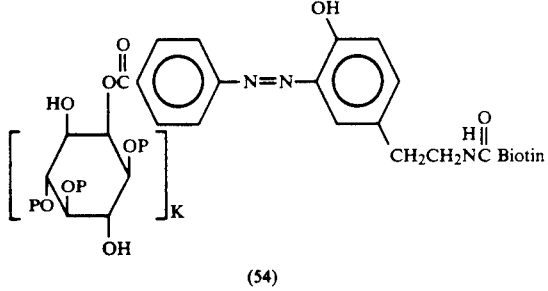

(54)

0.030 g (0.050 mmol) of a raw material was dissolved in 2 ml of water, and the solution was then cooled with ice-water. Next, concentrated hydrochloric acid 0.018 g/41 μl (0.50 mmol) was added to the solution. Successively, a sodium nitrite 0.010 g (0.14 mmol)/H$_2$O 1 ml solution was added. After stirring for 30 minutes, blue violet was confirmed by a potassium iodide starch test paper, and 0.045 (0.54 mmol) of NaHCO$_3$ was added. After it was confirmed by a pH test paper that the solution was alkaline, 0.027 g (0.07 mmol) of

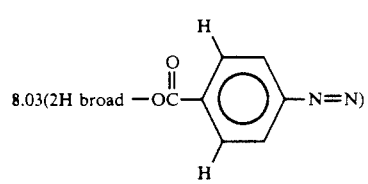

biotin was added. A reaction temperature was raised from 0° C. to room temperature, and reaction was then carried out for 3 hours. After completion of the reaction, water was distilled off, and the residue was passed through a cation exchange resin. A concentrated aqueous NH$_4$OH solution was added to the resultant eluate, and water was then distilled off and a residue was isolated by a CC-31 cellulose column (eluting solvent; n-PrOH:conc. NH$_4$OH:H$_2$O=6:3:1). Afterward, the eluting solvent was distilled off, and the residue was then passed through Dowex 50W-x ion exchange resin to convert the ammonium salt into a potassium salt. 34.4 mg of a product was obtained in a yield of 71%.

$^1$H-NMR (D$_2$O 270 MHz),

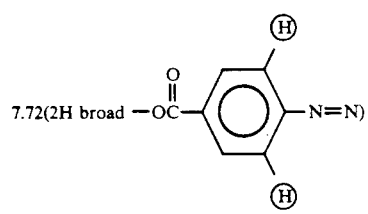

8.03(2H broad —OC—〈 〉—N=N)

7.72(2H broad —OC—〈 〉—N=N)

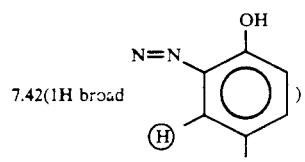

7.42(1H broad )

-continued

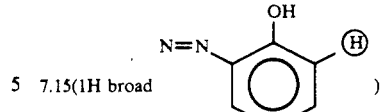

7.15(1H broad )

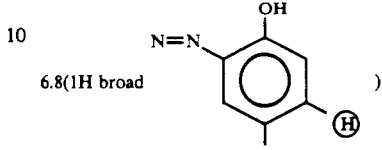

6.8(1H broad )

5.75 (1H s H$_2$) 3.75~4.40 (5H m H$_1$, H$_3$, H$_4$, H$_5$, H$_6$),

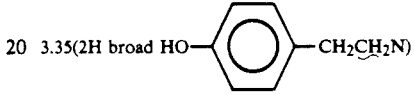

3.35(2H broad HO—〈 〉—CH$_2$CH$_2$N)

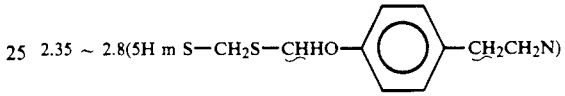

2.35 ~ 2.8(5H m S—CH$_2$S—CHHO—〈 〉—CH$_2$CH$_2$N)

1.95(2H t —CH$_2$CH$_2$CH$_2$CH$_2$CN)

1.15(4H broad —CH$_2$CH$_2$CH$_2$CH$_2$CNH)

0.75(2H broad —CH$_2$CH$_2$CH$_2$CH$_2$CNH)

$^{31}$P-NMR (270 MHz, D$_2$O), 0.759 (H$_1$), 2.210 (H$_5$), 2.913 (H$_4$).

Example 33

Synthesis of synthesized ε-Boc-lysine of IP$_3$ 2 position analog (lysine part)

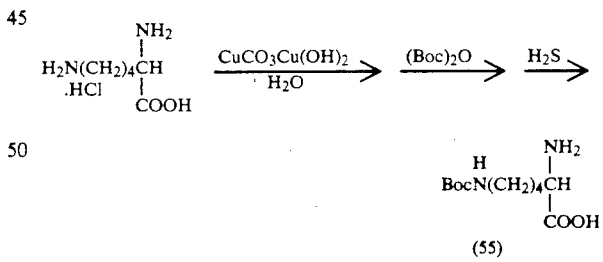

(55)

18.3 g (0.1 mol) of an L-lysine salt was dissolved in 250 ml of hot water. 12 g (0.05 mol) of CuCO$_3$.Cu(OH)$_2$.H$_2$O was added to the solution. The solution was boiled for about 10 minutes and then filtered, and the resultant filtrate was cooled. Next, 250 ml of a dioxane solution containing 8.4 g (0.1 mol) of NaHCO$_3$ and 24 g (0.11 mol) of (Boc)$_2$O was added to the cooled filtrate. Furthermore, the solution was stirred for 2 hours at room temperature, and the precipitated Lys (Boc)·½Cu was collected by filtration, washed with water and then dried. 14 g (0.05 mol) of this copper salt was suspended in 300 ml of water, and 50 ml of 2 M.NH$_4$OH was then added under ice cooling. H$_2$S was bubbled through the solution for 3 hours, and 75 ml of 2M-AcOH was then added Afterward, air was bubbled through the solution until the odor of H₂S had been imperceptible. CuS was removed by filtration, and the resultant filtrate was concentrated and then allowed to stand in an icebox. After precipitation was made sufficiently, this precipitate was collected by filtration and then washed with a small amount of water. The filtrate was subjected to the above-mentioned operation repeatedly, and the respective portions of the precipitate were joined together. As a result, 11 g of a product was obtained in a yield of 88%.

m.p.: 230°-231° C.

Example 34

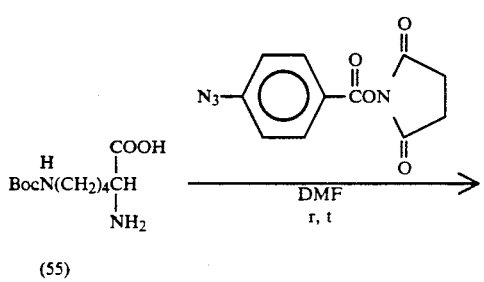

0.17 g (0.69 mol) of ε-Boc-lysine was dissolved in 2 ml of anhydrous DMF. 0.18 g (0.69 mmol) of 4-azidobenzoic acid N-hydroxysuccinimide ester was added to the solution, and reaction was then carried out at room temperature for 6 hours. After completion of the reaction, DMF was distilled off by means of a vacuum pump, and chloroform was added to the residue and extraction was made, followed by separation with a 10% NaHCO₃. A 1M aqueous hydrochloric acid solution was added to the resultant aqueous layer, and extraction was then made with chloroform. Next, water was added to the resultant organic layer, and this organic layer was washed, dried over MgSO₄, and then filtered. CHCl₃ was distilled off, so that 0.25 g of a product was obtained in a yield of 93%.

¹-NMR (CDCl₃, 90 MHz)

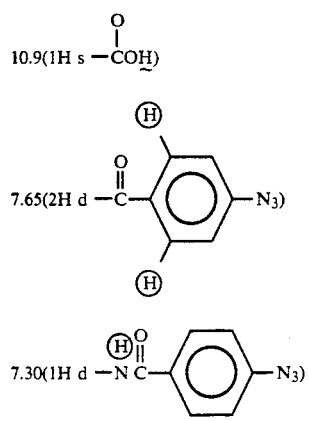

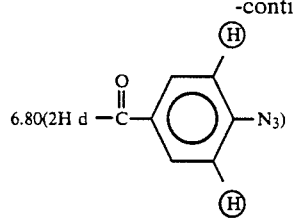

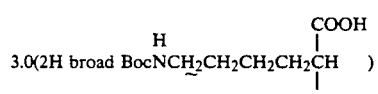

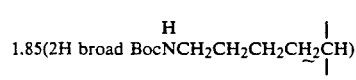

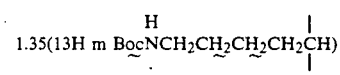

IR (neat) 3350, 2950, 2500, 2100, 1700, 1640, 1600, 1530, 1480, 1360, 1280, 1180, 1100, 840, 740 cm⁻¹.

Example 35

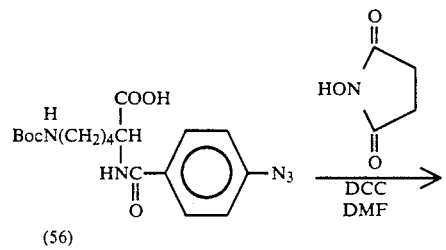

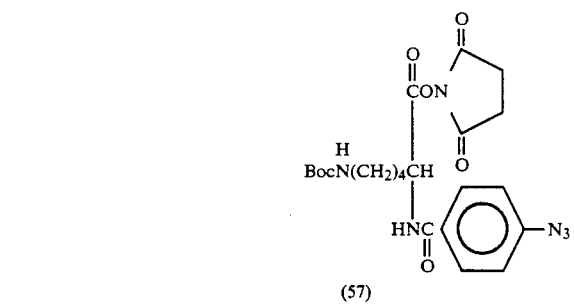

0.1136 (0.29 mmol) of a carboxylic acid was dissolved in 2 ml of DMF. 0.037 g (0.32 mmol) of N-hydroxy succinimide and 0.062 g (0.30 mmol) of DCC were added to the solution. Reaction was carried out at room temperature for 4 hours, and DCC and urea were removed by filtration and the resultant filtrate was distilled off under reduced pressure by means of a vacuum pump. AcOEt was added to the residue and extraction was then made. The extract was washed with water, dried over MgSO₄ and then filtered, and AcOEt was distilled off. 0.145 g of the resultant residue was led to the next reaction without isolation and purification.

IR (neat) 3900, 2950, 2850, 2100, 1800, 1780, 1730, 1680, 1640, 1600, 1480, 1440, 1360, 1280, 1200, 1070, 840, 740 cm$^{-1}$.

Example 36

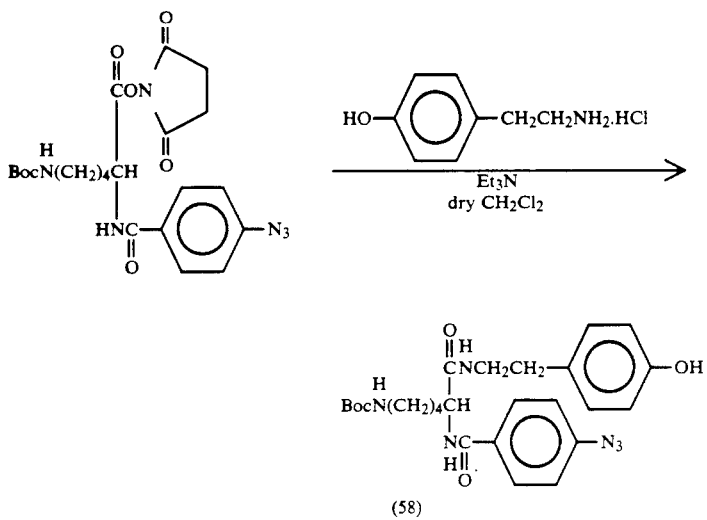

0.14 g (0.29 mmol) of succinimide ester was dissolved in 2 ml of anhydrous methylene chloride. 0.050 g (0.29 mmol) of tyramine.hydrochloride and 0.035 g (0.34 mmol) of Et$_3$N were added to the solution and reaction was then carried out at room temperature for 3 hours. After completion of the reaction, CH$_2$Cl$_2$ was added to the reaction solution and extraction was then made, and the extract was washed with water, a 10% oxalic acid solution, water, a 10% NaHCO$_3$, an aqueous solution and water, dried over MgSO$_4$, and then filtered. Afterward, CH$_2$Cl$_2$ was distilled off and a column chromatography (9 g of silica gel C-300; eluting solvent of CH$_2$Cl$_2$ and Et$_2$O in a ratio of 1:2) was used, and as a result, 0.085 g of a product was obtained in a yield of 60%.

$^1$H-NMR (CDCl$_3$ 90 MHz),

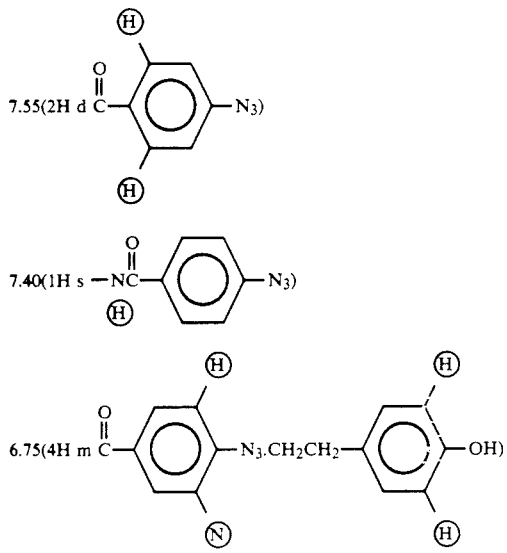

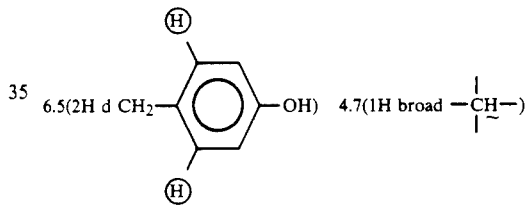

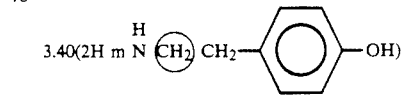

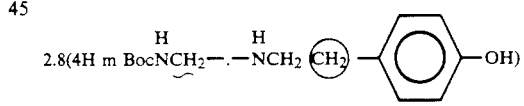

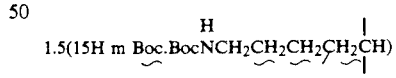

IR (nujol) 3300, 2950, 2100, 1680, 1630, 1530, 1500, 1220, 1160, 820, 710 cm$^{-1}$.

Example 37

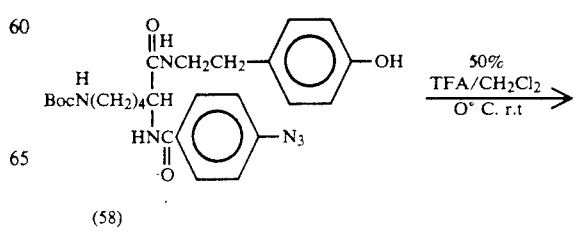

-continued

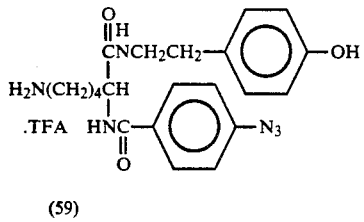

(59)

0.080 g (0.16 mmol) of Boc-lysine was dissolved in 1 ml of methylene chloride. The solution was cooled with ice-water, and 1 ml of TFA (trifluoroacetic acid) was added and reaction was then carried out at room temperature for 1 hour. After completion of the reaction, TFA and $CH_2Cl_2$ were distilled off, and the residue was dried under reduced pressure by means of a vacuum pump. 0.075 g of the dried residue was led to a next reaction without isolation and purification.

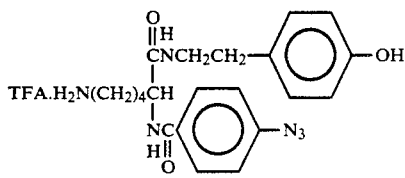

CHCl$_3$ and MeOH in a ratio of 7:1), and 0.026 g of a product was obtained in a yield of 60%.

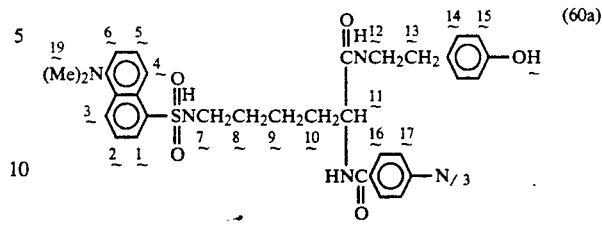
(60a)

$^1$H-NMR (DMSO d$_6$ 270 MHz), 8.52 (1H d $\underline{1}$), 8.29 (1H d $\underline{4}$), 8.15 (1H d $\underline{3}$), 7.85 (2H d $\underline{16}$), 7.45 (2H m $\underline{2,5}$), 7.20 (1H d $\underline{6}$), 7.05 (2H d $\underline{15}$), 7.00 (2H d $\underline{17}$), 6.75 (2H d $\underline{14}$), 5.60 (1H broad $\underline{18}$), 4.65 (1H broad $\underline{11}$), 3.40 (2H t $\underline{12}$), 2.95 (8H s $\underline{19}$ $\underline{7}$), 2.65 (2H t $\underline{13}$), 1.85 (2H broad $\underline{10}$), 1.45 (4H broad $\underline{8}$, $\underline{9}$).

0.030 g (0.057 mmol) of the amine salt ② was dissolved in 2 ml of anhydrous DMF. 0.021 g (0.063 mmol) of d-biotin

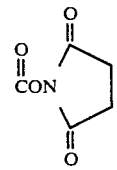

was added to the solution. Successively, 0.009 g (0.086 mmol) of Et$_3$N was added, and reaction was then carried out for 12 hours. After completion of the reaction, DMF was distilled off under reduced pressure by means of a vacuum pump, and isolation was then effected by a column chromatography (6 g of silica gel; eluting solvent of $CH_2Cl_2$ and MeOH in a ratio of 7:1). As a result, 0.025 g of a product was obtained in a yield of 70%.

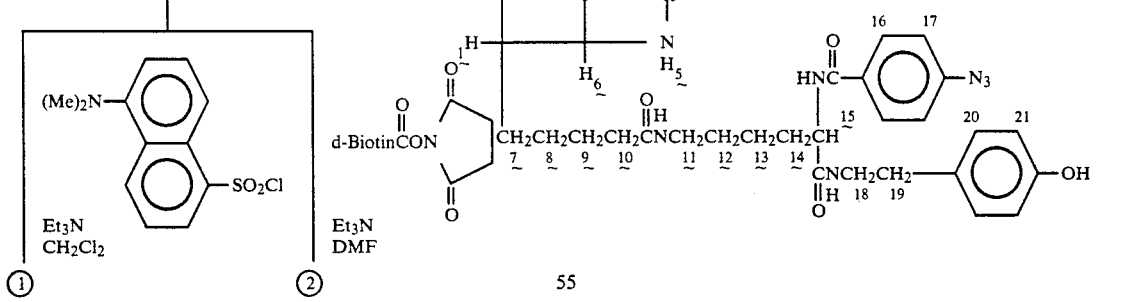
(60b)

0.035 g (0.067 mmol) of the amine salt ① was dissolved in 2 ml of anhydrous methylene chloride. 0.022 g (0.080 mmol) of dansyl chloride was added to the solution. Successively, 0.020 g (0.201 mmol) of Et$_3$N was added, and reaction was carried out at room temperature overnight. After completion of the reaction, $CH_2Cl_2$ was added to the reaction solution and extraction was then made. Afterward, the extract was washed with water, a saturated NaHCO$_3$ solution and water, dried over MgSO$_4$, and then filtered, and $CH_2Cl_2$ was distilled off. The residue was then subjected to a column chromatography (6 g of silica gel; eluting solvent of $^1$H-NMR (DMSO d$_6$ 270 MHz), 8.21 (1H d $\underline{4}$), 8.00 (2H d $\underline{16}$), 7.53 (1H broad $\underline{5}$), 7.10 (2H d $\underline{17}$), 7.05 (2H d $\underline{20}$), 6.85 (2H d $\underline{20}$), 4.45 (2H 3, $\underline{15}$), 4.25 (1H broad $\underline{6}$), 3.40 (2H t $\underline{18}$), 3.10 (3H m $\underline{11}$, $\underline{1}$), 2.75~3.0 (4H m 2, $\underline{19}$), 2.10 (2H t $\underline{10}$), 1.35~1.80 (12H m $\underline{7}$, $\underline{8}$, $\underline{9}$, $\underline{12}$, $\underline{13}$, $\underline{14}$).

Example 38

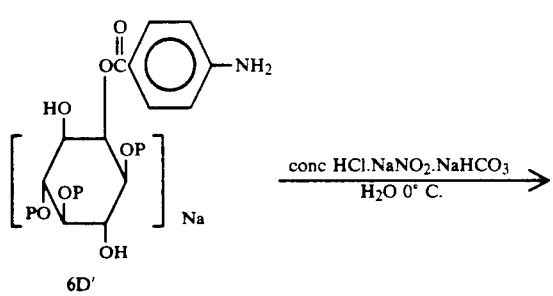

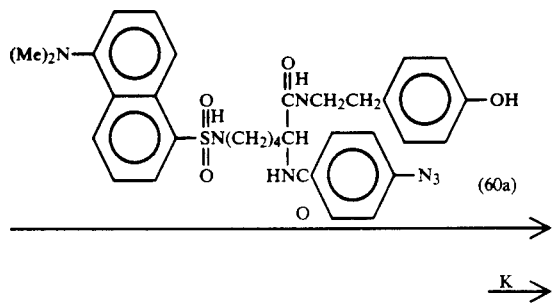

0.020 g (0.032 mmol) of IP3 (1,4,5) 2 position was dissolved in 2 ml of water. The solution was then cooled with ice-water, and concentrated HCl 0.012/27 μl (0.32 mmol) was added. Successively, NaNO2 0.004 g/H2O 1 ml (0.064 mmol) was added. After stirring at 0° C. for 30 minutes, blue violet was confirmed by a potassium iodide starch test paper, and 0.027 g (0.32 mmol) of NaHCO3 was added. After it was confirmed by a pH test paper that the solution was alkaline, 0.021 g (0.032 mmol) of a lysine part was added. Reaction was carried out at room temperature for 3 hours, and water was then distilled off and the residue was passed through a cation exchange resin. Concentrated aqueous ammonia was added and the eluate was then distilled off, and a residue was isolated by a CC-31 cellulose column (eluting solvent; n-PrOH:conc. NH4OH:H2O=6:3:1). Next, the solvent was distilled off, and the residue was then passed through a Dowex 50W-x ion exchange resin to convert the ammonium salt into a potassium salt. 0.025 mg of a product was obtained in a yield of 60%.

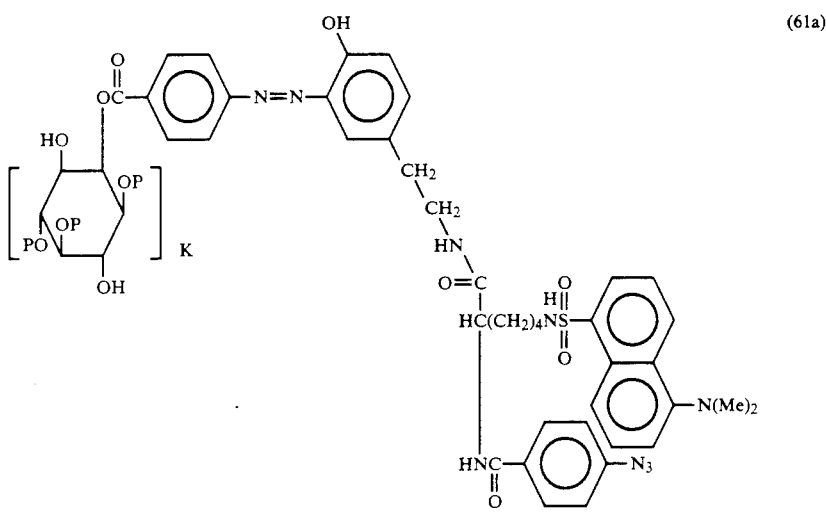

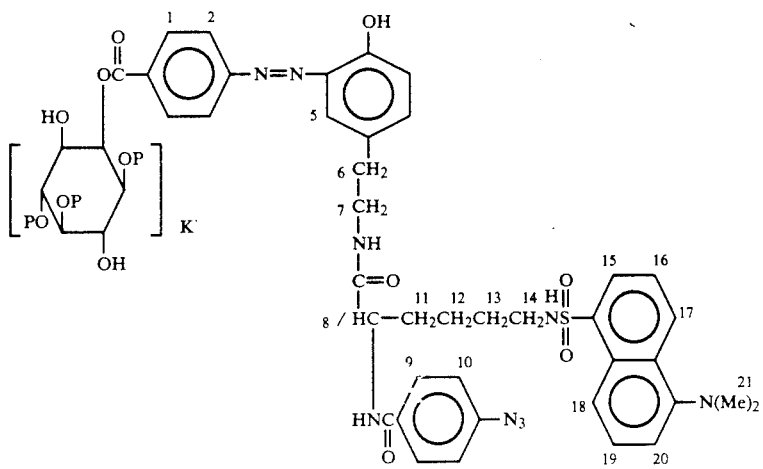

¹H-NMR (DMSO d₆ 270 MHz), 8.52 (1H d 1̲5̲), 8.29 (1H d 1̲8̲), 8.15 (1H d 1̲7̲), 8.03 (4H broad 1̲, 9̲), 6.80~7.80 (10H m 2̲, 3̲, 4̲, 5̲, 1̲0̲, 1̲6̲, 1̲9̲, 2̲0̲), 5.80 (1H s H₂), 3.80~4.60 (6H m H₁, H₃, H₄, H₅, H₆, 8̲), 3.40 (2H broad 7̲), 3.00 (8H s 1̲4̲, 2̲1̲), 2.65 (2H broad 6̲), 1.85 (2H broad 1̲1̲), 1.40 (4H broad 1̲2̲, 1̲3̲).

Example 39

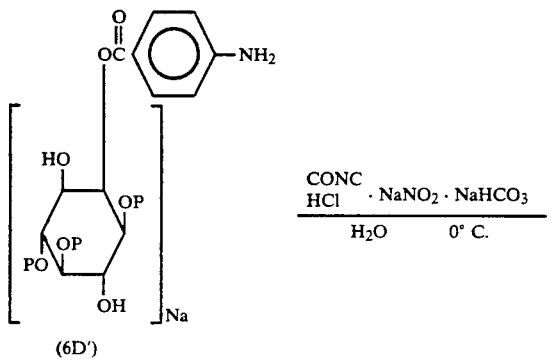

(6D')

$$\xrightarrow[\text{H}_2\text{O} \quad 0°\text{C.}]{\text{CONC HCl} \cdot \text{NaNO}_2 \cdot \text{NaHCO}_3}$$

0.020 g (0.032 mmol) of IP₃(1,4,5) 2 position

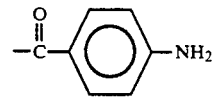

was dissolved in 2 ml of water. The solution was cooled with ice-water, and concentrated HCl 0.012 g/27 μl (0.32 mmol) was added to the solution. Successively, NaNO₂ 0.004 g/H₂O 1 ml (0.064 mmol) was added. After stirring at 0° C. for 30 minutes, blue violet was confirmed by a potassium iodide starch test paper, and 0.027 g (0.32 mmol) of NaHCO₃ was added. After it was confirmed by a pH test paper that the solution was alkaline, 0.020 g (0.032 mmol) of a lysine part was added. Reaction was carried out at room temperature for 3 hours, and water was then distilled off. The residue was passed through a cation exchange resin. Concentrated aqueous ammonia was added and the eluate was distilled off, and a residue was isolated by a CC-31 cellulose column (eluting solvent; n-PrOH:conc. NH₄OH:H₂O=6:3:1). Next, the solvent was distilled off, and the residue was then passed through Dowex 50W-x ion exchange resin to convert the ammonium salt into a potassium salt. 0.023 mg of a product was obtained in a yield of 55%.

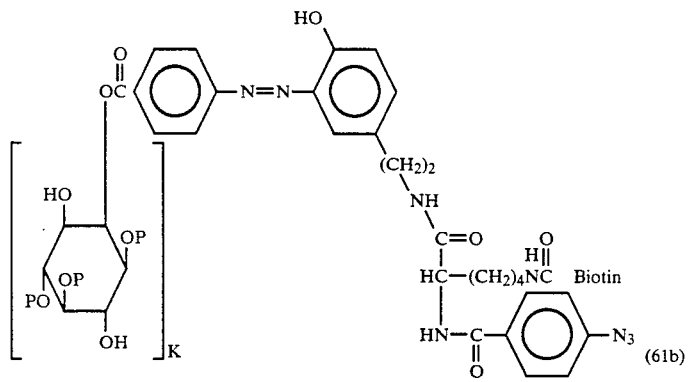

(61b)

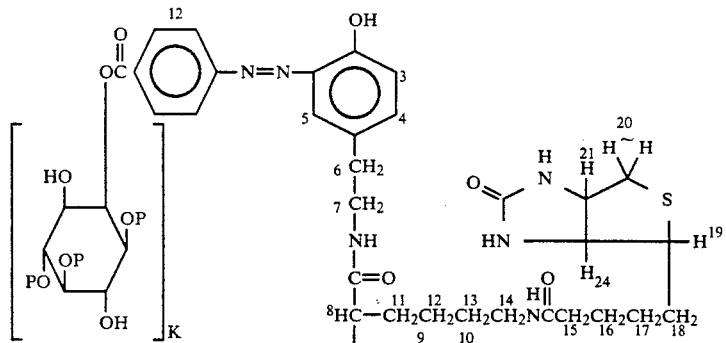

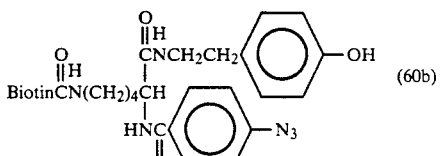

(60b)

$$\xrightarrow{\quad\quad\quad\quad}$$
$$\xrightarrow{\quad\text{K}\quad}$$

¹H-NMR (D₂O 270 MHz) 8.03 (4H broad 1̲, 9̲), 7.72 (2H broad 2̲), 7.42 (1H broad 5̲), 7.15 (1H broad 3̲), 7, 7.05 (2H d 1̲0̲), 6.8 (1H broad 4̲), 5.75 (1H S H₂), 3.75~4.60 (8H m H₁, H₃, H₄, H₅, H₆, 8̲, 2̲1̲, 2̲4̲), 3.35 (2H broad 7̲), 2.35~3.2 (7H m 6̲, 1̲4̲, 2̲0̲, 1̲9̲), 2.00 (2H t 1̲5̲), 1.50 (12H m 11, 12, 13, 16, 17, 18), 2.00 (2H t 15), 1.50 (12H m 11, 12, 13, 16, 17, 1̲8̲).

Example 40

Another method

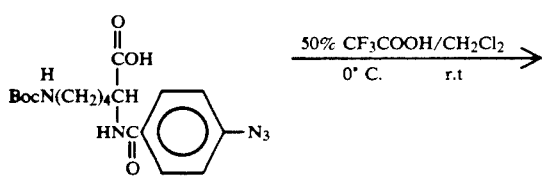

(56)

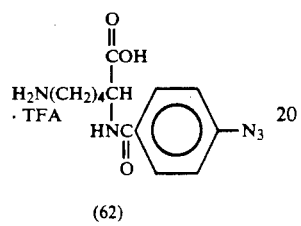

(62)

0.2755 (0.70 mmol) of a carboxylic acid was dissolved in 2 ml of methylene chloride. The solution was cooled with ice-water, and 2 ml of TFA was added thereto and reaction was then carried out at room temperature for 1 hour. After completion of the reaction, TFA and $CH_2Cl_2$ were distilled off, and the residual was dried under reduced pressure by means of a vacuum pump. 0.2700 g of the dried residue was led to a next reaction without isolation and purification.

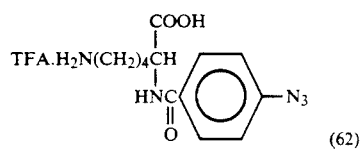

(62)

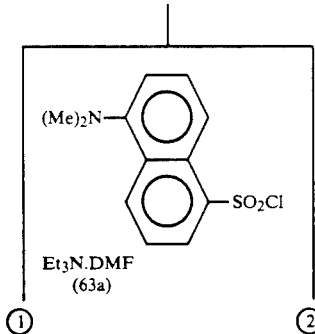

Et₃N.DMF
(63a)

①

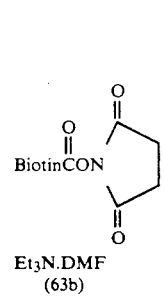

Et₃N.DMF
(63b)

②

0.1001 g (0.247 mmol) of the amine salt ① was dissolved in 2 ml of anhydrous DMF. 0.080 g (0.296 mmol) of dansyl chloride was added to the solution. Successively, 0.075 g (0.741 mmol) of Et₃N was added. After reaction for 12 hours, DMF was distilled off under reduced pressure by means of a vacuum pump, and chloroform was added to the resultant residue and extraction was then made. A saturated $NaHCO_3$ solution was added to the resultant organic layer, and a 2N HCl solution was added to the separated aqueous layer and extraction was then made with chloroform. The organic layer was washed with water, dried over $MgSO_4$ and then filtered, and $CH_2Cl_3$ was distilled off. In consequence, 0.0574 g of a product was obtained in a yield of 44%.

¹H-NMR (CDCl₃, 270 MHz),

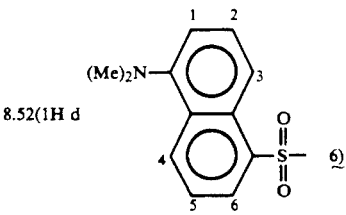

8.52(1H d 6̲)

8.29 (1H d 3̲), 8.19 (1H d 4̲),

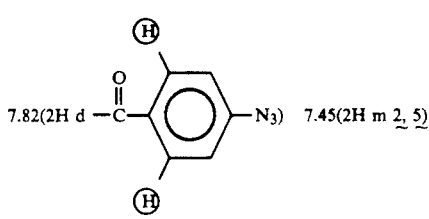

7.82(2H d) 7.45(2H m 2̲, 5̲)

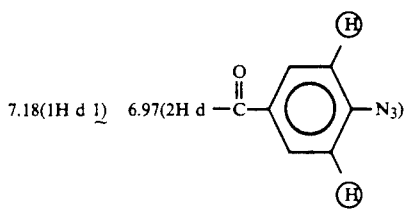

7.18(1H d 1̲)  6.97(2H d)

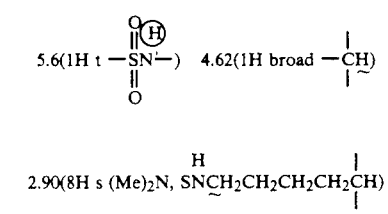

5.6(1H t —SN—)  4.62(1H broad —C̲H)

2.90(8H s (Me)₂N, SNC̲H₂CH₂CH₂CH₂C̲H)

1.8(2H broad CH₂CH₂CH₂C̲H₂CH)

1.4(4H broad NCH₂C̲H₂C̲H₂CH₂CH)

0.040 g (0.099 mmol) of an amine salt ② was dissolved in 1 ml of anhydrous DMF. 0.034 g (0.099 mmol) of biotin N-hydroxysuccinimide ester was added to the solution. Successively, 0.020 g (0.198 mmol) of Et₃N was added and reaction was then carried out at room temperature for 20 hours. After completion of the reaction, DMF was distilled off by means of a vacuum pump, and isolation was then effected by the use of a column chromatography (eluting solvent of CHCl₃:MeOH:conc. NH₄OH in a ratio of 7:3:0.3). The solvent was distilled off, and a desired product was taken out as a carboxylic acid with the aid of a cation exchange resin. The amount of the product was 0.043 g and a yield was 84%.

¹H-NMR (DMSO d₆ 270 MHz),

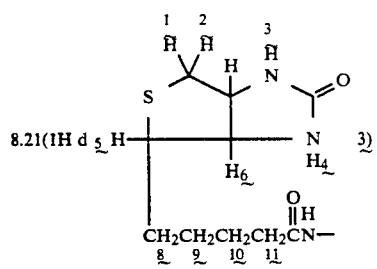

8.21(1H d 5 H)

8.00(2H d) 7.53(1H broad 4)

-continued 4.25(1H broad 6)

3.13(3H m CH$_2$CNCH$_2$CH$_2$. 5)

2.80(2H m 1, 2) 2.15(2H t —CH$_2$CN—11)

1.90(2H broad —CNCH$_2$CH$_2$CH$_2$CH$_2$CH—)

1.50(10H m 8, 9, 10 NCH$_2$CH$_2$CH$_2$CH$_2$CH)

Example 41

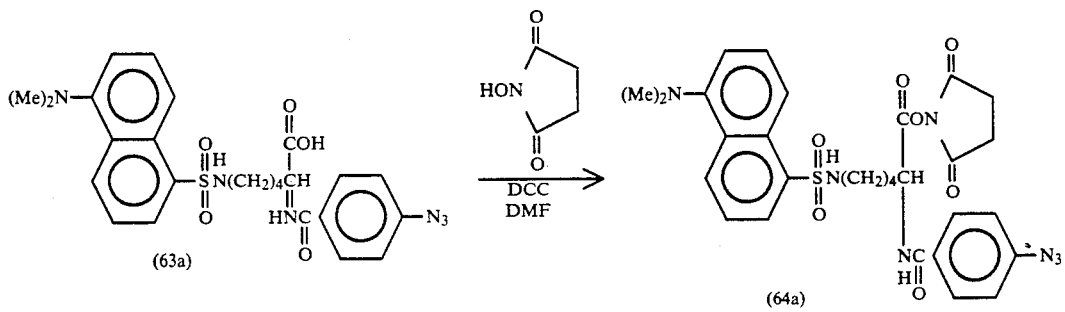

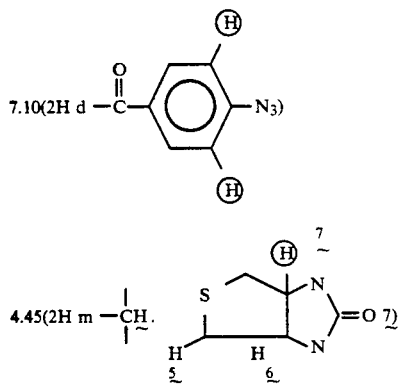

7.10(2H d)

4.45(2H m —CH·)

0.050 g (0.085 mmol) of a carboxylic acid was dissolved in 1 ml of anhydrous DMF. 0.012 g (0.105 mmol) of HOSu and 0.020 g (0.095 mmol) of DCC were added, and reaction was then carried out at room temperature for 10 hours. After the reaction, the resultant precipitate was filtered, and DMF was distilled off under reduced pressure by means of a vacuum pump. 0.060 g of the residue was led to a next reaction without isolation and purification.

IR (nujol) 3900, 2950, 2850, 2100, 1800, 1780, 1730, 1680, 1600, 1480, 1440, 1360, 1280, 1200, 1070, 840, 750 cm$^{-1}$.

Example 42

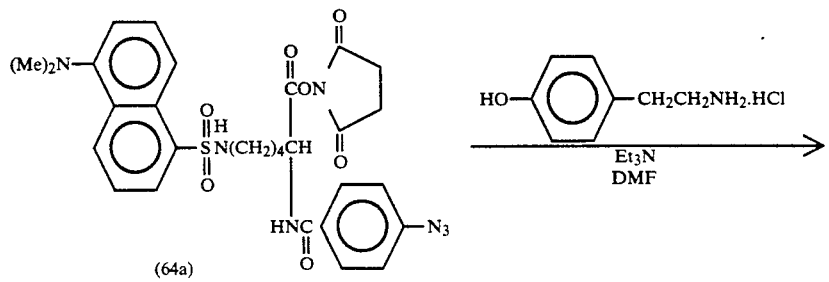

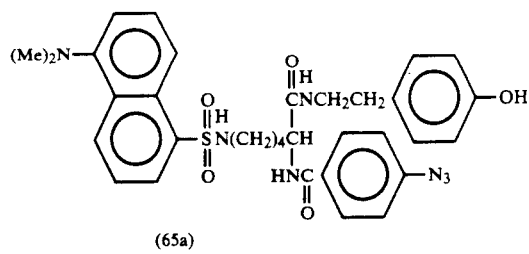

(65a)

0.060 g (0.095 mmol) of an imide ester was dissolved in 1 ml of anhydrous DMF. 0.016 g (0.095 mmol) of tyramine.hydrochloride and 0.014 g (0.143 mmol) of Et₃N were added to the solution and reaction was then carried out at room temperature for 12 hours. After completion of the reaction, DMF was distilled off under reduced pressure by means of a vacuum pump. CH₂Cl₂ was added to the residue and extraction was then performed, and the extract was washed with water, an aqueous saturated NaHCO₃ solution and water, dried over MgSO₄, and filtered. Next, CH₂Cl₂ was distilled off, and the residue was subjected to a column chromatography (silica gel; eluting solvent of CHCl₃ and MeOH in a ratio of 7:1), and 0.030 g of a product was obtained in a yield of 50%.

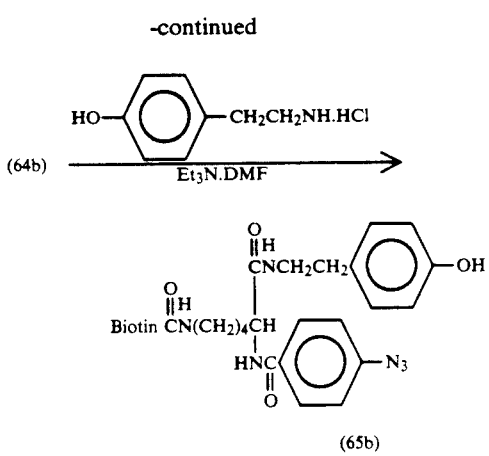

(65b)

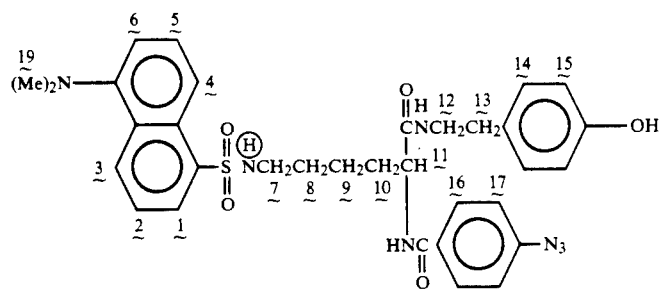

$^1$H-NMR (DMSO-d₆ 270 MHz), 8.52 (1H d $\underline{1}$), 8.29 (1H d $\underline{4}$), 8.15 (1H d $\underline{3}$), 7.85 (2H d $\underline{16}$), 7.45 (2H m $\underline{2}$, $\underline{5}$), 7.20 (1H d $\underline{6}$), 7.05 (2H d $\underline{15}$), 7.00 (2H d $\underline{17}$), 6.75 (2H d $\underline{14}$), 5.60 (1H broad $\underline{18}$), 4.65 (1H broad $\underline{11}$), 3.40 (2H t $\underline{12}$), 2.95 (8H s $\underline{19}$, $\underline{7}$), 2.65 (2H t $\underline{13}$), 1.85 (2H broad $\underline{10}$), 1.45 (4H broad $\underline{8}$, $\underline{9}$).

Example 43

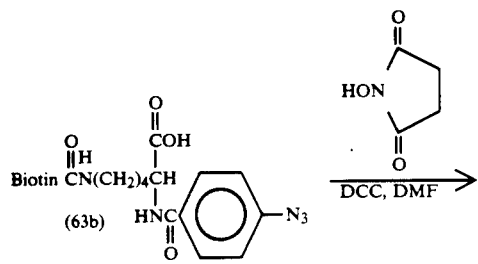

0.040 g (0.077 mmol) of a carboxylic acid was dissolved in 1 ml of anhydrous DMF. 0.010 g (0.084 mmol) of HOCu and 0.016 g (0.077 mmol) of DCC were added and reaction was then carried out at room temperature for 10 hours. After the reaction, the resultant precipitate was filtered, and DMF was distilled off under reduced pressure by means of a vacuum pump. 1 ml of anhydrous DMF was added to and dissolved in the residue. 0.013 g (0.077 mmol) of tyramine-hydrochloride and 0.012 g (0.116 mmol) of Et₃N were added to the solution and reaction was then carried out at room temperature for 15 hours. After completion of the reaction, DMF was distilled off, and the residue was subjected to a column chromatography (eluting solvent of CH₂Cl₂ and MeOH in a ratio of 7:1 to MeOH only), and 0.031 g of a product was obtained in a yield of 63%.

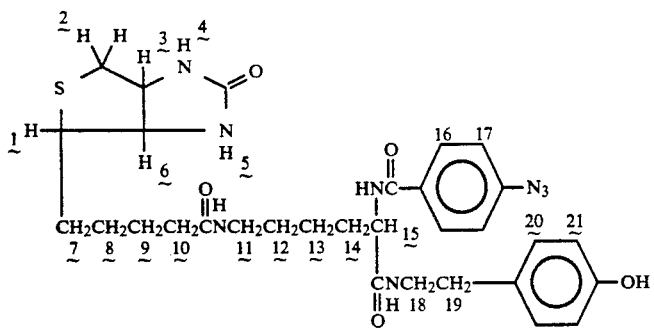

$^1$H-NMR (DMSO-d$_6$ 270 MHz), 8.21 (1H d 4), 8.00 (2H d 16), 7.53 (1H broad 5), 7.10 (2H d 17), 7.05 (2H d 20), 6.85 (2H d 20), 4.45 (2H m 3, 15), 4.25 (1H broad 6), 3.40 (2H t 18), 3.10 (3H m 11, 1), 2.75~3.0 (4H m 2, 19), 2.10 (2H t 10), 1.35~1.80 (12H m 7, 8, 9, 12, 13, 14).

Example 44

8-O-benzyloxymethyl-9,0-(nitrobenzoyl)-2,4,10-trioxycyclo(3,3,1,1$^{3.7}$)decane-6-ol (103)

A compound 102 (652.6 mg, 2.200 mmol) was azeotroped with anhydrous benzene and then dissolved in anhydrous pyridine under a nitrogen atmosphere. p-nitrobenzoyl chloride (119.8 mg, 2.240 mmol) and a catalytic amount of 4-dimethylaminopyridine were added at 0° C., and the solution was then stirred at room temperature for 2 hours.

Extraction was made with ether, and the resultant extract was washed with water, an aqueous saturated potassium sulfate solution, an aqueous saturated sodium hydrogencarbonate solution and an aqueous saturated sodium chloride solution. Anhydrous magnesium sulfate was added to the resultant organic layer to dry it, and after filtration and concentration, a residue was isolated by a column chromatography (ethyl acetate/hexane=½) to obtain a compound 103.

Compound 103
Yield: 763.6 mg (78%).
Rf value: 0.45 (ethyl acetate/hexane=1/1).
$^1$H-NMR (δ in CDCl$_3$, 90 MHz). 4.05–4.65 (6H, m, H$_1$-H$_6$), 4.95 (2H, s, PhCH$_2$), 5.45 (1H, s, CH), 7.23 (5H, s, Ph), 8.20 (4H, s, PhCO).
IR 3420, 2900, 1700, 1590, 1510, 1440, 1360, 1335, 1255, 1150, 1120, 1090, 1080, 1035, 990, 940, 920, 840, 740, 710, 690 cm$^{-1}$.

Example 45

8-benzyloxymethyl-9-(4-nitrobenzyl)-6-benzyl-2,4,10-trioxatricyclo(3,3,1,1$^{5.7}$)decanal (110)

A compound 103 (853.6 mg, 1.92 mmol) was azeotroped with anhydrous benzene and then dissolved in N,N-dimethylformamide under a nitrogen atmosphere. Next, silver oxide (I) (2222.4 mg, 9.59 mmol) and benzyl bromide (2.28 ml, 19.2 mmol) were added, and the solution was then stirred at room temperature overnight. Extraction was effected with ethyl acetate, and the extract was washed with water, a 1N HCl solution, an aqueous saturated sodium hydrogencarbonate solution and an aqueous saturated sodium chloride solution. Anhydrous magnesium sulfate was added to the resultant organic layer to dry it, and after filtration and concentration, a residue was isolated by a column chromatography (ether/hexane=¼) to obtain a compound 110.

Compound 110

Yield: 479.6 mg (47%).
Rf value: 0.6 (ethyl acetate/hexane=¼).
$^1$H-NMR (δ in CDCl$_3$, 90 MHz), 4.10–4.30 (5H, m, H1-H6), 4.40 (4H, s, PhCH$_2$), 5.07 (1H, s, CH), 5.35 (1H, t, H$_2$), 7.10 (10H, Ph), 8.10 (4H, m, PhCO).

Example 46

2-(4-nitrobenzoyl)-6-benzyl-myoinositol (111)

A compound 110 (278.0 mg, 0.519 mmol) was dissolved in a small amount of anhydrous dichloromethane, and a 5M HCl/anhydrous MeOH solution (25 ml) was added at 0° C. and the solution was then stirred at room temperature overnight. Next, decantation was effected by the use of methanol, followed by distilling off. A residue was isolated by a column chromatography (methanol/dichloromethane=1/20) to obtain a compound 111.

Compound 111
Yield: 139.2 mg (66%)
Rf value: 0.18 (MeOH/CH$_2$Cl$_2$=1/10)
$^1$H-NMR (δ in CD$_3$OD+CDCl$_3$, 270 MHz), 3.50 (4H, m), 4.15 (1H, m), 4.75 (2H, s, PhCH$_2$), 5.50 (1H, m, H$_2$), 7.20 (5H, s, Ph), 8.05 (4H, d, PhCO).

Example 47

2-(4-nitrobenzoyl)-6-benzyl-1',5'-dihydro-(2',4',3'-benzodioxaphosphepinyl)myoinositol (112)

Tetrazole (264.1 mg, 3.769 mmol) was added to a compound 111 (127.3 mg, 0.314 mmol) at 0° C. under a nitrogen atmosphere, and the solution was then suspended in anhydrous dichloromethane. Furthermore, 1,5-dihydro-3-diethylamino-2,4,3-benzodioxaphosphenpiane (450.9 mg, 1.885 mmol) was added to the suspension, followed by stirring at room temperature for 30 minutes. Water was added at room temperature, and after stirring for 10 minutes, the solution was cooled to −42° C. Next, m-chloroperbenzoic acid (542.1 mg, 2.513 mmol) was added, followed by stirring at 0° C. for 30 minutes. Extraction was effected with dichloromethane, and the extract was washed with a 10% aqueous sodium sulfite solution, an aqueous saturated sodium hydrogencarbonate solution, water and an aqueous saturated sodium chloride solution in this order. Anhydrous sodium sulfate was added to the resultant organic layer, followed by drying. After filtration and concentration, the residue was purified by a column chromatography (ethyl acetate/hexane=½ and methanol/dichloromethane=1/30) to obtain a compound 112.

Compound 112
Yield: 341.8 mg (95%)
Rf value: 0.43 (MeOH/CH$_2$Cl$_2$=1/10)
$^1$H-NMR (δ in CDCl$_3$, 90 MHz), 4.30–5.50 (24H, m), 7.0 (21H, m), 8.0 (4H, d).

IR 3370, 2900, 2850, 1725, 1500, 1440, 1360, 1250, 1140, 1000, 830, 720 cm⁻¹.

Example 48

2-(4-aminobenzoyl)myoinositol-1,3,4,5-triphosphate (113)

A mixed solvent of methanol water=4/1 (v/v) and a small amount of dichloromethane chloride were added to and dissolved in a compound 112 (271.7 mg, 0.237 mmol), and 2 spatulas of 5% palladium-carbon were added. The solution was stirred, and hydrogenation replacement was then carried out under reduced pressure. The solution was stirred at room temperature for 24 hours, filtered and then washed with water sufficiently. The resultant filtrate was concentrated, and the residue was then purified by a cellulose column (CC-31, n-PrOH/conc. NH₃ aq./H₂O=5/4/1) to obtain a compound 113.

Compound 113
Yield: 79.9 mg (50%)
Rf value: 0.17 (n-PrOH/conc. NH₃ aq./H₂O=5/4/1)
¹H-NMR (δ in D₂O, 270 MHz), 3.93 (1H, t, H₆), 4.07 (1H, dt, H₁), 4.10 (1H, m, H₅), 4.15 (1H, dt, H₃), 4.39 (1H, q, H₄), 5.70 (1H, t, H₂), 6.69 (2H, d), 7.79 (2H, d).

Example 49

1 g of a gel (activated CH Sepharose 4B) was weighed accurately, and tyramine (1.56 mg, 9 μmol) was dissolved with the aid of a coupling buffer (a 0.1M NaHCO₃ solution containing 0.5M NaCl) (6 ml) in a test tube, followed by shaking for 1 hour. Simultaneously, a compound 113 (4.05 mg, 6 μmol) was dissolved in water (500 μl), and concentrated hydrochloric acid (2 μl) was added. Under acidic conditions, sodium nitrite (0.92 mg, 1.2×10⁻² mmol) was added, followed by stirring. After the stirring for 1 hour, blue violet was confirmed by a potassium iodide starch test paper, and the resultant diazonium salt was collected. This diazonium salt was added to the gel in the test tube and then washed with a small amount of a coupling buffer (gel/coupling buffer=3 ml/6 ml), and the solution was then shaken at room temperature for 1 hour. Next, the solution was transferred onto a glass filter (G3), and an excess ligand was then washed several times with a solution of a 0.05M trishydrochloric acid buffer (pH 8.0, containing 0.5M NaCl) and a 0.05M formic acid buffer (pH 4.0, containing 0.5M NaCl) alternately. After drying, a gel 114 was collected and then preserved in an icebox.

Example 50

A compound 113 (14.9 mg, 0.0221 mmol) was added to water (3.75 ml), and reaction was then carried out at 60° C. for 2 hours under a hydrogen pressure of 80 atm in an autoclave. The catalyst was removed by filtration, and water was then distilled off under reduced pressure. The resultant residue was purified by a cellulose column (n-PrOH/conc. NH₃ aq./H₂O=5/4/1) to obtain a compound 115.

Compound 115
Yield: 14.3 mg (96.8%)
Rf value: 0.24 (n-PrOH/conc. NH₃ aq./H₂O=5/5/1)
¹H-NMR (δ in D₂O, 270 MHz)

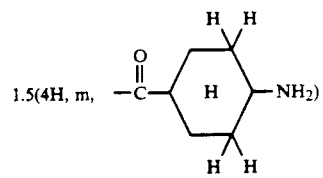
1.5(4H, m,

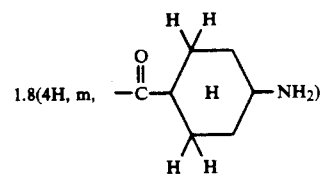
1.8(4H, m,

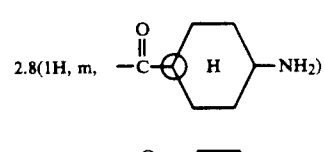
2.8(1H, m,

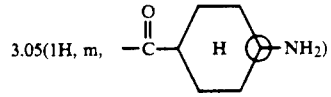
3.05(1H, m, 3.7–4.3 (5H, m, H₁–H₆), 5.6 (1H, m, H₂).

Example 51

A compound 113 (10.6 mg, 0.0157 mmol) was dissolved in water (1.1), and concentrated hydrochloric acid (9.7 μl, 0.315 mmol) was added at 0° C., followed by stirring. Sodium nitrite (2.4 mg, 0.0315 mmol) was added to the resultant suspension, followed by stirring. Next, sodium azide (2.3 mg, 0.0315 mmol) was added. After reaction for 2 hours, the solvent was distilled off under reduced pressure, and isolation was carried out by the use of a cellulose column (n-PrOH/conc. NH₃ aq./H₂O=5/4/1) to obtain a compound 116.

Compound 116
Yield: 7.6 mg (69%)
Rf value: 0.36 (n-PrOH/conc. NH₃ aq./H₂O=5/5/1)
¹H-NMR (δ in D₂O, 270 MHz), 3.9–4.5 (5H, m, H₁–H₆), 5.8 (1H, s, H₂),

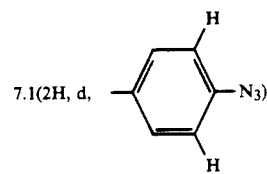
7.1(2H, d,

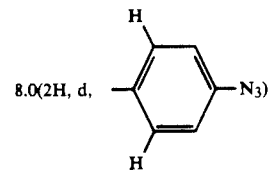
8.0(2H, d,

Example 52

1 g of a gel (activated CH Sepharose 4B) was weighed accurately and then swollen and washed on a glass filter (G3) by the use of a 1 mM HCl solution (200 ml). A ligand 115 (5.8 mg, 8.7 μmol) was dissolved in 6 ml of a coupling buffer (0.1M NaHCO₃, pH 8.3). The gel was rapidly washed with this buffer, and the gel suspension and the ligand solution were shaken at room temperature for 1 hour. The resultant solution was transferred onto the glass filter (G3), and the excess ligand was then washed several times with a solution of a 0.05M trishydrochloric acid buffer (pH 8.0, containing 0.5M NaCl) and a 0.05M formic acid buffer (pH 4.0, containing 0.5M NaCl) alternately. After drying, a gel 116 was collected and then preserved in an icebox.

Example 53

1 g of a gel (epoxy-activated Sepharose 6B) was weighed accurately and then swollen and washed on a glass filter (G3) by the use of distilled water (100 ml). A ligand 115 (4.1 mg) was dissolved in distilled water (500 μl). The gel suspension was rapidly washed with this buffer, transferred into a test tube, and then shaken at a pH of 9 for 16 hours to achieve reaction. Afterward, the reaction solution was transferred onto the glass filter (G3), and the excess ligand was then washed several times with distilled water, a carbonic acid buffer (0.1M NaHCO$_3$, pH 8.0) and an aqueous acetic acid solution (0.1M CH$_3$COOH, pH 4) alternately. Next, the solution was allowed to stand in 1M ethanolamine for 4 hours to block an active group. Afterward, the dried gel 118 was collected and then preserved in an icebox.

Example 54

3,4-di-O-(4-methoxybenzyl)-1,2:5,6-di-O-cyclohexylidene-myoinositol (122)

A compound 121 (452.8 mg, 1.33 mmol) was azeotroped with benzene and then dissolved in N,N-dimethylformamide (7 ml). The solution was reacted with 50% sodium hydride (140.6 mg, 2.93 mmol) and p-methoxybenzyl chloride (452 μl, 3.33 mmol) at 0° C. overnight. Extraction was effected with ether, and the solution was then washed with a saturated sodium chloride solution (7 times). Anhydrous sodium sulfate was added to the organic layer to dry the same, followed by concentrating under reduced pressure. Isolation was effected by the use of a flush column (ethyl acetate/hexane=1/9 to 1/4) to obtain a compound 122.

Compound 122
Yield: 632.6 mg (82%).
Rf value: 0.35 (ethyl acetate/hexane=¼).
$^1$H-NMR (δ in CDCl$_3$, 90 MHz). 1.10–1 90 (b, C$_6$H$_{10}$, 20H), 3.20–4.30 (m, ring H, 6H), 3.78 (s, —OCH$_3$, 6H), 4.70–4.81 (m, —CH$_2$—Ph, 4H),

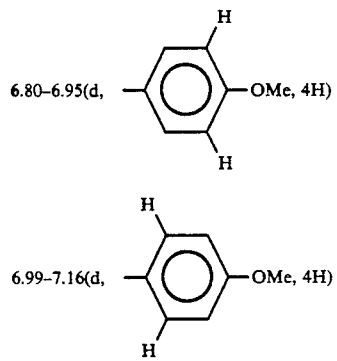

Example 55

3,4-di-O-(4-methoxybenzyl)-1,2-O-cyclohexylidenemyoinositol (123)

A compound 122 (142.8 mg, 0.246 mmol) was azeotroped with benzene and then sealed hermetically. Next, a 0.5% I$_2$/MeOH solution (1.75 ml) was added to the solution at room temperature, and stirring was done for 3 hours, while the reaction system was observed carefully. After completion of the reaction, a solution prepared by dissolving sodium sulfite.pentahydrate in water was added dropwise to the system to reduce iodine. Extraction was effected with ethyl acetate, and the solution was then washed with a saturated sodium hydrogencarbonate solution and a saturated sodium chloride solution (twice). Next, the resultant organic layer was dried over anhydrous magnesium sulfate. After filtration and concentration, isolation was effected by the use of a flush column (ethyl acetate/hexane=1/1) to obtain a compound 123.

Compound 123
Yield: 309.6 mg (74%)
Rf value: 0.43 (MeOH/CH$_2$Cl$_2$=1/10)
$^1$H-NMR (δ in CDCl$_3$, 90 MHz) 1.13–1.85 (b, C$_6$H$_{10}$, 10H), 2.50–2.75 (m, —OH, 2H), 3.20–4.80 (m, ring H, 6H), 3.62 (s, —OCH$_3$, 6H), 4.45–4.80 (m, —CH$_2$—Ph, 4H),

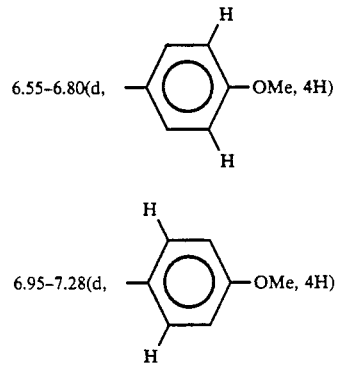

Example 56

3,4-di-O-(4-methoxybenzyl)-5,6-di-O-benzyl-1,2-O-cyclohexylidene-myoinositol (124)

A compound 123 (309.6 mg, 0.618 mmol) was azeotroped with benzene and then was dissolved in N,N-dimethylformamide (5 ml) under a nitrogen atmosphere. Next, benzylchloride (164 μl, 1.42 mmol) and 50% sodium hydride (65.3 mg, 1.36 mmol) were added, and the temperature of the solution was elevated up to 40° C., followed by stirring for 2.5 hours. Extraction was effected with ether, and the solution was then washed with a saturated sodium chloride solution (7 times). The organic layer was dried over anhydrous sodium sulfate, and after filtration and concentration, isolation was effected by the use of a flush column (ethyl acetate/hexane=1/6) to obtain a compound 124.

Compound 124
Yield: 361.1 mg (87%)
Rf value: 0.54 (methyl acetate/hexane=½)
$^1$H-NMR (δ in CDCl$_3$, 90 MHz),
1.37–1.80 (b, C$_6$H$_{10}$, 10H),
3.25–4.25 (m, ring H, 6H),
3.78 (s, —OCH$_3$, 6H), 4.45–4.97 (m, —CH$_2$—Ph, 8H),

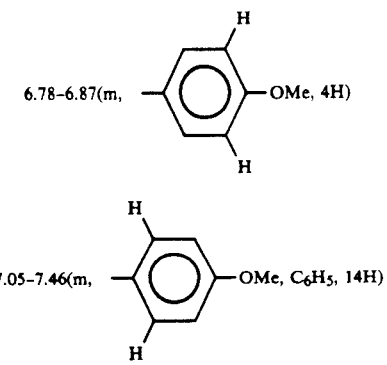

Example 57

3,4-di-O-(4-methoxybenzyl)-5,6-di-O-benzyl-myoinositol (125)

A compound 124 (367.1 mg, 0.539 mmol) was azeotroped with benzene and then dissolved in a small amount of dichloromethane while sealed hermetically. Furthermore, a 0.1M HCl/MeOH solution (5 ml) was added at 0° C., followed by stirring for 4 hours. The solvent was then distilled off under reduced pressure. The resultant residue was purified by the use of a flush column (ethyl acetate/hexane=½) to obtain a compound 125.

Compound 125
Yield: 165.1 mg (51%)
Rf value: 0.45 (methyl acetate/hexane=2/1)
$^1$H-NMR ($\delta$ in CDCl$_3$, 90 MHz), 2.60 (m, OH, 2H), 3.32–4.12 (m, ring H, 6H), 3.80 (s, —OCH$_3$, 6H), 4.62–5.00 (m, —CH$_2$—Ph, 8H),

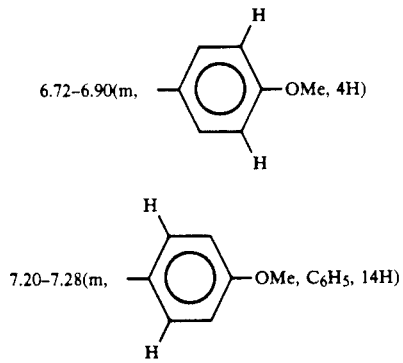

Example 58

1-O-methoxymethyl-3,4-di-O-(4-methoxybenzyl)-5,6-di-O-benzyl-myoinositol (126)

A compound 125 (165.1 mg, 0.275 mmol) was azeotroped with benzene and then dissolved in anhydrous methanol. Reaction was carried out in a distillation column provided with a calcium chloride tube. Next, n-dibutyltin oxide (75.5 mg, 0.304 mmol) was acted on the reaction solution at room temperature, and the solution was then refluxed for 2 hours and methanol was distilled off 2 or 3 times. Afterward, methanol was distilled off completely, and the residue was then dissolved in N,N-dimethylformamide. Outside the system, p-methoxymethyl chloride (132 µl) and triethylamine (244 µl) were added thereto to form a salt, and this salt was then added to the reaction system, followed by heating at 60° C. for 6 hours. After completion of the reaction, potassium fluoride dissolved in water was added. Extraction was effected with ethyl acetate, and the extract was then washed with a saturated sodium chloride solution (5 times). The organic layer was dried over anhydrous sodium sulfate. After distilling off under reduced pressure, the resultant residue was purified by the use of a thin-layer chromatography (ethyl acetate/hexane=⅓, twice) to obtain a compound 126.

Compound 126
Yield: 42.4 mg (24%).
Rf value: 0.42 (ethyl acetate/hexane=½).

Example 59

1-O-methoxymethyl-2-O-(4-nitrobenzoyl)-3,4-di-O-(methoxybenzyl)-5,6-di-O-benzyl-myoinositol (127)

A compound 126 (42.4 mg, 0.0706 mmol) was azeotroped with benzene and then dissolved in pyridine under a nitrogen atmosphere. p-nitrobenzoyl chloride (14.4 mg, 0.0776 mmol) and a catalytic amount of 4-dimethylaminopyridine were added at 0° C., followed by stirring at room temperature for 3 hours. Extraction was effected with ethyl acetate, and the extract was then washed with an aqueous saturated potassium hydrogensulfate solution (twice), a saturated sodium hydrogencarbonate solution and a saturated sodium chloride solution (twice). Next, the resultant organic layer was dried over anhydrous magnesium sulfate. After filtration and concentration, the residue was purified by the use of a thin-layer chromatography (ethyl acetate/hexane=½) to obtain a compound 127.

Compound 127
Yield: 41.6 mg (79%)
Rf value: 0.41 (ethyl acetate/hexane=½)
$^1$H-NMR ($\delta$ in CDCl$_3$, 90 MHz), 3.35–3.70 (m, ring H, 5H), 3.80 (s, —OCH$_3$, 9H), 4.69–4.95 (m, —CH$_2$—Ph, 10H), 5.90 (t, H$_2$, 1H), 7.05–7.33 (m, Ph, 18H),

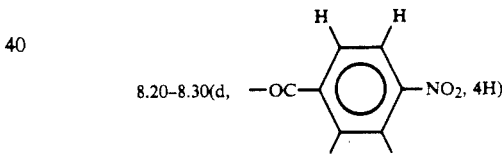

Example 60

2-O-(4-nitrobenzoyl)-5,6-di-O-benzyl-myoinositol (129)

A compound 127 (38.4 mg, 0.0555 mmol) was dissolved in dichloromethane/water=18/1 (v/v) at 0° C. Next, 2,3-dichloro-5,6-dicyano-1,4-benzoquinone (DDQ) (31.5 mg, 0.139 mmol) were added to the solution, followed by stirring for 7.5 hours. Extraction was effected with dichloromethane, and the extract was washed with a saturated sodium hydrogencarbonate solution (3 times) and a saturated sodium chloride solution. Afterward, the resultant organic layer was dried with anhydrous magnesium sulfate, and after filtration and concentration, a residue 128 was dissolved in a small amount of dichloromethane. A 5M HCl/MeOH solution (1 ml) was added, followed by stirring for 3 hours. After distilling off under reduced pressure, the residue was purified by the use of a thin-layer chromatography (ethyl acetate/hexane= 2/1) to obtain a compound 129.

Compound 129

Yield: 13.7 mg (58%)
Rf value: 0.36 (ethyl acetate/hexane=2/1)
1H-NMR (δ in CDCl$_3$+CD$_3$OD, 90 MHz) 3.38-3.89 (m, 5H, ring H), 4.70-4 83 (m, 4H, Ph—CH$_2$—), 5.55 (t, 1H, H$_2$), 7.05-7.30 (d, 1OH, Ph),

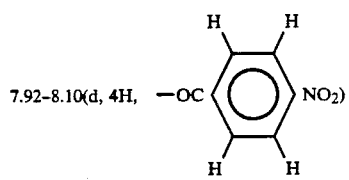

7.92-8.10(d, 4H, —OC—⟨⟩—NO$_2$)

Example 61

2-O-(4-nitrobenzoyl)-5,6-di-O-benzyl-myoinositol-1,3,4-tri-o-xylylene phosphate (130)

A compound 129 (14.3 mg, 0.309 mmol) was added to tetrazole (19.5 mg, 0.278 mmol) at 0° C. under a nitrogen atmosphere, and the solution was then suspended in anhydrous dichloromethane. 1,5-dihydro-3-diethylamino-2,4,3-benzodioxaphosphepine (33.3 mg, 0.139 mmol) was added to the suspension, and after stirring for 30 minutes at room temperature, water (100 μl) was added. Afterward, the solution was cooled to −42° C., and m-chloroperbenzoic acid (39.9 mg, 0.185 mmol) was added thereto, followed by stirring at 0° C. for 30 minutes. Extraction was effected with dichloromethane, and the extract was then washed with a 10% aqueous sodium sulfite solution, an aqueous saturated sodium hydrogencarbonate solution and an aqueous saturated sodium chloride solution in this order. Afterward, the organic layer was dried over anhydrous sodium sulfate, and after filtration and concentration, the residue was purified by the use of a thin-layer chromatography (methanol/dichloromethane=1/10) to obtain a compound 130.

Compound 130
Yield: 15.2 mg (95%).
Rf value: 0.43 (MeOH/CH$_2$Cl$_2$=1/10).

Example 62

2-O-(4-aminobenzoyl)-myoinositol-1,3,4-triphosphoric acid (131)

A mixed solvent of methanol/water=4/1 (v/v) and a small amount of dichloromethane chloride were added to and dissolved in a compound 130 (15.2 mg, 0.0151 mmol), and 2 spatulas of 5% palladium-carbon were added. Afterward, the solution was stirred, and hydrogenation replacement was then carried out under reduced pressure. The solution was stirred at room temperature for 24 hours and then filtered, followed by washing with water sufficiently. The resultant filtrate was concentrated, and the residue was then purified by a cellulose column (CC-31, n-PrOH/conc. NH$_3$ aq./H$_2$O=5/4/1) to obtain a compound 131.

Compound 131
Yield: 9.4 mg (quant)
Rf value: 0.28 (n-PrOH/conc. NH$_3$ aq./H$_2$O=5/4/1)
$^1$H-NMR (δ in D$_2$O, 270 MHz), 3.40 (t, 1H, H$_6$), 3.63 (t, 1H, H$_5$), 3.85-4.20 (m, 3H, H$_1$, H$_3$, H$_4$), 5.50 (s, 1H, H$_2$),

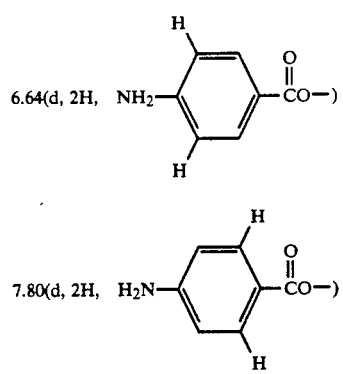

6.64(d, 2H, NH$_2$—⟨⟩—CO—)

7.80(d, 2H, H$_2$N—⟨⟩—CO—)

Example 63

1 g of a gel (activated CH Sepharose 4B) was weighed accurately, and tyramine (1.5 mg, 8.6 μmol) was dissolved with the aid of a coupling buffer (a 0.1M NaHCO$_3$ solution containing 0.5M NaCl) (6 ml) in a test tube, followed by shaking for 1 hour. Simultaneously, a compound 131 (about 4 mg, 6.7×10$^{-3}$ mmol) was dissolved in water (200 μl), and concentrated hydrochloric acid (2 μl) was added. Under acidic conditions, sodium nitrite (1 mg, 1.4×10$^{-2}$ mmol) was added, followed by stirring. After the stirring for 1 hour, blue violet was confirmed by a potassium iodide starch test paper, and the resultant diazonium salt was collected. This diazonium salt was added to the gel in the test tube and then washed with a small amount of a coupling buffer (gel/coupling buffer=3 ml/6 ml), and the solution was then shaken at room temperature for 1 hour. Next, the solution was transferred onto a glass filter (G3), and an excess ligand was then washed several times with a solution of a 0.05M trishydrochloric acid buffer (pH 8.0, containing 0.5M NaCl) and a 0.05M formic acid buffer (pH 4.0, containing 0.5M NaCl) alternately. After drying, a gel 132 was collected and then preserved in an icebox.

Example A IP$_3$-protein composite

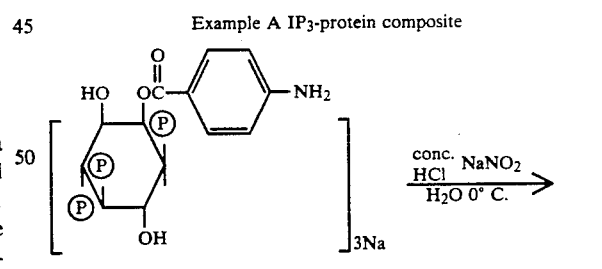

2-p-aminobenzoyl-IP$_3$ (1)

$\xrightarrow[\text{H}_2\text{O 0° C.}]{\text{conc. HCl  NaNO}_2}$ $\xrightarrow{\text{0.1 M NaHCO}_3}$ Example 64
$\xrightarrow{\text{BSA}}$ Example 65 IP$_3$-protein composite
$\xrightarrow{\text{MSA}}$ Example 66

Example 64

10 mg (0.016 mmol) of a compound (1) was dissolved in 2 ml of water. The solution was cooled with ice-water, and 0.025 ml (0.33 mmol) of a concentrated HCl solution was added thereto. After it was confirmed by a pH test paper that the solution was acidic, 2.2 mg (0.032 mmol) of $NaNO_2$ was added thereto, followed by stirring for a period of from 20 to 30 minutes. Violet was confirmed by a potassium iodide starch test paper, and a 0.1M aqueous $NaHCO_3$ solution was added for acidification. Next, 40 mg ($0.6 \times 10^{-3}$ mmol) of BSA (made by Sigma Co., Ltd.) was added to the solution, and reaction was then carried out for 3 days on ice-water or in an icebox. After completion of the reaction, this reaction solution is transferred to a dialysis membrane vessel, and dialysis is carried out for 4 days in the icebox. In this case, water was exchanged sometimes. In the last place, the reaction solution was removed by freeze-drying to obtain 48 mg of a product.

Example 65

Reaction was carried out by the same procedure as in Example 64 except that 40 mg of MSA (Organon Technika Co., Ltd.) was used in place of BSA in Example 64, thereby obtaining 47.6 mg of a product.

Example 66

10 mg (0.016 mmol) of a compound (1) was dissolved in 2 ml of water. The solution was cooled with ice-water, and 0.025 ml (0.33 mmol) of a concentrated HCl solution was added thereto. After it was confirmed by a pH test paper that the solution was acidic, 2.2 mg (0.032 mmol) of $NaNO_2$ was added thereto, followed by stirring for a period of from 20 to 30 minutes. Violet was confirmed by a potassium iodide starch test paper, and a 0.1M aqueous $NaHCO_3$ solution was added for acidification. Next, 40 mg of KLH (made by Sigma Co., Ltd.) was added to the solution, and reaction was then carried out for 3 days on ice-water or in an icebox. After completion of the reaction, this reaction solution is transferred to a dialysis membrane vessel, and dialysis is carried out for 4 days in the icebox. In this case, water was exchanged sometimes. In the last place, the reaction solution was removed by freeze-drying to obtain 47 mg of a product.

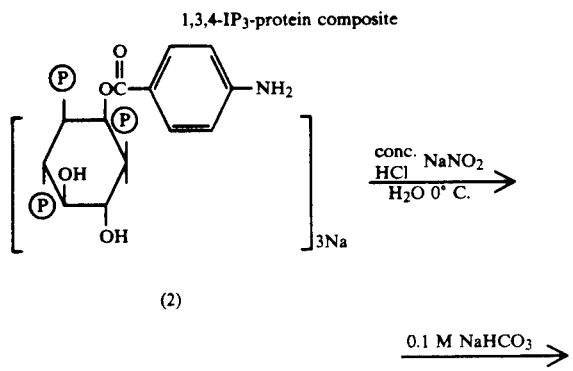

Example 67

1,3,4-IP$_3$-protein composite

Example 68 1,3,4-IP$_3$-protein composite

Example 69

Example 67

1 mg (0.00149 mmol) of a compound (2) was dissolved in 100 μl of water, and concentrated hydrochloric acid (0.5 μl, 0.0149 mmol) was added to the solution at 0° C. and sodium nitrite (0.23 mg, 0.00298 mmol) was acted on the solution under acidic conditions, followed by stirring for 15 minutes. After blue violet was confirmed by a potassium iodide starch test paper, the solution was neutralized with a 0.1M aqueous $NaHCO_3$ solution (pH 8.3). Next, 30 mg ($0.45 \times 10^{-3}$ mmol) of BSA was dissolved in 0.5 ml of water, and the solution was then added to the system, followed by stirring for 19 hours while a temperature of 0° C. was maintained. This reaction solution is transferred to a dialysis membrane vessel, and dialysis is carried out for 48 hours in water (200 ml × 2) in an icebox to achieve purification. The reaction solution was transferred into an egg-plant type flask (50 ml) and then lyophilized to obtain 28.6 mg of a purified product, i.e., 1,3,4-IP$_3$-protein (BSA) composite.

Example 68

Reaction was carried out by the same procedure as in Example 67 except that BSA of Example 67 was replaced with 30 mg of MSA, thereby obtaining 28 mg of a product.

Example 69

0.5 mg (0.00075 mmol) of a compound (2) was dissolved in 100 μl of water, and concentrated hydrochloric acid (0.25 μl) was added at 0° C. Next, sodium nitrite (0.12 mg, 0.00149 mmol) was dissolved in 50 μl of water under acidic conditions to carry out reaction, followed by stirring for 15 minutes. After blue violet was confirmed by a potassium iodide starch test paper, the solution was neutralized with a 0.1M aqueous $NaHCO_3$ solution (pH 8.3). Afterward, 2 ml of water was added to 1/5 of this reaction solution [containing 0.1 mg of a compound (2)], and 13.9 mg of KLH was further added thereto, followed by stirring at 0° C. for 21 hours. This reaction solution is transferred to a dialysis membrane vessel, and dialysis is carried out for 72 hours in water (200 ml × 2) in an icebox to achieve purification. The reaction solution was transferred into an egg-plant type flask (30 ml) and then lyophilized to obtain 1,3,4-IP$_3$-protein composite (10.1 mg). IP$_4$-protein composite

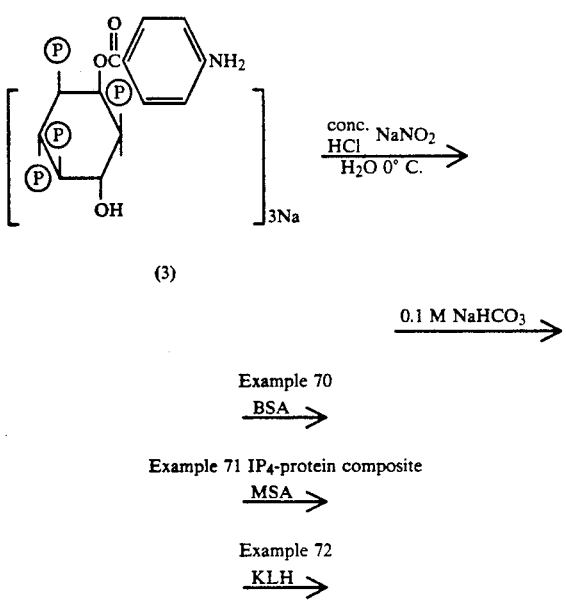

(3)

$\xrightarrow{\text{0.1 M NaHCO}_3}$

Example 70
$\xrightarrow{\text{BSA}}$

Example 71 IP₄-protein composite
$\xrightarrow{\text{MSA}}$

Example 72
$\xrightarrow{\text{KLH}}$

Example 70

1 mg (0.00149 mmol) of a compound (3) was dissolved in 1 ml of H₂O. The solution was cooled with ice-water, and 0.5 μl (0.0149 mmol) of a concentrated HCl solution was added thereto. After it was confirmed by a pH test paper that the solution was acidic, 2.23 mg (0.0030 mmol) of NaNO₂ was added thereto, followed by stirring for a period of from 20 to 30 minutes. Violet was confirmed by a potassium iodide starch test paper, and a 0.1M aqueous NaHCO₃ solution was then added for alkalinization. Next, 30 mg of BSA was added to the solution, and reaction was then carried out for 3 days in an icebox. After completion of the reaction, this reaction solution is transferred to a dialysis membrane vessel, and dialysis is carried out for 4 days in the icebox. In this case, water was exchanged sometimes. In the last place, the reaction solution was removed by freeze-drying to obtain 28.6 mg of a product.

Example 71

Reaction was carried out by the same procedure as in Example 70 except that BSA of Example 70 was replaced with 30 mg of MSA, thereby obtaining 28.1 mg of a product.

Example 72

0.5 mg of a compound (3) was dissolved in 0.1 ml of water. The solution was cooled with ice-water, and a concentrated hydrochloric acid solution (0.25 μl) was added. After it was confirmed by a pH test paper that the solution was acidic, 0.12 mg of NaNO₂ was added thereto, followed by stirring for a period of from 20 to 30 minutes. Violet was confirmed by a potassium iodide starch test paper, and a 0.1M aqueous NaHCO₃ solution was then added for alkalinization. Next, 13.9 mg of KLH and 2 ml of water were added to the solution, and reaction was then carried out for 3 days in an icebox. After completion of the reaction, this reaction solution is transferred to a dialysis membrane vessel, and dialysis is carried out for 4 days in the icebox. In this case, water was exchanged sometimes. In the last place, the reaction solution was removed by freeze-drying to obtain 10.2 mg of a product.

Experimental Example 1 Interaction with IP₃-5-phosphatase

Activities of IP₃-5-phosphatase of human red cell ghosts and a cytosol extracted from a rat brain were measured. The red cell ghosts were collected from a human blood in accordance with a Downes et al.'s method [Downes, C. P. et al.; Biochem. J., 203, 169-177 (1982)], and an enzyme activity was measured by two methods. One of the two methods is described in the above-mentioned Downes et al.'s literature, and in this method, the measurement was made on the basis of a radiation chemistry. Another method comprises incubating 0.1 mM of an IP₃ compound and red cell ghosts (not more than 0.5 mg) or a cytosol (22 μg) extracted from a rat brain, and then measuring free inorganic phosphorus in accordance with a Youngburg et al.'s method [Youngburg, G. E. and Youngburg, M. V.; J. Lab. Clin. Med., 16, 158-168 (1930)].

[$^{32}$P]IP₃ (specific radioactivity to 2000 Ci/mmol) was available from Amersham Co., Ltd. A phosphoinositide fraction made by Sigma Co., Ltd. which was a control was subjected to alkaline fission in accordance with a Grads and Ballou's method [Grads, C. and Ballou, C. E.; J. Biol. Chem., 236, 54-60 (1961)], and then purified with HPLC by the use of an SAX column. The thus purified phosphoinositide fraction was used. The results are set forth in Table 1.

TABLE 1

| | Interaction with IP₃-5-phosphatase | | | |
|---|---|---|---|---|
| | Red Cell Ghosts | | Cytosol Extracted from Brain | |
| Compound | Ki | Hydrolyzed Amount | Ki | Hydrolyzed Amount |
| Compound of 8DL | 2.1[a]μM | 1.7[b]nmol | 15.6[a]μM | 3.6[c]nmol |
| Compound of 6 DL | 3.0 | 3.8 | ND[d] | 11.8 |
| Compound of 9DL (R'' = benzene) | 5.6 | 4.8 | ND | 4.1 |
| IP₃ | 14.2 | 16.7 | 57 | 12.5 |
| Compound of 7DL | 16 | 9.6 | 52.7 | 5.6 |

[a]Ki values were calculated from a Lineweaver-Burk plot. Each value was an average of two experiments.
[b]Incubation was made at 37° C. for 60 minutes.
[c]Incubation was made at 37° C. for 10 minutes. Each value was an average of three experiments.
[d]No experiment was done.

Experimental Example 2 Interaction with IP₃-3-kinase

The forebrain of a rat was placed in a solution containing 50 mM of sodium chloride, 10 mM of a Hepes buffer solution (pH 7.4) and 10 mM of β-mercaptoethanol, and then homogenized by a Dounce homogenizer. Next, the homogenized material was then centrifuged under 100,000 g for 60 minutes to obtain a supernatant which was a cytosol. Enzyme activity was measured in accordance with a procedure reported by one of the present inventors [Yamaguchi K., Hirata M. et al.; Biochem. J., 244, 787-791 (1987) and Kimura, Y., Hirata, M. et al.; Arch. Biochem. Biophys., 257, 363-369 (1987)]. [$^3$H]IP₃ (specific radioactivity 17 Ci/mmol or 1 Ci/mmol) was available from Amersham Co., Ltd. The results are set forth in Table 2.

TABLE 2

| | Interaction with $IP_3$-3-kinase | |
|---|---|---|
| | Ki $\mu$M | |
| Compound | <0.01 $\mu$M of $C^{2+}$ | 17 $\mu$M of $C^{2+}$ |
| $IP_3$ | 1.0 | 0.99 |
| Compound of 9OL (R" = benzene) | 0.36 | 2.0 |
| Compound of 6DL | 2.4 | 33.9 |

Ki values (which were factors for inhibiting the phosphorylation of [$^3$HIP$_3$]) were calculated from a Lineweaver-Burk plot. Each value was an average of two experiments.

Experimental Example 3

Influence on $IP_3$ bond ability and $Ca^{2+}$ liberation ability

The microsome of a rat cerebellum was prepared in accordance with a Worley et al.'s method [Worley, P. F. et al.; Nature, 325, 159-161 (1987)], and [$^3$H]IP$_3$ bond to the microsome was measured. Furthermore, the binding assay of [$^3$H]IP$_3$ was effected by the use of a kit (TRK.1000) made by Amersham Co., Ltd. in which the microsome faction of bovine adrenal cortex was used. On the other hand, a saponin treatment was carried out in accordance with a procedure reported by one of the present inventors [Hirata, M. et al.; Mol. Pharmacol., 23, 7814 85 (1983)] to obtain peritoneal macrophages of a guinea pig in which plasma membranes were permeable, and the incorporation and liberation of $Ca^{2+}$ were inspected in accordance with a separately reported procedure [Hirata, M. et al.; Biochem. J. 223, 229-236 (1984)]. The results are set forth in Table 3.

TABLE 3

| | Influence on $IP_3$ bond ability and $Ca^{2+}$ liberation ability | | |
|---|---|---|---|
| | $IP_3$ Bond Ability $IC_{50}{}^a$ | | Ca Limeration Ability $EC_{50}$ |
| Compound | Rat Cerebellum | Kit Made by Amersham Co., Ltd. | |
| $IP_3$ | $15^{nM}$ | $1.4^{nM}$ | $0.2^{uM}$ |
| Compound of 8DL | 95 | 5 | 0.9 |
| Compound of 9DL | 55 | 6.8 | 0.3 |
| Compound of 7DL | 85 | 4.2 | 1.6 |
| Compound of 6DL | 44 | 3 | 1.2 |

$^a$An inhibition activity to [$^3$H]IP$_3$ bond ability. Each value was an average of two experiments.

Experimental Example 4

Separation.purification of $IP_3$-5-phosphatase, $IP_3$-3-kinase and $IP_3$-bonded protein by the use of compounds 10D' and 11D'

Figure 6:
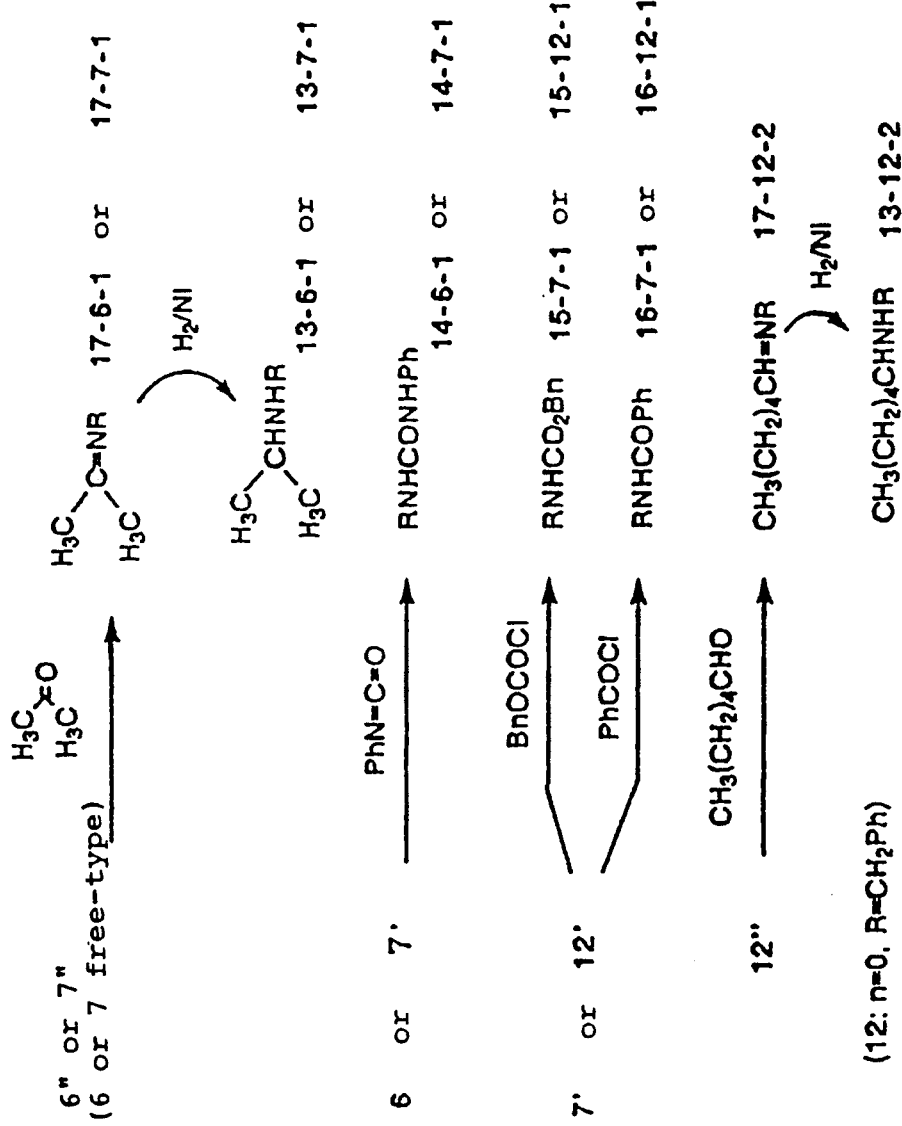
FIG. 6 shows typical examples of the reactions in FIG. 5.
Figure 7:
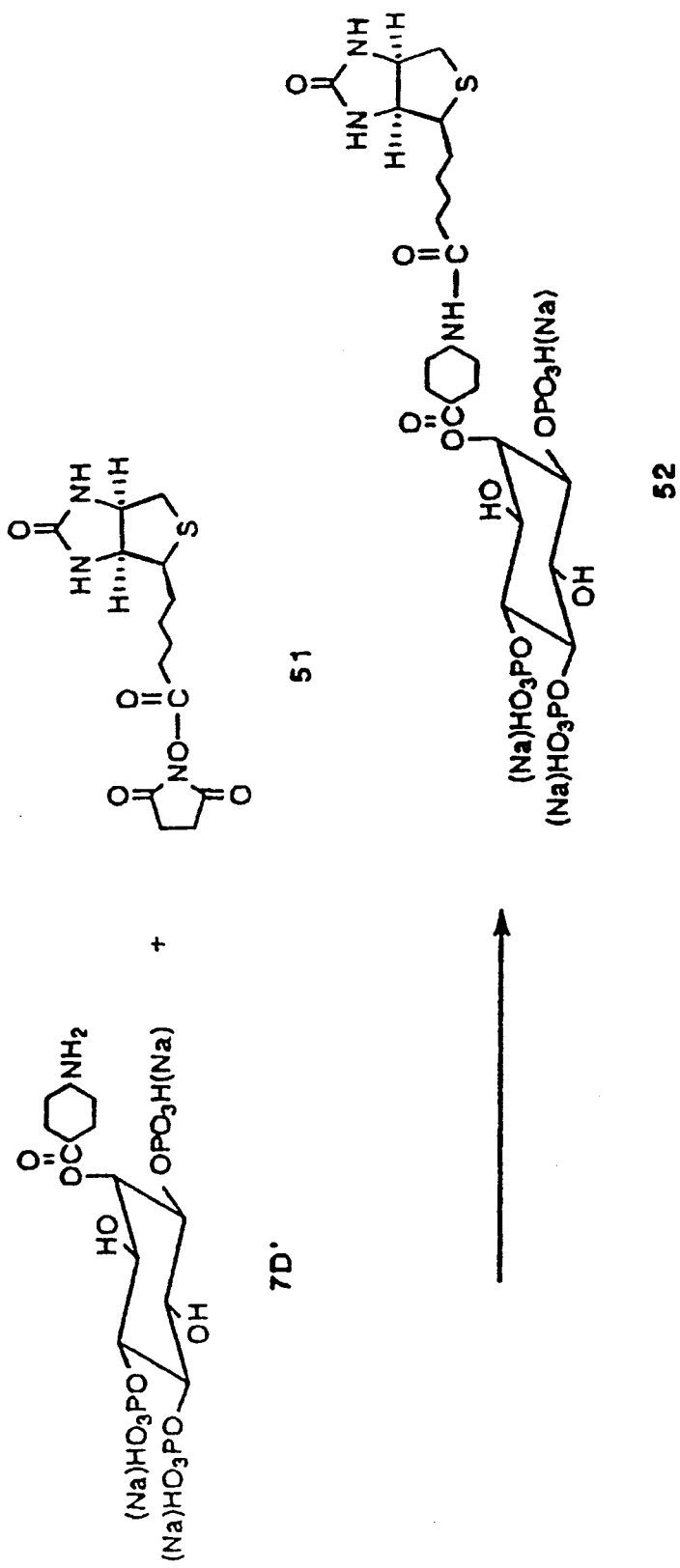
FIG. 7 shows the condensation reaction of biotin and the compound 7D'.
Figure 8:
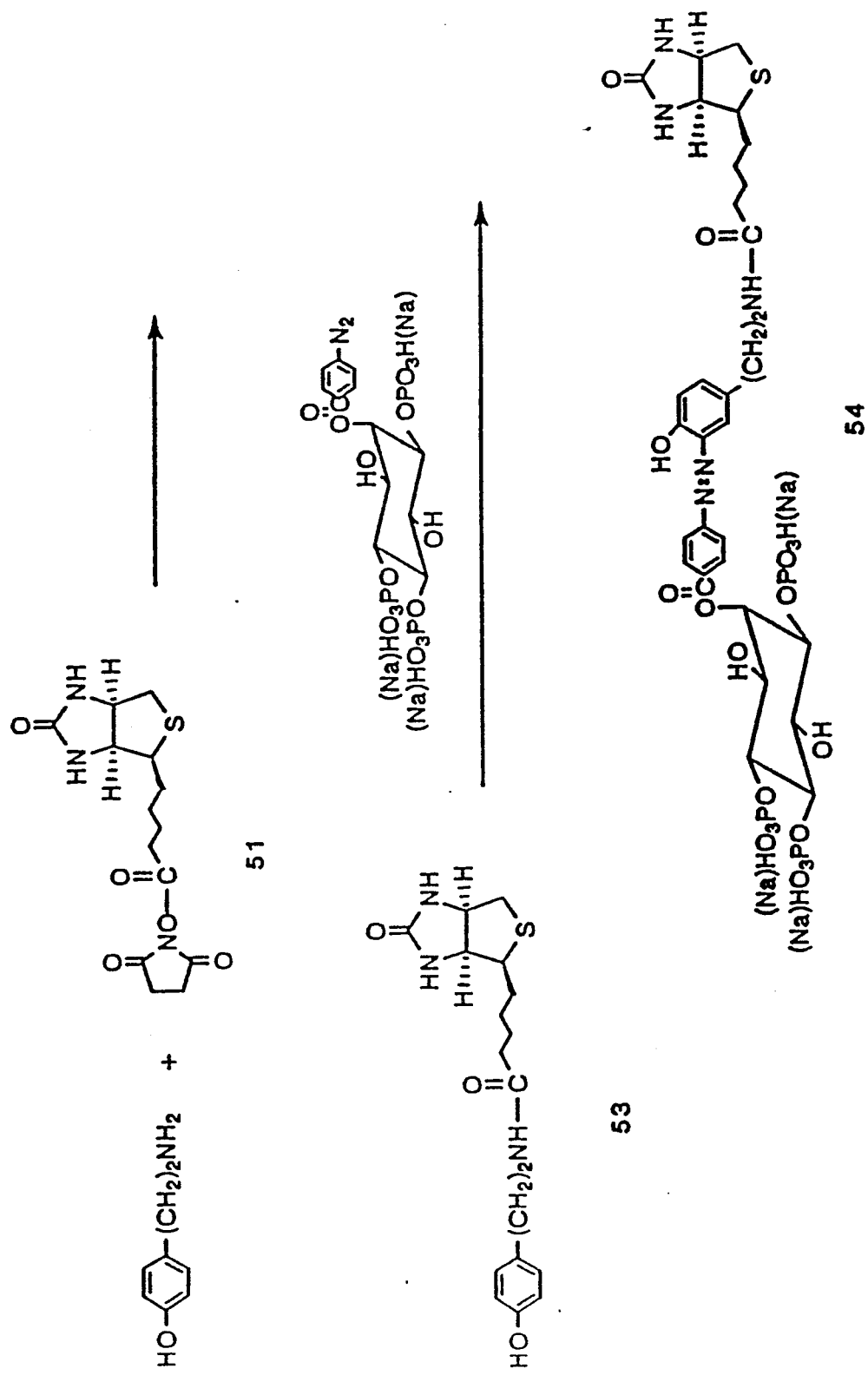
FIG. 8 shows the synthetic route of a biotin-tyramine-compound 6 composite.
Figure 9:
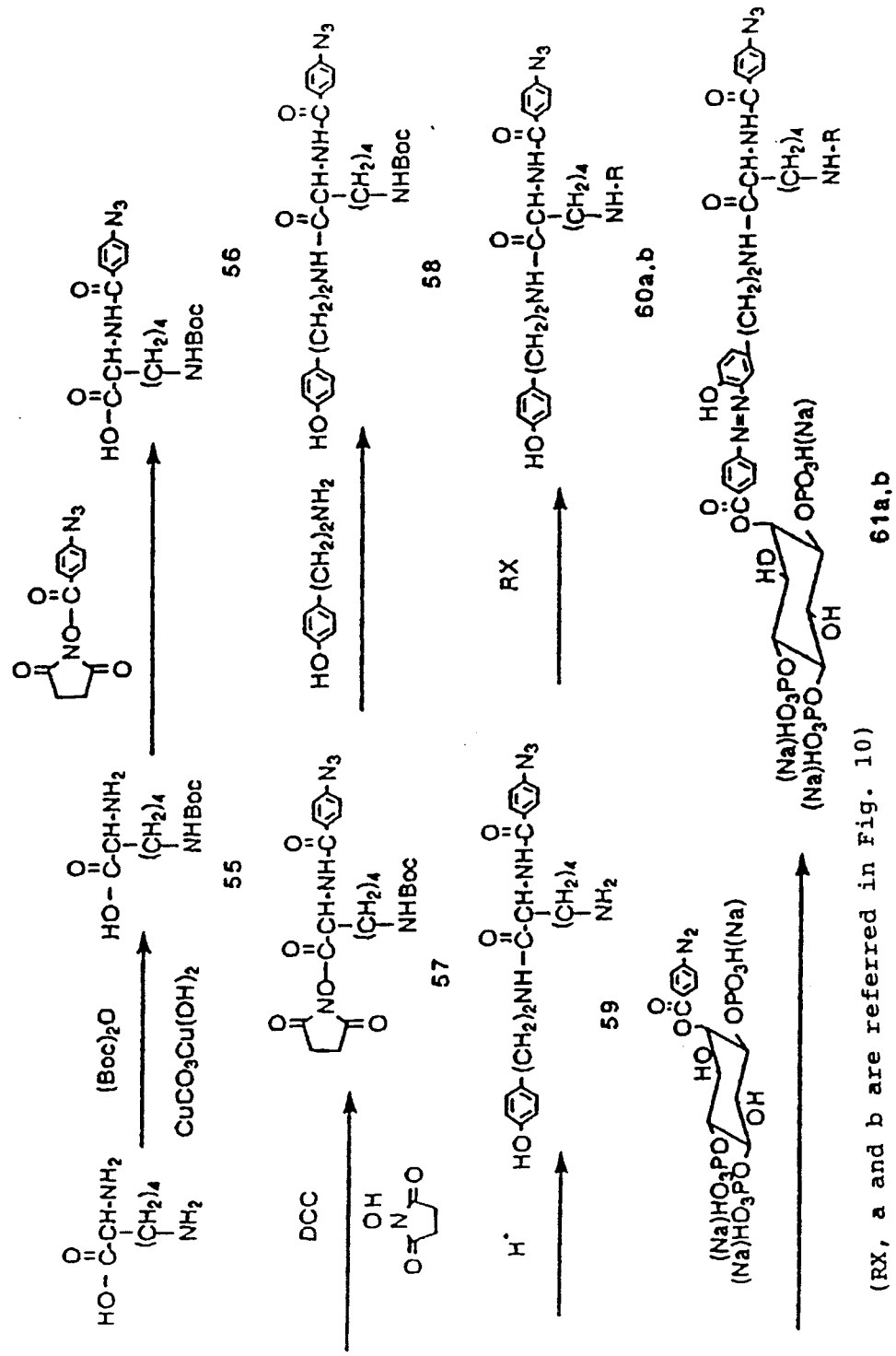
FIG. 9 shows the synthetic route of a photodecomposable group and biotin or $IP_3$ having a fluorescent substance.
Figure 10:
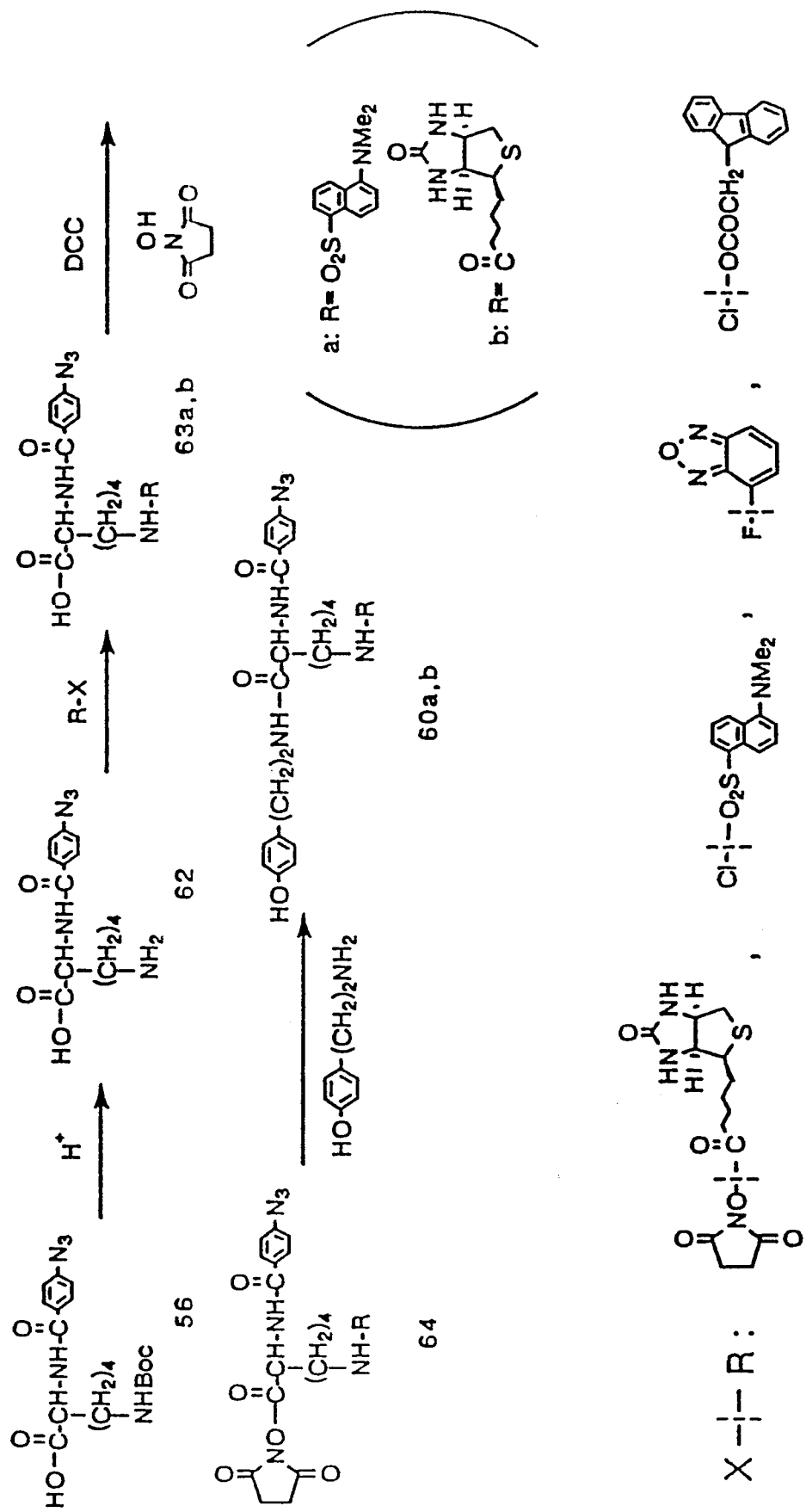
FIG. 10 shows another synthetic route for a compound 60 present in FIG. 9.
Figure 11:
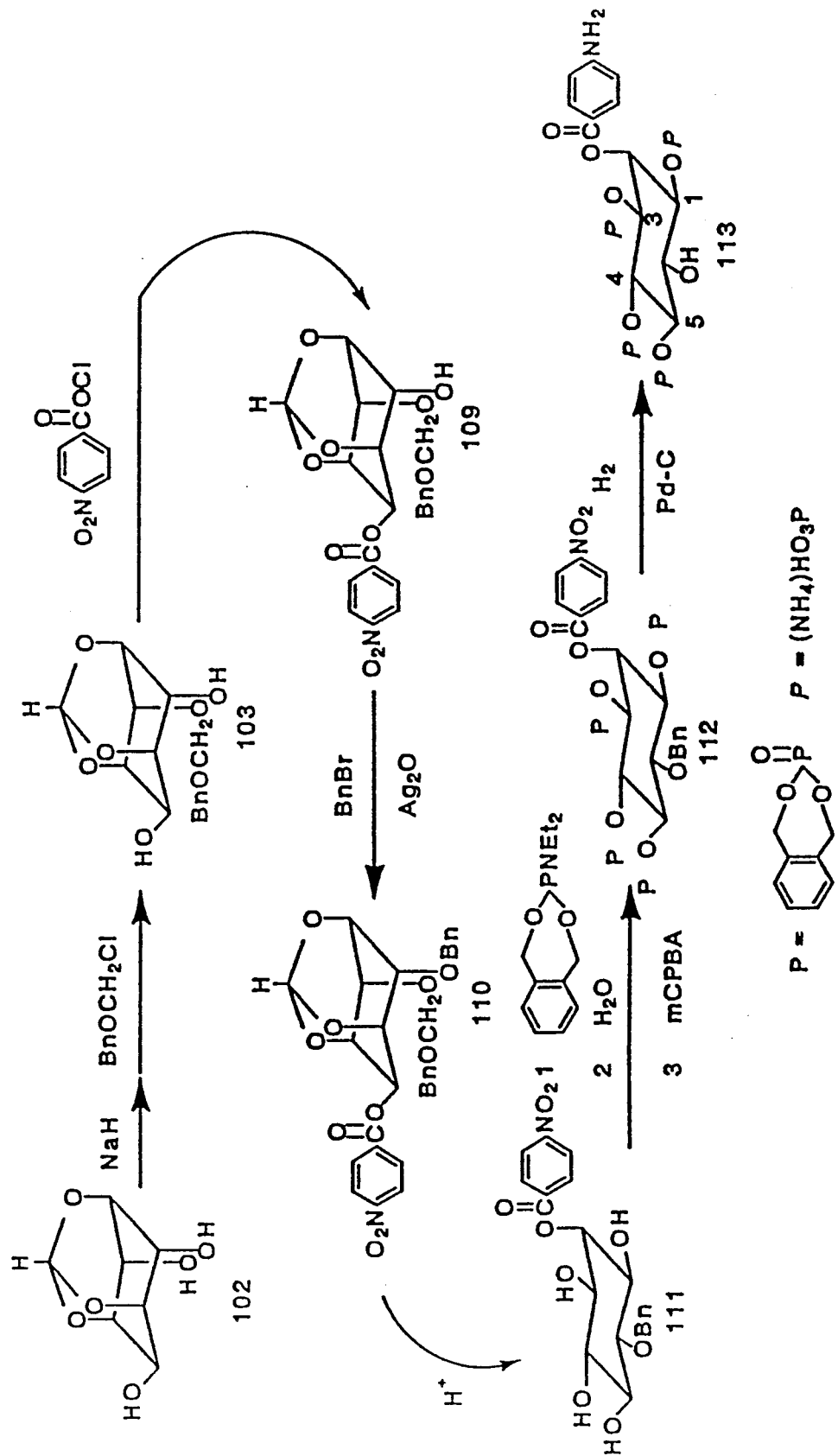
FIG. 11 shows a manufacturing process for $IP_4$-2 position P-aminobenzoyl substance.
Figure 12:
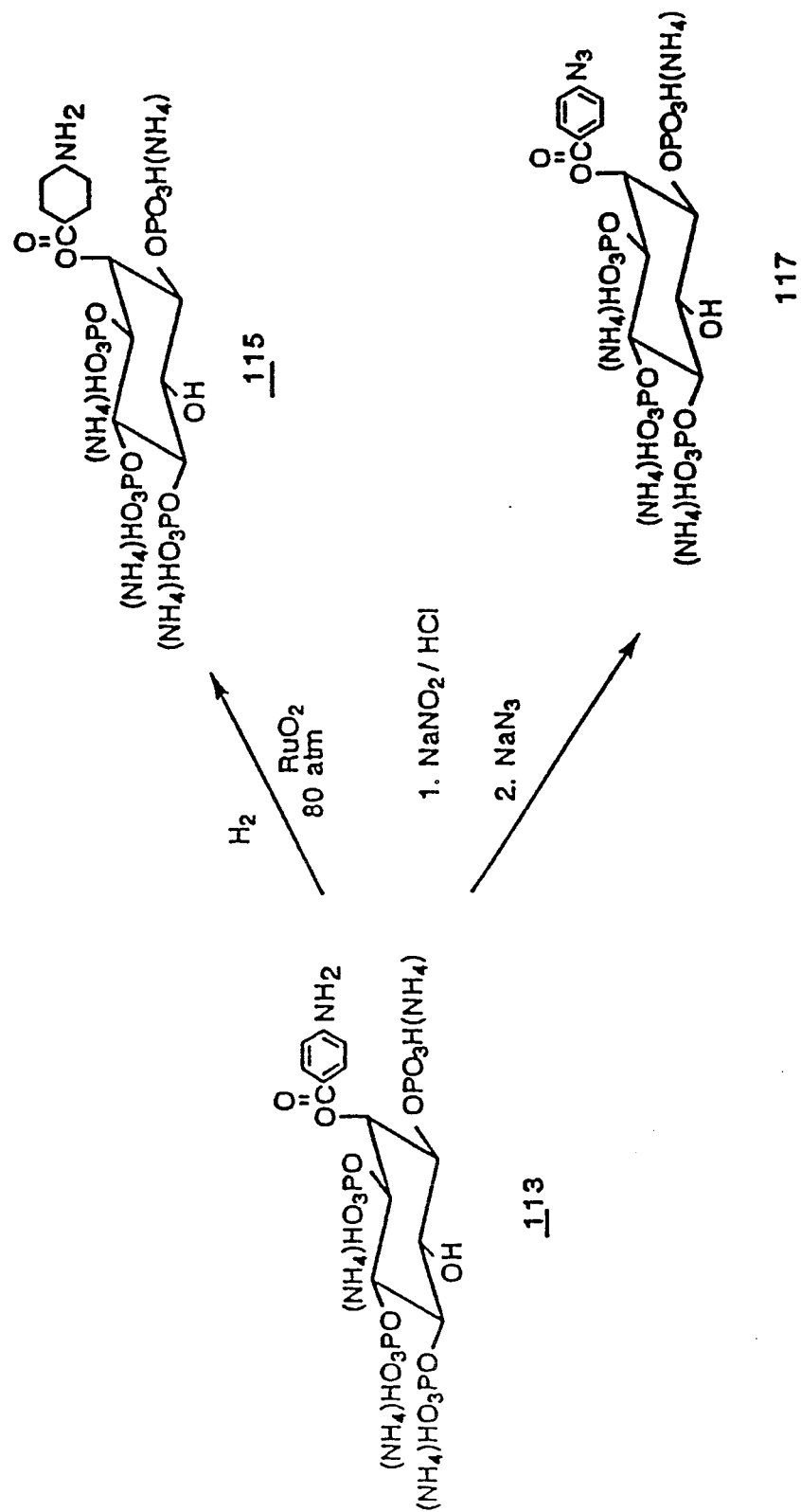
FIG. 12 shows the chemical conversion of 2-P-aminobenzoyl-$IP_4$.
Figure 13:
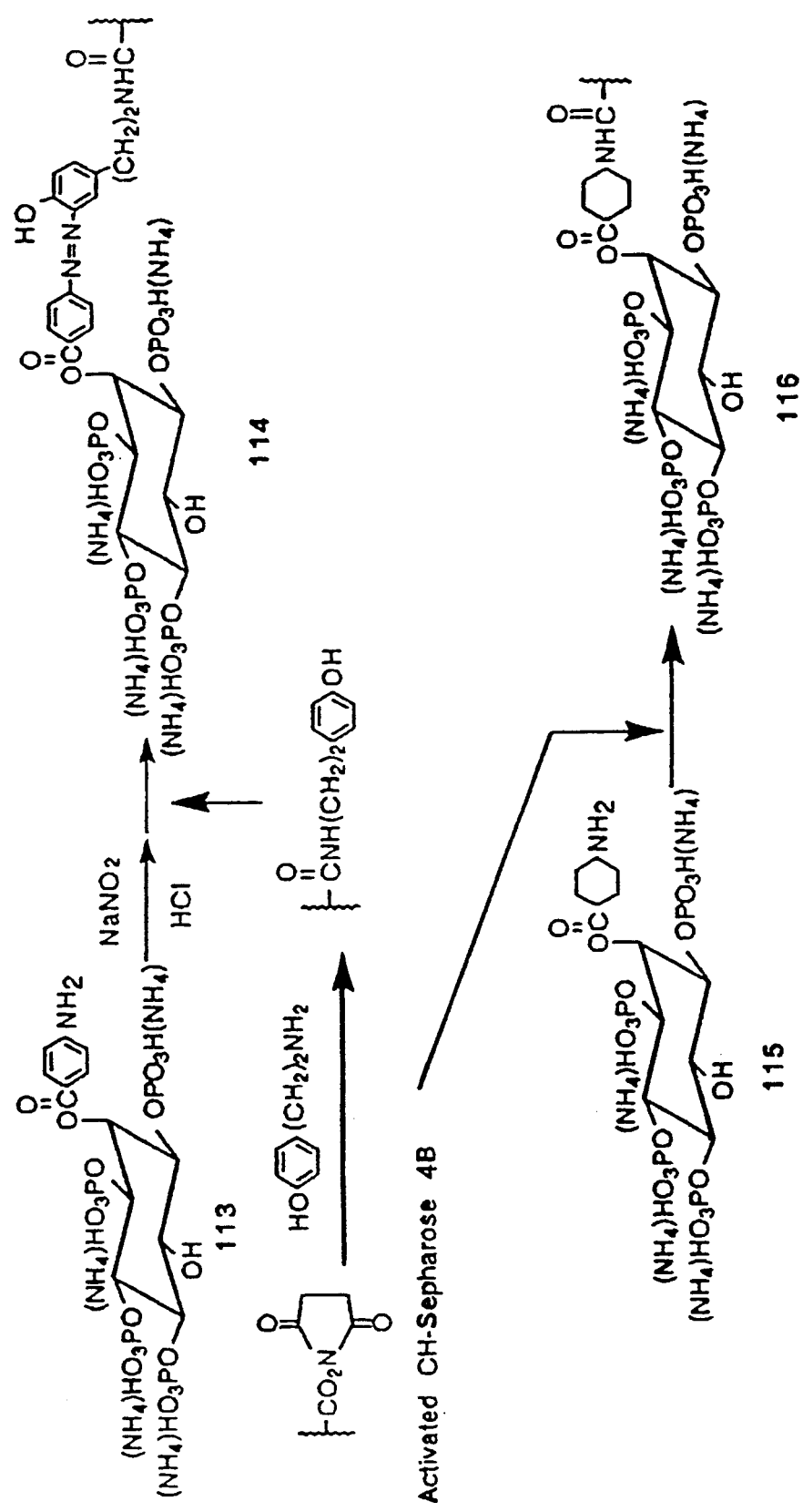
FIG. 13 shows a manufacturing process of an $IP_4$-tyramine-containing Sepharose series affinity column.
Figure 14:
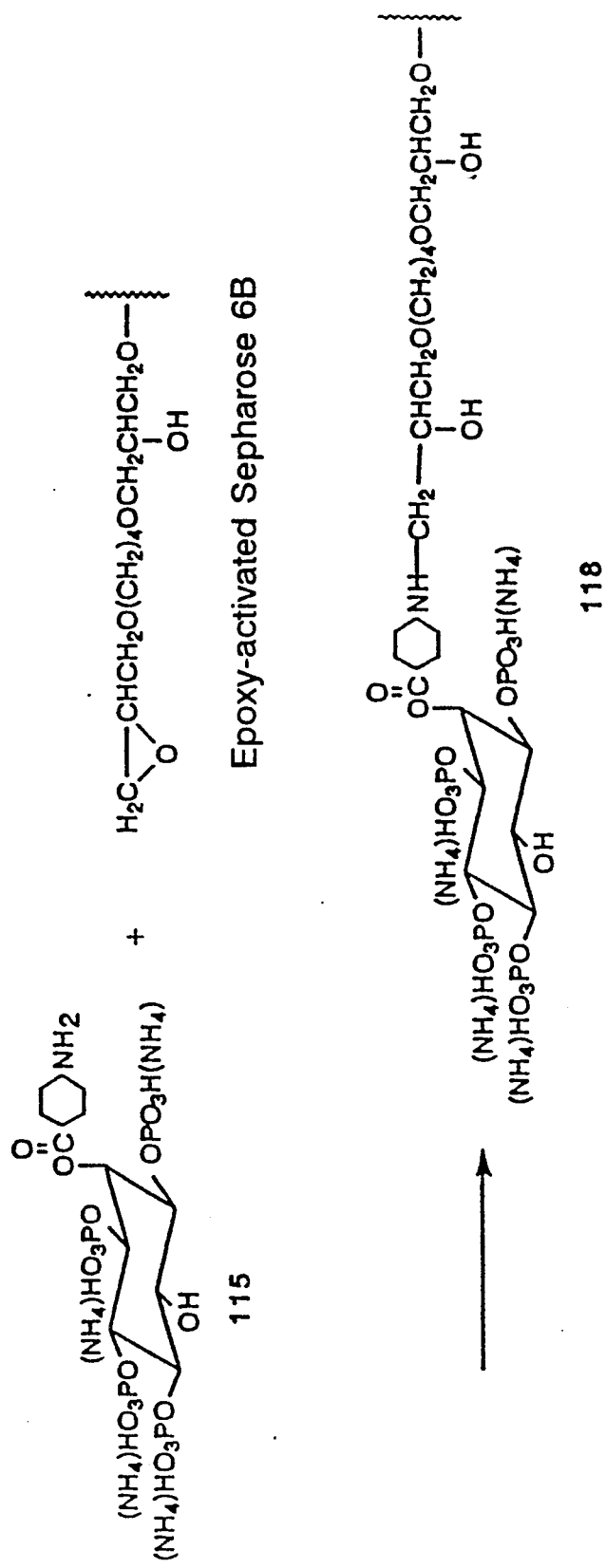
FIG. 14 shows a manufacturing process of the affinity column using an epoxydized Sepharose.
Figure 15:
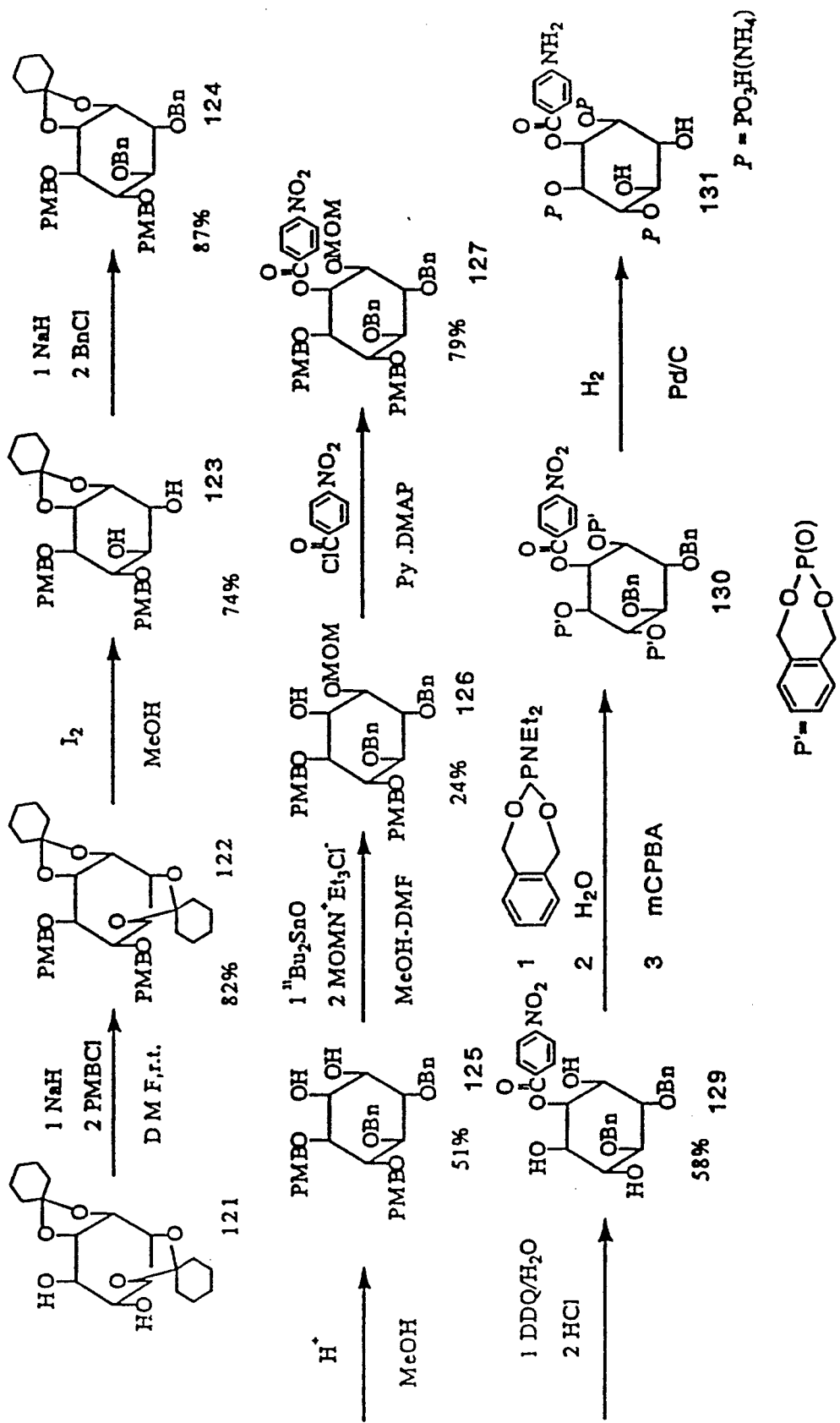
FIG. 15 shows a manufacturing process of a 1,3,4-$IP_3$ derivative.
Figure 16:
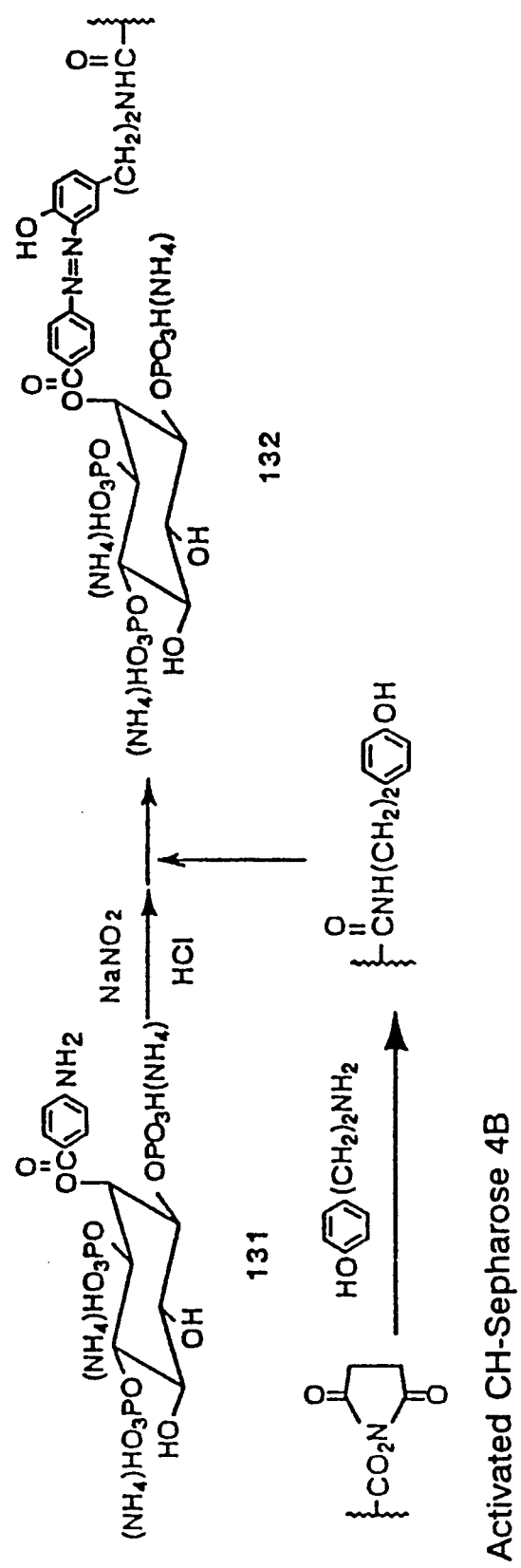
FIG. 16 shows a manufacturing process of a 1,3,4-$IP_3$ affinity column.
Figure 17:
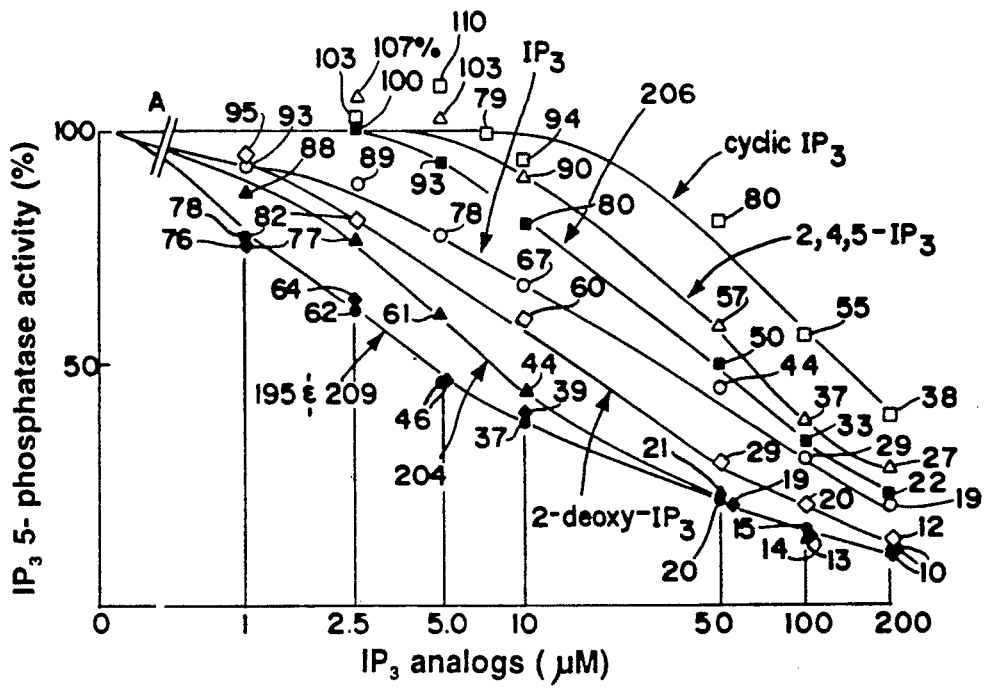
FIGS. 17A-B shows relations between concentrations of various $IP_3$ analogs and $IP_3$-P-phosphatase activity.
Figure 17:
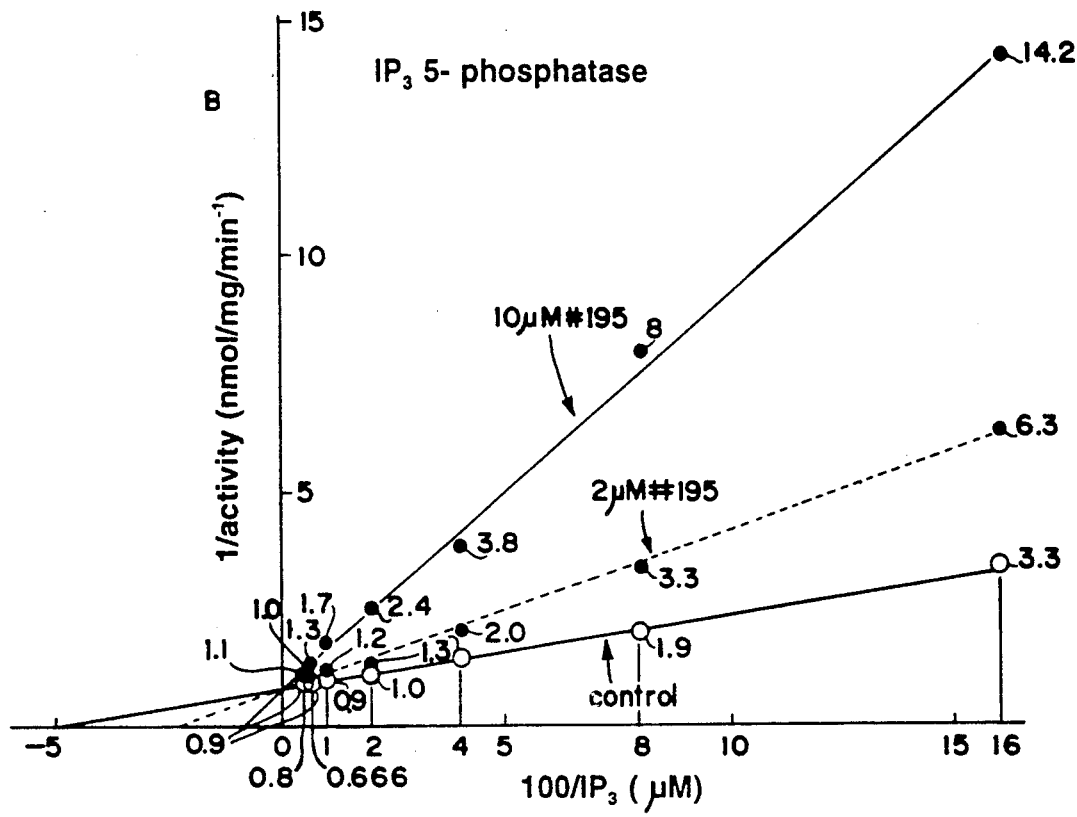
Figure 18:
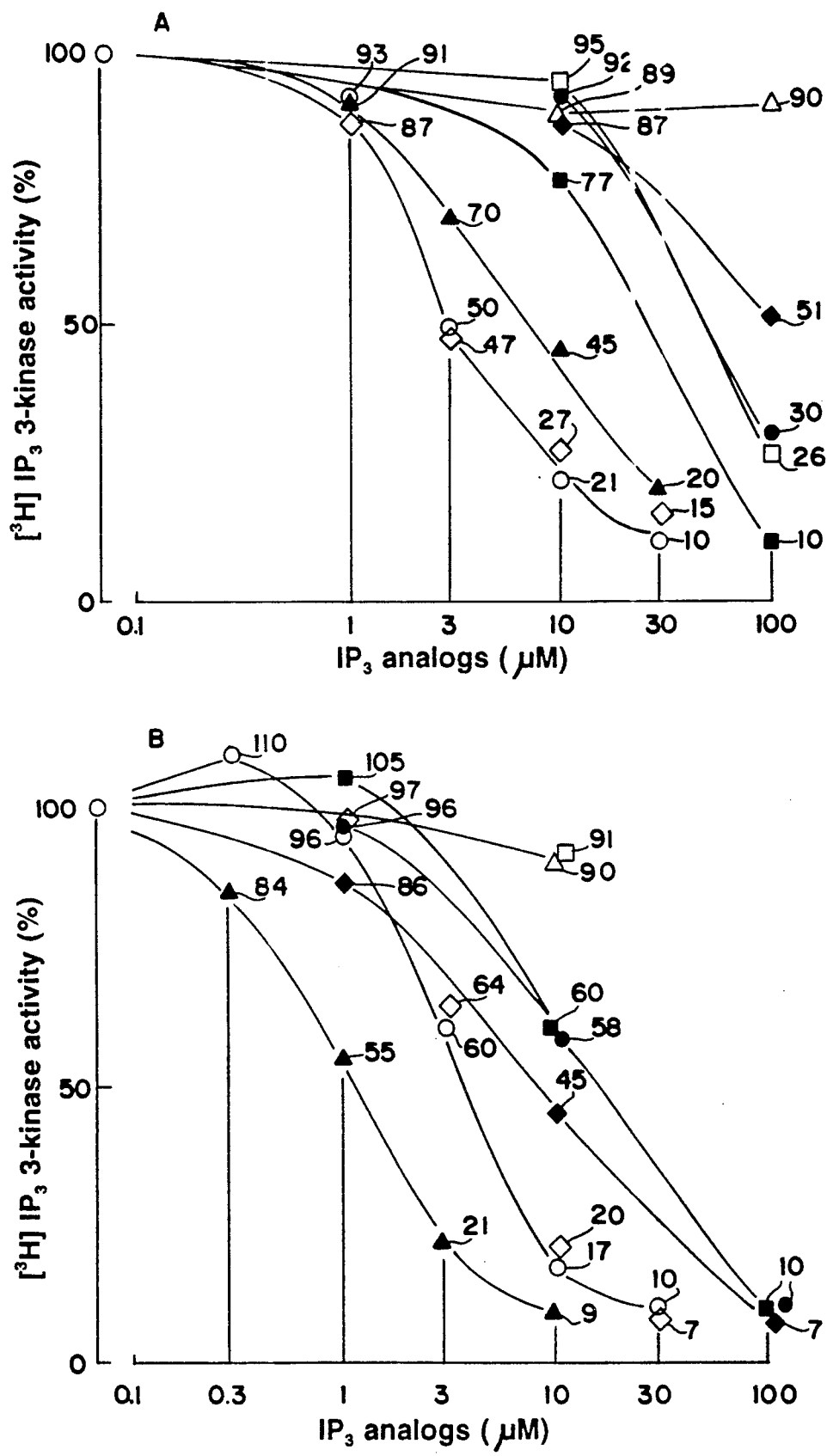
FIGS. 18A-B shows relations between concentrations of various $IP_3$ analogs and [$^3H$]$IP_3$-3-kinase activity.
Figure 19:
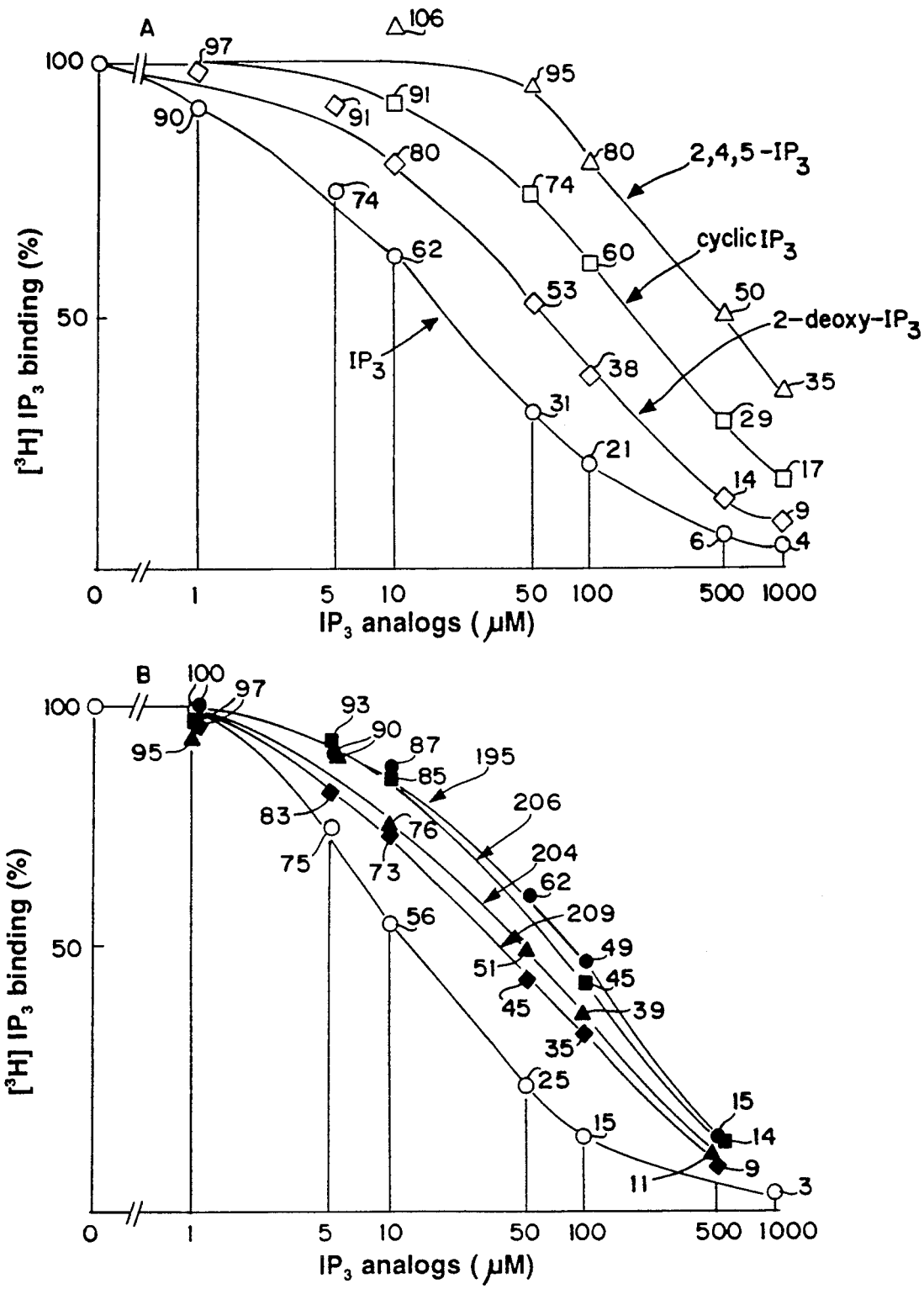
FIGS. 19A-B shows relations between concentrations of various $IP_3$ analogs and [$^3H$]$IP_3$ binding (%).
Figure 20:
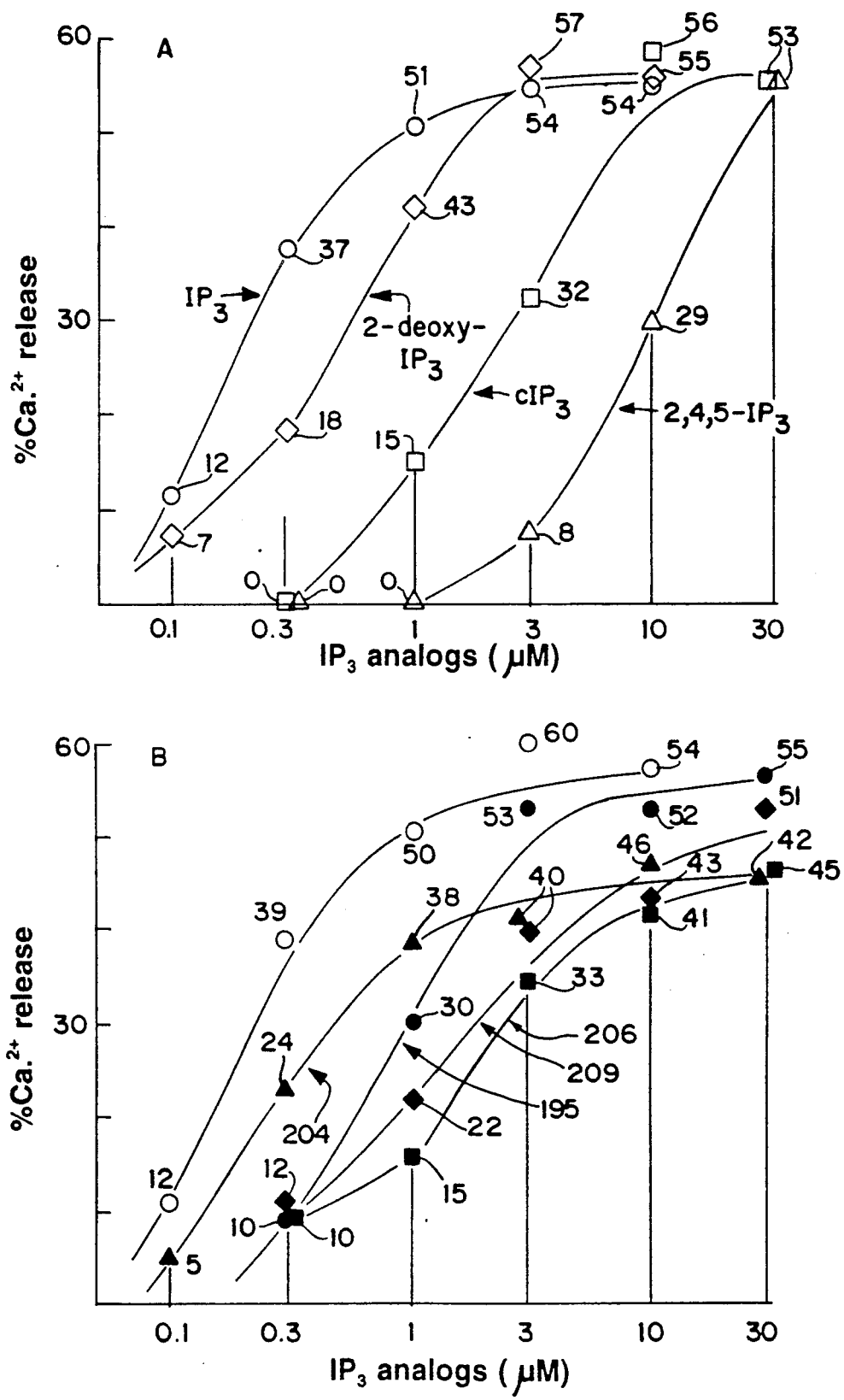
FIGS. 20A-B shows relations between concentrations of various $IP_3$ analogs and $Ca^{2+}$ release (%).
Figure 21:
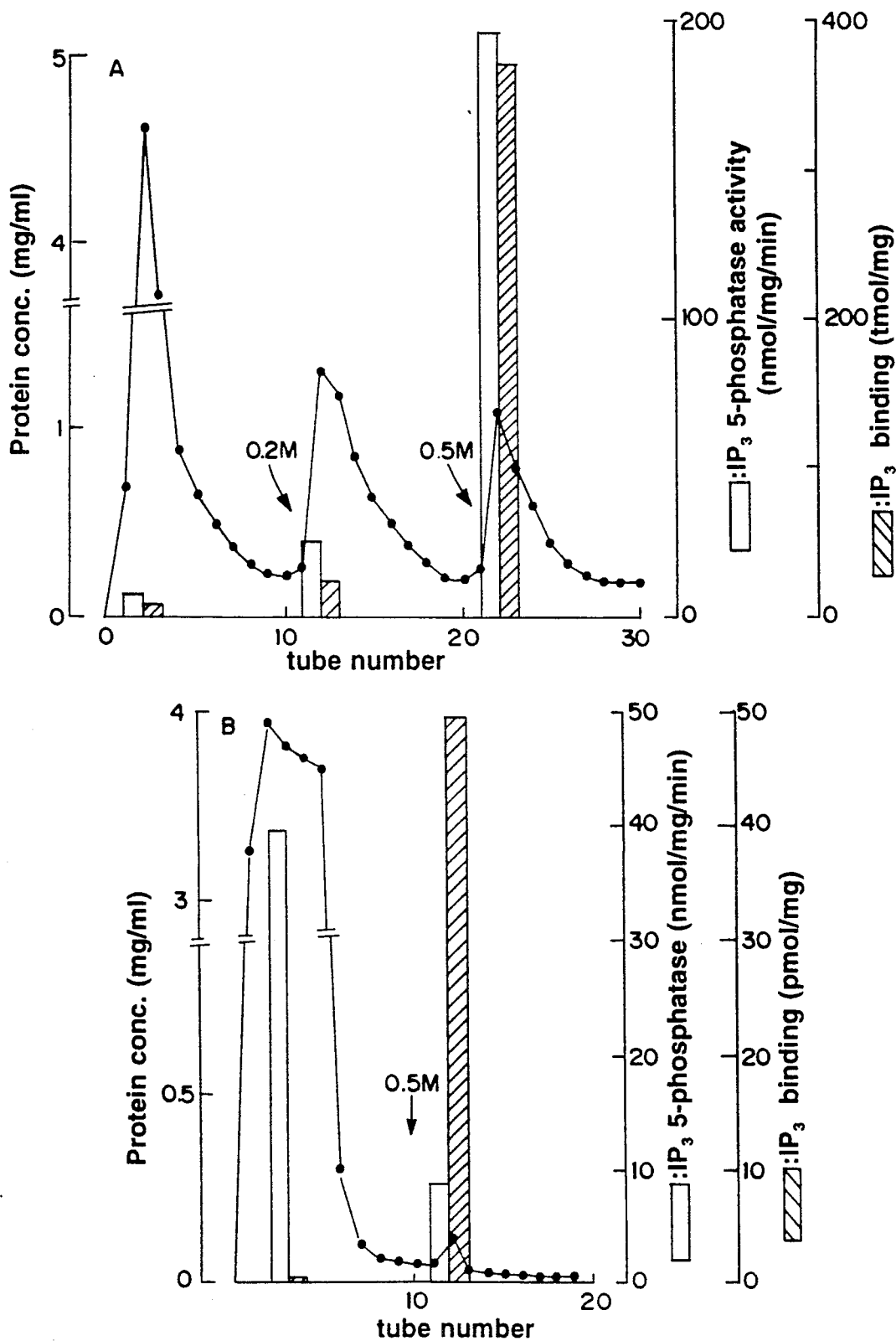
FIGS. 21A-B shows relations between tube numbers and protein concentrations (mg/ml) in the separation/purification of proteins regarding $IP_3$ by a column packed with compounds 10D' and 11D'.
Figure 22:
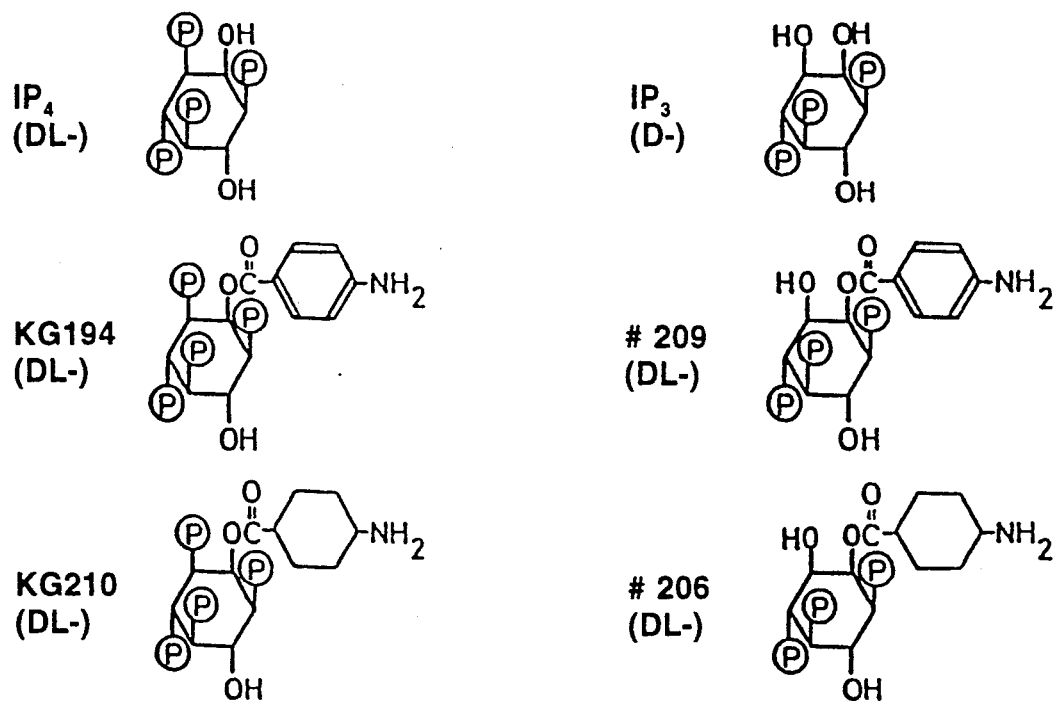
FIG. 22 shows various $IP_4$ and $IP_3$ analogs.

The glanule fraction of a rat brain was extracted at 4° C. for 30 minutes with 1% Triton X-100, and the extract (4.9 mg/ml×6 ml) was introduced into a column packed with 3 ml of a compound 10D'. In order to elute an adsorbed protein, 0.2M or 0.5M of a sodium chloride solution was allowed to flow through the column. 10 fractions each containing 3 ml of the eluate were collected, and in each of the eleventh et seq. fractions, 1 ml of the eluate was contained. For the three fractions (Nos. 2, 12 and 22), an $IP_3$-5-phösphatase activity and a [$^3$H]IP$_3$ bond activity were measured at an $IP_3$ concentration of 10 $\mu$M or 3.5 nM, respectively. With regard to the specific activities of the extracts, the former was 42 nmol/mg/minute, and the latter was 78.5 fmol/mg. In the eluate obtained with the 0.5M sodium chloride solution, both the activities were 3 to 5 times higher than in the first extract. In addition, an $IP_3$-3-kinase activity was also higher. The results are set forth in FIG. 6A. In other two experiments, the similar results were obtained.

On the other hand, in the column packed with a compound 11D', a very small amount of a protein was adsorbed. In the case of a 0.2M sodium chloride solution, the protein was not eluted in such an amount to be measurable, and in the case of a 0.5M sodium chloride, all the protein was eluted. The specific activity of the [$^3$H]IP$_3$ bond was heightened 95 times as much as that of the first extract. On the other hand, the $IP_3$-5-phosphatase activity was not increased by passing through the column. That is, a rat brain Triton extract (4.1 mg/ml×13 ml) was introduced into a column packed with 3 ml of a compound 11D', and 10 fractions each containing 3 ml of the eluate were collected, and in each of the eleventh et seq. fractions, 1 ml of the eluate was contained. For the two fractions (Nos. 2 and 12), an $IP_3$-5-phosphatase activity and a [$^3$H]IP$_3$ bond activity were measured at concentrations of 10 $\mu$M and 60 nM of $IP_3$, respectively. The specific activities of the first extract were 42 nmol/mg/minute or 0.51 pmol/mg, respectively. The results are set forth in FIG. 6B. In other two experiments, the similar results were obtained.

Experimental Example 5 Interaction with $IP_4$-5-phosphatase

Figure 23:
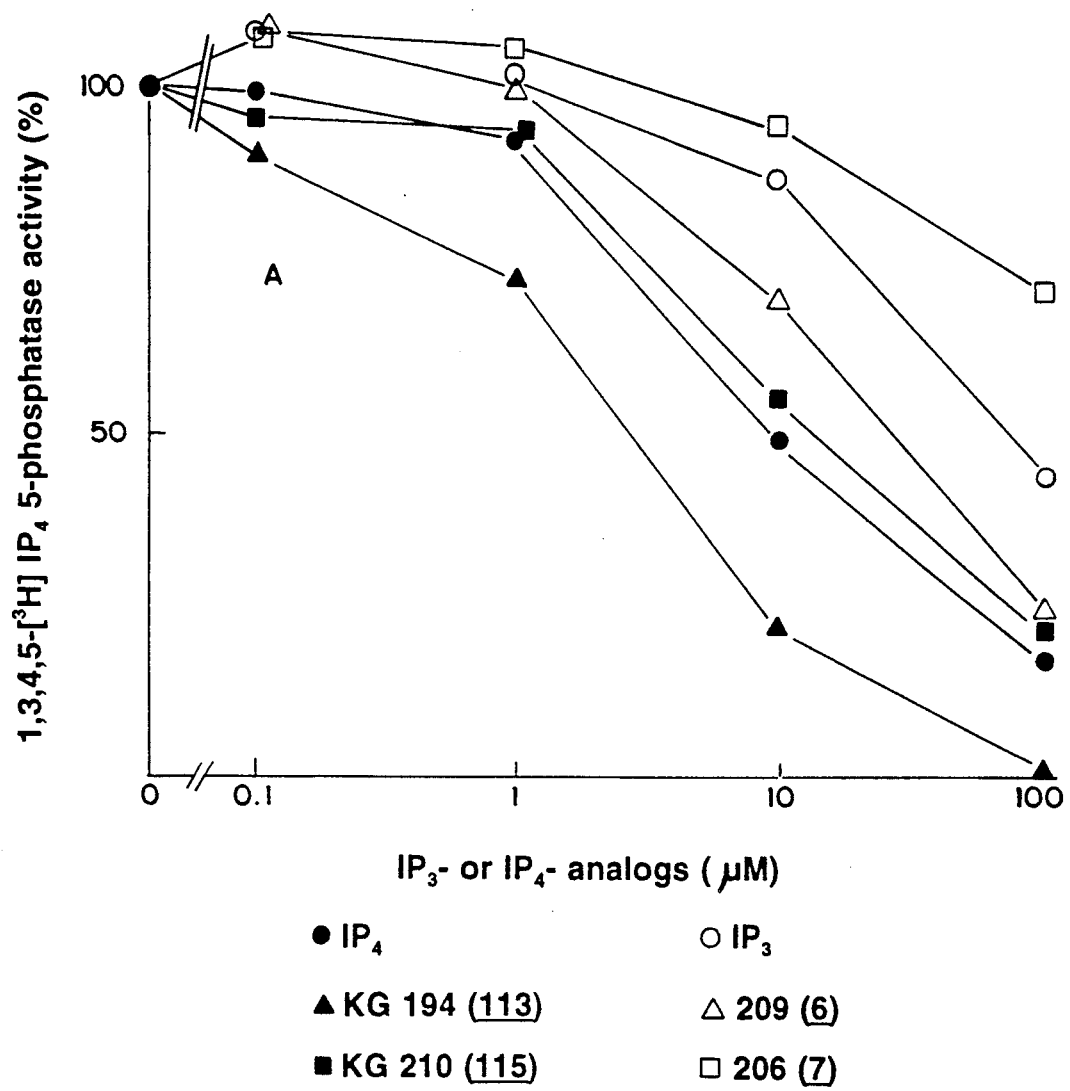
FIG. 23 shows relations between concentration of various $IP_3$ and $IP_4$ analogs and $IP_4$-5-phosphatase activity.

The activity of $IP_4$-5-phosphatase in human red cell ghosts was measured. The red cell ghosts were collected from a blood in accordance with a Downes' method in Experimental Example 1, and an enzyme activity was measured on the basis of a radiation chemistry. A reaction solution (0.2 ml) was prepared which contained 20 mM of a Hepes buffer solution (pH 7.0), 5 mM of $MgCl_2$, 0.2 mg/ml of saponin and 1 $\mu$M of D-$IP_4$ containing 370 Bq[$^3$H]IP$_4$. This solution was maintained at 37° C. for about 2 minutes, and 150 $\mu$g of the red cell ghosts was added to the solution, so that reaction began. The reaction was continued for 15 minutes, and the same amount of 20% trichloroacetic acid was added to bring the reaction to an end. After the removal of a protein, extraction was effected with 3 ml of diethyl ether three times, and the decrease of [$^3$H]IP$_4$ was measured by introducing the sample into an SAX column of HPLC. The results are shown in Table 4 and FIG. 23.

Experimental Example 6 Interaction with $IP_4$-3-phosphatase

Figure 24:
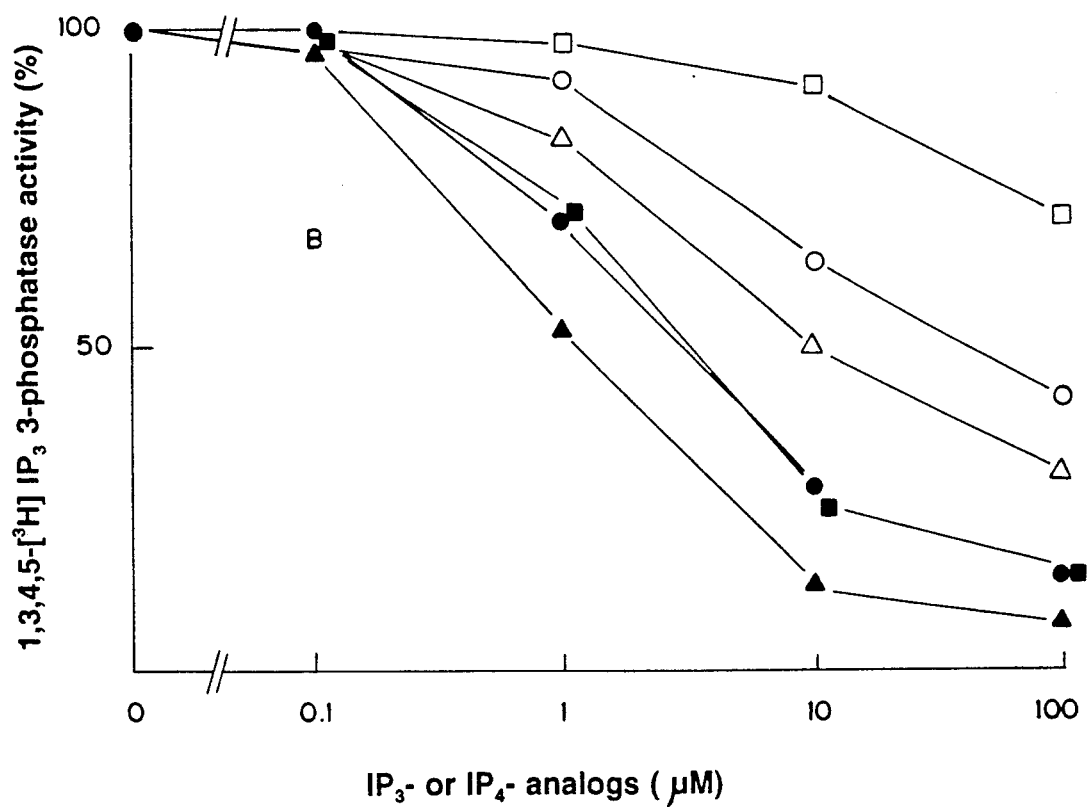
FIG. 24 shows relations between concentrations of various $IP_3$ and $IP_4$ analogs and $IP_4$-3-phosphatase activity.

A test was carried out in a system using human red cell ghosts by the same procedure as in Experimental Examples 1 and 5. The different points than in the case of the measurement of $IP_4$-5-phosphatase are that 2 mM of EDTA was replaced with $MgCl_2$ and that a reaction time was 40 minutes. The results are set forth in Table 4 and FIG. 24.

Experimental Example 7 Interaction with $IP_3$-5-phosphatase

Figure 25:
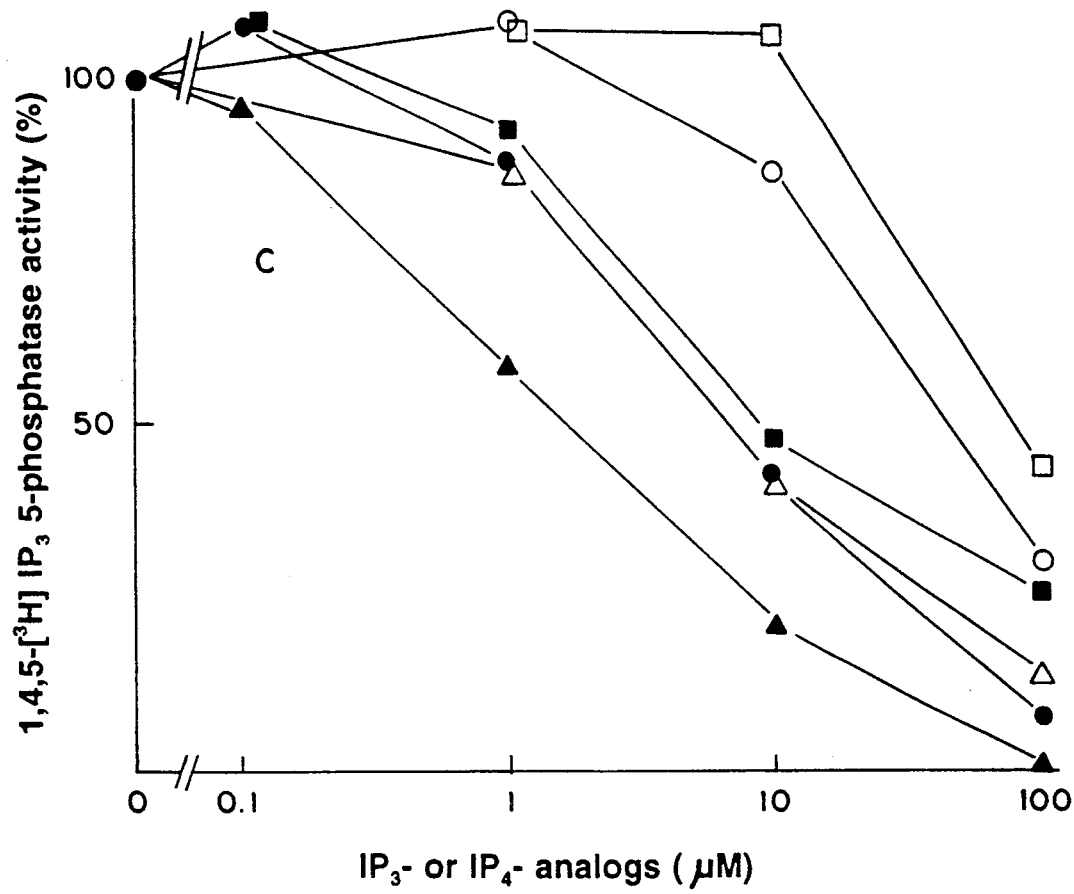
FIG. 25 shows relations between concentrations of various $IP_3$ and $IP_4$ analogs and $IP_3$-5-phosphatase activity.

A test was carried out in accordance with the same procedure as in Experimental Example 1. [$^3$H]IP$_3$ having a concentration of 10 $\mu$M was used as a substrate. Additionally, an inhibition activity of an $IP_4$ analog was compared with that of an IP₃ analog. The results are shown in Table 4 and FIG. 25.

Experimental Example 8 Influence on [³H]IP bond ability

Figure 26:
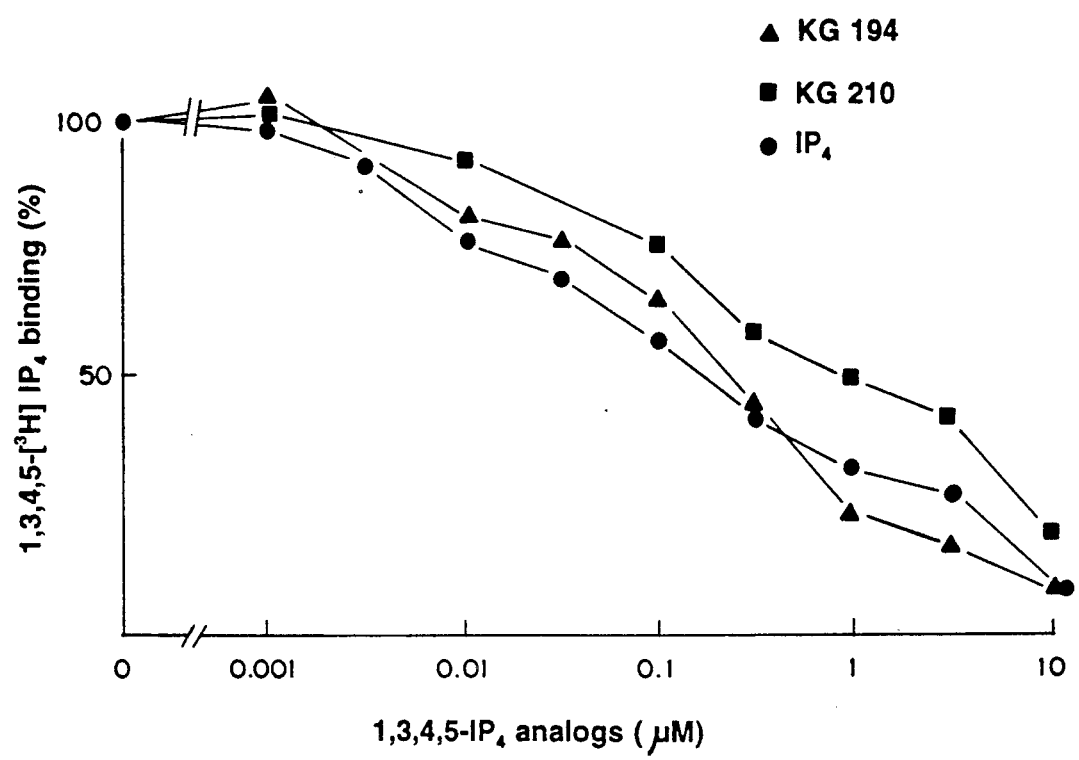
FIG. 26 shows relations between concentrations of various $IP_4$ analogs and [$^3H$]-$IP_4$ bonding (%).

The microsome of a rat cerebellum was prepared in accordance with the same procedure as in Experimental Example 3, and [³H]IP₄ bond to the microsome was measured. In a used reaction solution (0.5 ml), there were contained 50 mM of a buffer solution selected from a 2-(N-morpholino)ethanesulfonic acid (Mes, pH 5.0) buffer solution, a Hepes buffer solution and a Tris-HCl buffer solution, 1 mM of EDTA, 1.18 nM of [³H]IP₄ and 400 μg of a microsome fraction. Reaction was carried out on ice for 15 minutes, and afterward the reaction solution was passed through a Whatman GF/C glass fiber filter under reduced pressure. A used filter paper was washed with 2 ml of the buffer solution and then dried, and radioactivity was measured. The results are shown in FIG. 26.

TABLE 4

| | Effect of IP₄ analog to IP₄-5-phosphatase and IP₃-phosphatase | | | |
|---|---|---|---|---|
| Compound | Ki [³H]IP₄-5-phosphatase | IC₅₀ [³H]IP₄-3-phosphatase | Ki 1,4,5-[³H]IP₃-5-phosphatase | Hydrolysis by IP₄-5-phosphatase |
| IP₄ | 5.2$^{a}$μM | 2.8$^{b}$μM | 2.5$^{a}$μM | 1.1$^{cnmol}$ |
| KG194 | 0.8 | 1.4 | 0.7 | 0.70 |
| KG210 | 12.8 | 3.3 | 6 | 0.74 |

$^{a}$Apparent Ki values were determined from a Dixon plot. Each value was an average of two experiments.
$^{b}$IC₅₀ was calculated from FIG. 24.
$^{c}$Human red cell ghosts (0.34 mg) were incubated together with 10 μM of an IP₄ analog at 37° C. for 60 minutes. Each value was an average of three experiments by duplication.

FIELD OF INDUSTRIAL UTILIZATION

An inositol derivative of the present invention has a utilizable field as a medicine, and a bonded substance of the inositol derivative and a polypeptide or a protein has a utilizable field as a reagent for research, diagnostic agent for medicine, a (healthy) food and the like. That is, an IP₃ derivative of the present invention has about the same biological activity as in IP₃ itself as well as an inhibition activity to the function of IP₃ and the like, and it functions like IP₃ produced in an organism by administration from the outside or functions antagonistically to IP₃ produced in the organism, so that it exerts activity as a medicine. On the other hand, an IP₄ derivative of the present invention also has about the same biological activity as in IP₄ itself as well as an inhibition activity to the function of IP₃ or IP₄ and the like, and it functions like IP₃, 1,3,4-IP₃ or IP₄ produced in the organism by administration from the outside or functions antagonistically to IP₃, 1,3,4-IP₃ or IP₄ produced in the organism, so that it exerts activity as a medicine. Furthermore, the present invention also provides an IP₃ derivative-bonded solid phase carrier and an IP₄ derivative-bonded solid phase carrier which are useful for separation and purification of proteins such as IP₃ phosphatase, IP₄ phosphatase, IP₃ kinase, IP₄ kinase, IP₃ receptor, IP₄ receptor and the like regarding the in vivo metabolism of IP₃ and IP₄. Therefore, the present invention can contribute to the analysis of active sites of these proteins and bond sites of IP₃ compounds and IP₄ compounds, the genetic analysis of these proteins, and production technology on the basis of genetic engineering with the aid of cells and bacteria.

In addition, biotin-bonded and fluorescent-bonded substances of IP₃, 1,3,4-IP₃, IP₄ and the like of the present invention are useful to search active sites, functional mechanism and structure-activity interrelation of affinity proteins such as phosphatase, kinase, a receptor and the like in connection with inositol phosphate compounds. That is, according to the present invention, a biotin-avidin composite probe or a probe utilizing fluorescence can be prepared which can be used as an indicator for searching each active site by irradiating with light to generate nitrene, and then covalently bonding an amino acid residue in the vicinity of an active point to IP₃ or the like.

We claim:

1. An inositol derivative represented by formula (II) or (III)

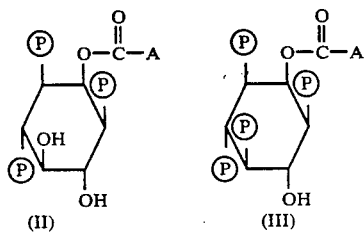

wherein A is (CH₂)$_n$CH(R')NH₂,

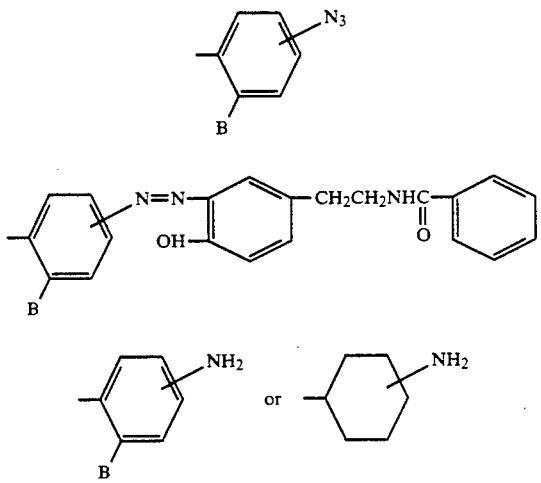

R' is a hydrogen atom, a lower alkyl group having 1 to 5 carbon atoms, a lower hydroxyalkyl group, a lower aminoalkyl group, a phenyl group, a p-hydroxyphenyl group, a benzyl group, a p-hydroxybenzyl group, a 3-methylindole group, or a 5-methylimidazole group; n is from 0 to 5; each of R¹ to R⁵ is a hydrogen atom, an alkyl group, an alkenyl group, an alkynyl group or a phenyl group, a phenyl group mono- or tetra substituted by an alkyl group having 1 to 4 carbon atoms or a halogen atom, a cyclohexyl group or a cyclohexyl group mono- or tetra-substituted by an alkyl group having 1 to 4 carbon atoms or a halogen atom; B is a hydrogen atom, NH₂ or NHCOCFH₃; Ⓟ is a phosphoric acid group which is free or protected by a protective group or a pharmaceutically acceptable salt of the inositol derivative.

2. A solid phase carrier having the inositol derivative of formula (II) or (III) of claim 12 bonded thereto.

3. A process for preparing a compound represented by the formula (II) or (III) of claim 12 which comprises the step of phosphorylating a myoinositol in which the 5 and 6 positions or the 6 position is protected with a benzyl group or a substituted benzyl group or in which the 2 position is protected with an acyl group.

4. A conjugate of the inositol derivative of claim 1 bonded to a protein or a polypeptide.

5. An inositol derivative represented by the formula (I)

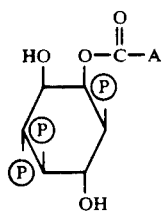

wherein A is

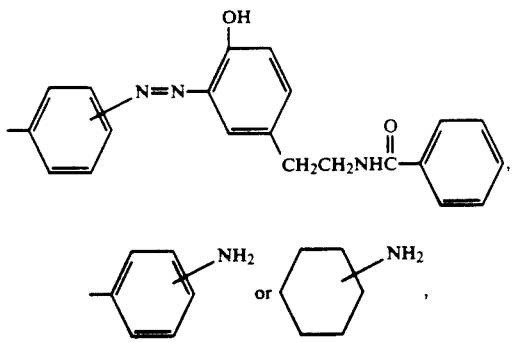

and ⓟ is a phosphoric acid group which is free or protected by a protective group, or a pharmaceutically acceptable salt of the inositol derivative.

6. A process for preparing a salt represented by formula (I) of claim 5 which comprises the steps of previously protecting the hydroxyl group at the 1 position of an inositol-4,5-diphosphoric acid derivative with a silanizing agent, reacting said derivative with a carboxylic acid, removing the silyl group, phosphorylating the 1 position to produce an inositol-1,4,5-triphosphoric acid derivative in which the 2 position is substituted by a carboxylic ester, reacting this derivative with a reducing agent to produce a salt of an inositol-1,4,5-triphosphoric acid in which the 2 position is substituted by a carboxylic ester substituted by an amino group, and then reducing by reaction of a nitrite and an azido compound, reaction of a nitrite, p-aminoethyl-phenol and an acid, reaction with an aldehyde, reaction with a ketone, reaction with an isocycanate, reaction with chlorocarbonic ester or reaction with a carboxylic acid.

7. The process of claim 6 wherein the carboxylic acid reacted with the protected inositol-4,5-diphosphoric acid derivative has one amino group or nitro group.

* * * * *